United States Patent
Sucholeiki

(10) Patent No.: US 9,505,743 B2
(45) Date of Patent: Nov. 29, 2016

(54) MATRIX METALLOPROTEINASE INHIBITORS AND METHODS FOR THE TREATMENT OF PAIN AND OTHER DISEASES

(71) Applicant: AQUILUS PHARMACEUTICALS, INC., Winchester, MA (US)

(72) Inventor: Irving Sucholeiki, Winchester, MA (US)

( * ) Notice: Subject to any disclaimer, the term of this patent is extended or adjusted under 35 U.S.C. 154(b) by 0 days.

(21) Appl. No.: 14/433,692

(22) PCT Filed: Nov. 27, 2012

(86) PCT No.: PCT/US2012/066619
§ 371 (c)(1),
(2) Date: Apr. 6, 2015

(87) PCT Pub. No.: WO2014/062204
PCT Pub. Date: Apr. 24, 2014

(65) Prior Publication Data
US 2015/0274702 A1    Oct. 1, 2015

Related U.S. Application Data

(60) Provisional application No. 61/713,660, filed on Oct. 15, 2012.

(51) Int. Cl.
| | | |
|---|---|---|
| *A61K 31/506* | (2006.01) | |
| *C07D 403/12* | (2006.01) | |
| *A61K 45/06* | (2006.01) | |
| *C07D 239/28* | (2006.01) | |
| *C07D 413/12* | (2006.01) | |
| *A61K 31/505* | (2006.01) | |
| *A61K 31/538* | (2006.01) | |
| *C07D 413/14* | (2006.01) | |

(52) U.S. Cl.
CPC ........... *C07D 403/12* (2013.01); *A61K 31/505* (2013.01); *A61K 31/506* (2013.01); *A61K 31/538* (2013.01); *A61K 45/06* (2013.01); *C07D 239/28* (2013.01); *C07D 413/12* (2013.01); *C07D 413/14* (2013.01)

(58) Field of Classification Search
CPC C07D 239/28; C07D 413/12; C07D 403/12; C07D 413/14; A61K 31/505; A61K 31/538; A61K 31/506; A61K 45/06
See application file for complete search history.

(56) References Cited

U.S. PATENT DOCUMENTS

| | | | |
|---|---|---|---|
| 2003/0229103 A1 | 12/2003 | Weithmann et al. | |
| 2005/0004111 A1* | 1/2005 | Klingler | C07D 239/28 514/227.5 |
| 2007/0155739 A1* | 7/2007 | Sucholeiki | C07D 239/28 514/230.5 |
| 2008/0021024 A1 | 1/2008 | Sucholeiki et al. | |

FOREIGN PATENT DOCUMENTS

WO     00/20357 A2    4/2000

OTHER PUBLICATIONS

International Preliminary Report on Patentability, PCT/US2012/066619 (Apr. 21, 2015).*
S.L. Harbeson et al., Deuterium in Drug Discovery and Development, in 46 Annual Reports in Medicinal Chemistry, 403-417, 405 (2011).*
International Application No. PCT/US2012/066619, International Filing Date Nov. 27, 2012, International Preliminary Report on Patentability date of report Feb. 8, 2013 and Written Opinion.
Walker et al. Improved Synthesis of (R)-glycine-d-15N. Tetrahedron 57 (2001) pp. 6695-6701.
Walker, J.R. et al. Improved Synthesis of (R)-glycine-d-15N. Tetrahedron 57 (2001): 6695-6701.
International Search Report for PCT/US12/66619 dated Feb. 8, 2013.

* cited by examiner

*Primary Examiner* — Alexander R Pagano
(74) *Attorney, Agent, or Firm* — Burns & Levinson, LLP; Jerry Cohen

(57) ABSTRACT

The present invention relates generally to bis-amide containing MMP inhibiting compounds, and more particularly to selectively deuterated bis-amide MMP-13 inhibiting compounds that exhibit increased stability or potency in relation to currently known MMP-13 inhibitors. Additionally, the present invention relates to methods for treating pain and inflammation in a patient comprising administering to the patient a pain-reducing effective amount of a present compound.

28 Claims, No Drawings

MATRIX METALLOPROTEINASE INHIBITORS AND METHODS FOR THE TREATMENT OF PAIN AND OTHER DISEASES

CROSS REFERENCE TO RELATED APPLICATIONS

This application is a U.S. national phase entry under 35 U.S.C. §371 of International Application No. PCT/US 12/66619, filed Nov. 27, 2012, entitled MATRIX METALLOPROTEINASE INHIBITORS AND METHODS FOR THE TREATMENT OF PAIN AND OTHER DISEASES, which in turn claims priority to and benefit of U.S. Provisional Application Ser. No. 61/713,660, filed Oct. 15, 2012, which is incorporated herein by reference in its entirety for all purposes.

FIELD OF THE INVENTION

The present invention relates generally to metalloprotease inhibiting compounds, and more particularly to selectively deuterated bis-amide MMP-13 inhibiting compounds.

BACKGROUND OF THE INVENTION

Matrix metalloproteinases (MMPs) are a family of structurally related zinc-containing enzymes that have been reported to mediate the breakdown of connective tissue in normal physiological processes such as embryonic development, reproduction, and tissue remodeling. Over-expression of MMPs or an imbalance between MMPs has been suggested as factors in inflammatory, malignant and degenerative disease processes characterized by the breakdown of extracellular matrix or connective tissues. MMPs are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis.

The mammalian MMP family has been reported to include at least 20 enzymes (*Chem. Rev.* 1999, 99, 2735-2776). Collagenase-3 (MMP-13) is among three collagenases that have been identified. Based on identification of domain structures for individual members of the MMP family, it has been determined that the catalytic domain of the MMPs contains two zinc atoms; one of these zinc atoms performs a catalytic function and is coordinated with three histidines contained within the conserved amino acid sequence of the catalytic domain. MMP-13 is over-expressed in rheumatoid arthritis, osteoarthritis, abdominal aortic aneurysm, breast carcinoma, squamous cell carcinomas of the head and neck, and vulvar squamous cell carcinoma. The principal substrates of MMP-13 are fibrillar collagens (types I, II, III) and gelatins, proteoglycans, cytokines and other components of ECM (extracellular matrix).

Matrix metalloproteinase inhibitors have been tested clinically in a few indications. Most predominantly in arthritis and cancer. Inhibitors that have entered clinical trials for an oncologic indication include prinomastat (AG3340; Agouron/Pfizer), BAY 12-9566 (Bayer Corp.), batimistat (BB-94; British Biotech, Ltd), BMS-275291 (formerly D2163; Celltech/Bristol-Myers Squibb), marimastat (BB 2516; British Biotech, Ltd./Schering-Plough) and MMI270 (B) (formerly CGS-27023A; Novartis). Many of the hydroxamic acid containing MMP inhibitors exhibit very broad toxicities in humans. For example, Marimastat, which contains a hydroxamate moiety, exhibited time-dependent and dose-dependent musculoskeletal toxicities (arthralgia, myalgia, tendinitis) in humans. Other toxicities for marimastat include ascites, disseminated carcinoma, chills, cholangitis, dizziness, dyspnea, edema, fatigue, fever, gastrointestinal (anorexia, nausea, vomiting, diarrhea, constipation), gastrointestinal hemorrhage, headache, heartburn, hepatic toxicity, hypercalcemia, hyperglycemia, rash, and shortness of breath. It is not known whether the toxicities exhibited by many of the MMP inhibitors are attributed to the hydroxamic acid moiety, however, it is clear that having an MMP inhibitor that does not contain a hydroxamic acid group or bind zinc could reduce many potential metabolic liabilities. One of the few non-hydroxamic acid containing compounds that binds allostericically to MMP-13 and does not bind zinc are a series of bis-amide pyrimidine compounds disclosed in WO 02/064571, WO 03/049738, WO 04/041788 and WO 04/060883. All of the bis-amide pyrimidines represented in WO 02/064571, WO 03/049738, WO 04/041788 and WO 04/060883 form the bis-amide attachments via two primary benzylic amines having no carbon substitution on the benzylic carbon atoms. WO 07/079199 discloses that substitution of one of the benzylic hydrogens on at least one of the benzyl carbons forming the bis-amide pyrimidines with a methyl group results in an enhancement of the microsomal stability in Rat and/or Human microsomes. This implies that there may be some cytochrome P450 induced transformation that may be occurring at the benzylic carbon. One possible transformation is the P450 induced oxidative dealkylation of the benzylic carbon to give a resulting benzaldehyde (Illey, J.; Tolando, R.; Constantino, L. *J. Chem. Soc., Perkin Trans. 2*, 1299-1305, (2001)). One consequence of placing a methyl group on the benzylic position is that it transforms the achiral compound (i.e., a molecule that has a plane of symmetry) into a molecule that is chiral (i.e., a molecule that has a non-superposable mirror image) having both an R- and S-configuration. WO 07/079199 also discloses that the spatial orientation of the substituted methyl group can have a profound effect on the inhibitory activity of the molecule. WO07/079199 discloses that positioning the substituted methyl group in the "R" configuration produces a molecule that is much less potent than the same molecule with the methyl group positioned in the "S" configuration. In some cases differences in IC50 are observed of more than a factor of ten when the chirality of the substituted methyl group changes from an "R" to an "S" configuration. Engel & Co-workers (Engel, C. K. et al. *Chemistry & Biology*, Vol. 12, 181-189, (2005)) disclose the x-ray crystal structure of three separate symmetrical bis-amide pyrimidine MMP-13 inhibitors and show that they bind to an allosteric site known as the S1' side pocket. Clearly, the methyl group in the benzylic position with the less active, "R" configuration must be interacting negatively within this S1' side pocket. In fact, x-ray and molecular modelling analysis of a bis-amide pyrimidine inhibitor within the S1' side pocket of MMP-13 by Pirard (Pirard, B.; *Drug Discovery Today*, 12, No. 15/16, (2007)) shows very little extra space around the benzylic carbon. The result of having to synthesize a molecule with a methyl or other alkyl group oriented in the more active "S" enantiomeric configuration is that a much longer & laborious synthetic scheme must be devised and executed. Another problem with turning the bis-amide pyrimidine into a chiral molecule is that now one has the added problem of the possibility that the chiral center might racemize while the compound is in storage and/or when administered in-vivo. It would be of benefit if one could reduce the level of microsomal instability that is observed at the benzylic carbon position without resulting in the creation of a chiral molecule. One possible answer is to replace the hydrogens from one or both benzylic carbons with deuterium atoms and hence avoid creating a chiral center. Such deuterium substitution could inhibit P450 induced transformations at the benzylic carbon while still maintaining the molecule's potency for inhibiting MMP-13.

Kushner and coworkers (Kushner, D. J.; Baker, A.; Dunstall, T. G. Can J. Physiol Pharmacol, 77(2), (1999) p. 79-88) have presented examples of how incorporating deuterium into a drug can often reduce the level of metabolic induced transformations especially those mediated by Cytochrome P450. This reduce rate of Cytochrome P450 induce metabolism can sometimes translate directly to enhanced bioavailability. The reason for this is due to the fact that atomic substitution of a hydrogen by a deuterium in a drug alters the strength of the carbon-deuterium bond of the drug, while keeping it's 3D surface very similar to that of the nondeuterated version. Substitution of deuterium for hydrogen, can give rise to an isotope effect that can alter the pharmacokinetics of the drug. In a reaction in which the cleavage of a C—H bond is rate determining the same reaction of the C-D analogue will be reduced. For example Schneider and coworkers (Scheneider, F.; et al., BiRDS Pharma GmbH, Arzneimittel Forschung (2006), 56(4), p. 295-300) have shown that replacing several of the hydrogen atoms around one of the aromatic rings of the COX-2 inhibitor Refecoxib (4-(4-methylsulfonylphenyl)-3-phenyl-5H-furan-2-one) with deuterium (at positions 2',3',4',5' an 6') enhanced the microsomal stability and oral bioavailability of the drug without affecting it's COX-2 selectivity. If one applied this strategy to one or more of the benzyl positions of the bis-amide pyrimidine one could reduce its susceptibility to cytochrome P-450 hydroxylation and ultimately enhance its overall bioavailability and possibly it's target tissue compound concentration.

Another possible affect of incorporating deuterium into a drug is on its polymorphic (i.e., different crystalline forms) properties. For example, Hirota and Urushibara (Bulletin of the Chemical Society of Japan, 32(7), (1959), 703-706) have shown that replacing a single vinylic hydrogen for deuterium on Allocinnamic acid can change both the melting point and the intensity of the x-ray diffraction pattern of the molecule. Lin and Guillory (Journal of Pharmaceutical Science, Vol. 59(7), (2006), 972-979) have shown that sulfanilamide-d4 exhibited smaller heats of transition and heats of fusion for its various crystalline states as compared to it's corresponding non-deuterated forms. Finally, Crawford and co-workers (Crawford, S. et al., Angewandte Chemie International Edition, 48(4), (2009), 755-757) recently showed that the crystalline form of fully deuterated pyridine adopts a unique configuration that can only be obtained under high pressure with the non-deuterated parent. Their work clearly showed that replacing hydrogen for deuterium changes the strength of interaction between various atoms in neighboring molecules causing a change in the crystalline arrangement to one that is more energetically favorable. This change in crystalline arrangement or polymorph may allow for improved dissolution properties and enhanced bioavailability.

This invention discloses MMP inhibitors and specifically inhibitors of MMP-13 with surprising and unexpected improvements in their properties when bearing two or more deuterium atoms at positions $R^1$, $R^2$, $R^3$ and/or $R^4$ in the compounds of Formula (I) and (II). The unexpected advantages observed for the deuterium substituted compounds of this invention include improvements in microsomal stability, pharmacokinetics (PK), cell viability and/or enhanced dissolution characteristics. It is believed that these new findings and the specific structural modifications which this invention discloses will lead to inhibitors of MMP-13 with improved pharmaceutical value.

SUMMARY OF THE INVENTION

The present invention relates to a new class of substituted bis-amide containing pharmaceutical agents. In particular, the present invention provides a new class of MMP-13 inhibiting compounds containing a pyrimidinyl bis-amide group in combination with a deuterium substituted moiety that exhibit potent MMP-13 inhibiting activity and are highly selective toward MMP-13 compared to currently known MMP inhibitors.

The present invention provides a new class of substituted bis-amide MMP-13 inhibiting compounds that are represented by the general Formula (I):

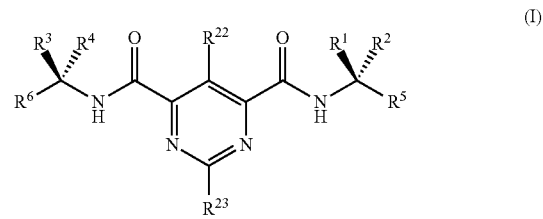

(I)

wherein:

$R^5$ and $R^6$ are independently selected from the group consisting of alkyl, alkenyl, alkynyl, cycloalkyl, heterocyclyl, aryl, and heteroaryl, wherein alkyl, alkenyl, alkynyl, cycloalkyl, heterocyclyl, aryl, and heteroaryl are optionally substituted one or more times and wherein two substituents in the cycloalkyl-, aryl-, or heteroarylring when taken together with the nitrogen or carbon to which they are attached optionally complete an additional 3- to 8-membered ring containing carbon atoms and optionally containing one or more heteroatoms selected from O, $SO_x$, or $NR^{50}$ and which is optionally substituted or partially saturated;

$R^1$, $R^2$, $R^3$, $R^4$ are independently selected from the group consisting of hydrogen, deuterium, alkyl, deuteroalkyl, $CD_3$, haloalkyl, fluoroalkyl, cycloalkyl, alkenyl, alkynyl, aryl, heteroaryl, cycloalkyl-alkyl, arylalkyl, heteroarylalkyl, $COOR^{10}$, $CONR^{10}R^{11}$, $SO_2R^{10}$ and $SO_2NR^{10}R^{11}$ wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times;

$R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{22}$ and $R^{23}$ are independently selected from the group consisting of hydrogen, deuterium, halo, alkyl, deuteroalkyl, $CD_3$, cycloalkyl, hydroxy, alkoxy, aryl, heteroaryl, arylalkyl, heteroarylalkyl, alkenyl, alkynyl, $NO_2$, $NR^{10}R^{11}$, $NR^{10}NR^{10}R^{11}$, $NR^{10}N=CR^{10}R^{11}$, $NR^{10}SO_2R^{11}$, CN, $COOR^{10}$, and fluoroalkyl, wherein alkyl, cycloalkyl, alkoxy, alkenyl, alkynyl, and fluoroalkyl are optionally substituted;

$R^{50}$ is selected from the group consisting of hydrogen, deuterium, deuteroalkyl, $CD_3$, alkyl, aryl, heteroaryl, $C(O)R^{10}$, $C(O)NR^{10}R^{11}$, $SO_2R^{10}$ and $SO_2NR^{10}R^{11}$, wherein alkyl, aryl, and heteroaryl are optionally substituted;

x is selected from 0 to 2; or

N-oxides, pharmaceutically acceptable salts, prodrugs, formulations, polymorphs, tautomers, racemic mixtures, optically active enantiomers, diastereoisomers or stereoisomers thereof.

Additionally, the present invention provides a new class of substituted bis-amide MMP-13 inhibiting compounds that are represented general Formula (II):

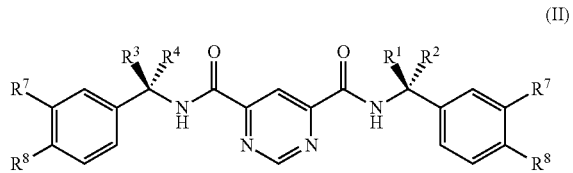

(II)

wherein:

$R^7$ and $R^8$ are independently selected from the group consisting of hydrogen, deuterium, halo, alkyl, deuteroalkyl, $CD_3$, $CD_3O$, cycloalkyl, hydroxy, alkoxy, aryl, heteroaryl, arylalkyl, heteroarylalkyl, alkenyl, tetrazole, alkynyl, $NO_2$, $NR^{10}R^{11}$, $NR^{10}NR^{10}R^{11}$, $NR^{10}N=CR^{10}R^{11}$, $NR^{10}SO_2R^{11}$, CN, $COOR^{10}$, $CONR^{10}R^{11}$, $SO_2NR^{10}R^{11}$, $SO_2R^{10}$, $OC(O)R^{10}$, $OC(O)NR^{10}R^{11}$, $NR^{10}C(O)R^{11}$, $NR^{10}CO_2R^{11}$, $(C_0\text{-}C_6)\text{-alkyl-}C(=NR^a)NHR^b$, $(C_0\text{-}C_6)\text{-alkyl-NHC}(=NR^a)NHR^b$, $(C_0\text{-}C_6)\text{-alkyl-}C(O)OR^{10}$, $(C_0\text{-}C_6)\text{-alkyl-}C(O)NR^{10}R^{11}$, $(C_0\text{-}C_6)\text{-alkyl-}C(O)\text{—NH—CN}$, $O\text{—}(C_0\text{-}C_6)\text{-alkyl-}C(O)NR^{10}R^{11}$, $S(O)_x\text{—}(C_0\text{-}C_6)\text{-alkyl-}C(O)OR^{10}$, $S(O)_x\text{—}(C_0\text{-}C_6)\text{-alkyl-}C(O)NR^{10}R^{11}$, $(C_0\text{-}C_6)\text{-alkyl-}C(O)NR^{10}\text{—}(C_0\text{-}C_6)\text{-alkyl-NR}^{10}R^{11}$, $(C_0\text{-}C_6)\text{-alkyl-NR}^{10}R^{11}$, $(C_0\text{-}C_6)\text{-alkyl-NR}^{10}\text{—}C(O)R^{10}$, $(C_0\text{-}C_6)\text{-alkyl-NR}^{10}\text{—}C(O)OR^{10}$, $(C_0\text{-}C_6)\text{-alkyl-NR}^{10}\text{—}C(O)\text{—}NR^{10}R^{11}$, $(C_0\text{-}C_6)\text{-alkyl-NR}^{10}\text{—}SO_2NR^{10}R^{11}$, and fluoroalkyl, wherein alkyl, cycloalkyl, alkoxy, alkenyl, alkynyl, and fluoroalkyl are optionally substituted;

$R^7$ and $R^8$ when taken together with the aryl ring to which they are attached may complete a 3- to 8-membered ring containing carbon atoms and optionally containing a heteroatom selected from O, S, or $NR^{50}$ and which is optionally substituted;

$R^1$, $R^2$, $R^3$, $R^4$ are independently selected from the group consisting of hydrogen, and deuterium, alkyl, deuteroalkyl, $CD_3$, haloalkyl, fluoroalkyl, cycloalkyl, alkenyl, alkynyl, aryl, heteroaryl, cycloalkyl-alkyl, arylalkyl, heteroarylalkyl, $COOR^{10}$, $CONR^{10}R^{11}$, $SO_2R^{10}$ and $SO_2NR^{10}R^{11}$ wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times;

$R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{50}$ is selected from the group consisting of hydrogen, deuterium, deuteroalkyl, $CD_3$, alkyl, aryl, heteroaryl, $C(O)R^{10}$, $C(O)NR^{10}R^{11}$, $SO_2R^{10}$ and $SO_2NR^{10}R^{11}$, wherein alkyl, aryl, and heteroaryl are optionally substituted;

x is selected from 0 to 2; or

N-oxides, pharmaceutically acceptable salts, prodrugs, formulations, polymorphs, tautomers, racemic mixtures, optically active enantiomers, diastereoisomers or stereoisomers thereof.

The substituted bis-amide MMP-13 inhibiting compounds of the present invention may be used in the treatment of MMP-13 mediated osteoarthritis and may be used for other MMP-13 mediated symptoms, inflammatory, malignant and degenerative diseases characterized by excessive extracellular matrix degradation and/or remodeling, such as cancer, and chronic inflammatory diseases such as arthritis, rheumatoid arthritis, osteoarthritis atherosclerosis, abdominal aortic aneurysm, inflammation, pain, inflammatory pain, bone pain, joint pain, multiple sclerosis, and chronic obstructive pulmonary disease.

The present invention also provides substituted bis-amide MMP-13 inhibiting compounds that are useful as active ingredients in pharmaceutical compositions for treatment or prevention of MMP-13 mediated diseases. The present invention also contemplates use of such compounds in pharmaceutical compositions for oral or parenteral administration, comprising one or more of the substituted bis-amide MMP-13 inhibiting compounds disclosed herein.

The present invention further provides methods of inhibiting MMP-13, by administering including, but not limited to, oral, intraarticular, transdermal or parenteral formulations comprising the substituted bis-amide MMP-13 inhibiting compounds by standard methods known in medical practice, for the treatment of diseases or symptoms arising from or associated with MMP-13, including prophylactic and therapeutic treatment.

The substituted bis-amide MMP-13 inhibiting compounds of the present invention may be used in combination with viscosupplements such as hyaluronic acids such as Synvisc-one and/or Synvisc, a disease modifying antirheumatic drug, a nonsteroidal anti-inflammatory drug, a COX-2 selective inhibitor, a COX-1 inhibitor, an immunosuppressive, a steroid, a biological response modifier or other anti-inflammatory agents or therapeutics useful for the treatment of chemokine mediated diseases.

DETAILED DESCRIPTION OF THE INVENTION

The term "D" as used herein alone or as part of a chemical structure or group, denotes deuterium.

The term "deutero" as used herein alone or as part of a group, denote optionally substituted deuterium atoms.

The term "deuterium" as used herein refers to one of two stable isotopes of hydrogen wherein the nucleus contains one neutron and one proton.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "cycloalkyl", as used herein alone or as part of another group, denotes optionally substituted, saturated cyclic hydrocarbon ring systems, including bridged ring systems, desirably containing 1 to 3 rings and 3 to 9 carbons per ring. Exemplary unsubstituted such groups include, but are not limited to, cyclopropyl, cyclobutyl, cyclopentyl, cyclohexyl, cycloheptyl, cyclooctyl, cyclodecyl, cyclododecyl, and adamantyl. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from the group consisting of N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, morpholino, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The term "amino" denotes the radical —NH$_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "isotopic enrichment" refers to a process by which the relative abundance of an isotope of a given element are altered, thus producing a form of the element that has been enriched in one particular isotope and depleted in its other isotopic forms. Thus, the invention encompasses all percent levels of isotopic enrichment of compounds of Formulas (I) and (II). Exemplary percent levels of isotopic enrichment for deuterium include, but are not limited to, ≥97%, ≥95%, ≥85%, ≥50%, ≥30%, ≥20%, ≥5% & ≥1%.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts include deuterated organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences*, 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations. Compounds having hydrogens replaced by deuterium may form polymorphs which may enhance their solubility and/or bioavailability properties.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

The term "S" as used herein alone or as part of a chemical structure designates the absolute configuration of one of two possible enantiomers of a chiral compound. To name the enantiomers unambiguously, the "handedness" of the molecule must be indicated. "Right hand" and "left hand" nomenclature was originated by R. S. Cahn, C. Ingold, and V. Prelog.

The term "R" as used herein alone or as part of a chemical structure designates the absolute configuration of one of two possible enantiomers of a chiral compound. To name the enantiomers unambiguously, the "handedness" of the molecule must be indicated. "Right hand" and "left hand" nomenclature was originated by R. S. Cahn, C. Ingold, and V. Prelog.

The term "racemic mixture" denotes a mixture that is about 50% of one enantiomer and about 50% of the corresponding enantiomer relative to all chiral centers in the molecule. Thus, the invention encompasses all enantiomerically-pure, enantiomerically-enriched, and racemic mixtures of compounds of Formulas (I) and (II).

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, N.Y., 1962); Wilen, S. H., Tables of Resolving Agents and Optical Resolutions p. 268 (E. L. Eliel, Ed., Univ. of Notre Dame Press, Notre Dame, Ind., 1972); Stereochemistry of Organic Compounds, Ernest L. Eliel, Samuel H. Wilen and Lewis N. Manda (1994 John Wiley & Sons, Inc.), and Stereoselective Synthesis A Practical Approach, Mihaly Nogradi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;

OC(S)NH—(C$_1$-C$_4$ alkyl);
OC(S)N(C$_1$-C$_4$ alkyl)$_2$;
SH;
S—(C$_1$-C$_4$ alkyl);
S(O)—(C$_1$-C$_4$ alkyl);
S(O)$_2$—(C$_1$-C$_4$ alkyl);
SC(O)—(C$_1$-C$_4$ alkyl);
SC(O)O—(C$_1$-C$_4$ alkyl);
NH$_2$;
N(H)—(C$_1$-C$_4$ alkyl);
N(C$_1$-C$_4$ alkyl)$_2$;
N(H)C(O)—(C$_1$-C$_4$ alkyl);
N(CH$_3$)C(O)—(C$_1$-C$_4$ alkyl);
N(H)C(O)—CF$_3$;
N(CH$_3$)C(O)—CF$_3$;
N(H)C(S)—(C$_1$-C$_4$ alkyl);
N(CH$_3$)C(S)—(C$_1$-C$_4$ alkyl);
N(H)S(O)$_2$—(C$_1$-C$_4$ alkyl);
N(H)C(O)NH$_2$;
N(H)C(O)NH—(C$_1$-C$_4$ alkyl);
N(CH$_3$)C(O)NH—(C$_1$-C$_4$ alkyl);
N(H)C(O)N(C$_1$-C$_4$ alkyl)$_2$;
N(CH$_3$)C(O)N(C$_1$-C$_4$ alkyl)$_2$;
N(H)S(O)$_2$NH$_2$;
N(H)S(O)$_2$NH—(C$_1$-C$_4$ alkyl);
N(CH$_3$)S(O)$_2$NH—(C$_1$-C$_4$ alkyl);
N(H)S(O)$_2$N(C$_1$-C$_4$ alkyl)$_2$;
N(CH$_3$)S(O)$_2$N(C$_1$-C$_4$ alkyl)$_2$;
N(H)C(O)O—(C$_1$-C$_4$ alkyl);
N(CH$_3$)C(O)O—(C$_1$-C$_4$ alkyl);
N(H)S(O)$_2$O—(C$_1$-C$_4$ alkyl);
N(CH$_3$)S(O)$_2$O—(C$_1$-C$_4$ alkyl);
N(CH$_3$)C(S)NH—(C$_1$-C$_4$ alkyl);
N(CH$_3$)C(S)N(C$_1$-C$_4$ alkyl)$_2$;
N(CH$_3$)C(S)O—(C$_1$-C$_4$ alkyl);
N(H)C(S)NH$_2$;
NO$_2$;
CO$_2$H;
CO$_2$—(C$_1$-C$_4$ alkyl);
C(O)N(H)OH;
C(O)N(CH$_3$)OH:
C(O)N(CH$_3$)OH;
C(O)N(CH$_3$)O—(C$_1$-C$_4$ alkyl);
C(O)N(H)—(C$_1$-C$_4$ alkyl);
C(O)N(C$_1$-C$_4$ alkyl)$_2$;
C(S)N(H)—(C$_1$-C$_4$ alkyl);
C(S)N(C$_1$-C$_4$ alkyl)$_2$;
C(NH)N(H)—(C$_1$-C$_4$ alkyl);
C(NH)N(C$_1$-C$_4$ alkyl)$_2$;
C(NCH$_3$)N(H)—(C$_1$-C$_4$ alkyl);
C(NCH$_3$)N(C$_1$-C$_4$ alkyl)$_2$;
C(O)—(C$_1$-C$_4$ alkyl);
C(NH)—(C$_1$-C$_4$ alkyl);
C(NCH$_3$)—(C$_1$-C$_4$ alkyl);
C(NOH)—(C$_1$-C$_4$ alkyl);
C(NOCH$_3$)—(C$_1$-C$_4$ alkyl);
CN;
CHO;
CH$_2$OH;
CH$_2$O—(C$_1$-C$_4$ alkyl);
CH$_2$NH$_2$;
CH$_2$N(H)—(C$_1$-C$_4$ alkyl);
CH$_2$N(C$_1$-C$_4$ alkyl)$_2$;
aryl;
heteroaryl;
cycloalkyl; and
heterocyclyl.

In some embodiments of the present invention, the substituted bis-amide MMP-13 inhibiting compounds are represented by the general Formula (I):

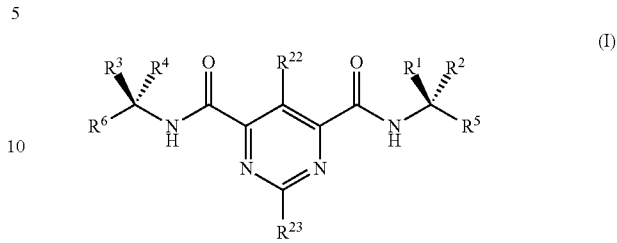

wherein:
R$^5$ and R$^6$ are independently selected from the group consisting of alkyl, alkenyl, alkynyl, cycloalkyl, heterocyclyl, aryl, and heteroaryl, wherein alkyl, alkenyl, alkynyl, cycloalkyl, heterocyclyl, aryl, and heteroaryl are optionally substituted one or more times and wherein two substituents in the cycloalkyl-, aryl-, or heteroaryl ring when taken together with the nitrogen or carbon to which they are attached optionally complete an additional 3- to 8-membered ring containing carbon atoms and optionally containing one or more heteroatoms selected from O, SO$_x$, or NR$^{50}$ and which is optionally substituted or partially saturated;

R$^1$, R$^2$, R$^3$, R$^4$ are independently selected from the group consisting of hydrogen, deuterium, alkyl, deuteroalkyl, CD$_3$, haloalkyl, fluoroalkyl, cycloalkyl, alkenyl, alkynyl, aryl, heteroaryl, cycloalkyl-alkyl, arylalkyl, heteroarylalkyl, COOR$^{10}$, CONR$^{10}$R$^{11}$, SO$_2$R$^{10}$ and SO$_2$NR$^{10}$R$^{11}$ wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times;

R$^{10}$ and R$^{11}$ are independently selected from the group consisting of hydrogen, deuterium, alkyl, deuteroalkyl, CD$_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or R$^{10}$ and R$^{11}$ when taken together with the nitrogen to which they are attached complete a 3- to 8-membered ring containing carbon atoms and optionally containing a heteroatom selected from O, S, or NR$^{50}$ and which is optionally substituted;

R$^{22}$ and R$^{23}$ are independently selected from the group consisting of hydrogen, deuterium, halo, alkyl, deuteroalkyl, CD$_3$, cycloalkyl, hydroxy, alkoxy, aryl, heteroaryl, arylalkyl, heteroarylalkyl, alkenyl, alkynyl, NO$_2$, NR$^{10}$R$^{11}$, NR$^{10}$NR$^{10}$R$^{11}$, NR$^{10}$N=CR$^{10}$R$^{11}$, NR$^{10}$SO$_2$R$^{11}$, CN, COOR$^{10}$, and fluoroalkyl, wherein alkyl, cycloalkyl, alkoxy, alkenyl, alkynyl, and fluoroalkyl are optionally substituted;

R$^{50}$ is selected from the group consisting of hydrogen, deuterium, deuteroalkyl, CD$_3$, alkyl, aryl, heteroaryl, C(O)R$^{10}$, C(O)NR$^{10}$R$^{11}$, SO$_2$R$^{10}$ and SO$_2$NR$^{10}$R$^{11}$, wherein alkyl, aryl, and heteroaryl are optionally substituted;

x is selected from 0 to 2; or

N-oxides, pharmaceutically acceptable salts, prodrugs, formulations, polymorphs, tautomers, racemic mixtures, optically active enantiomers, diastereoisomers or stereoisomers thereof.

Additionally, the present invention provides a new class of substituted bis-amide MMP-13 inhibiting compounds that are represented general Formula (II):

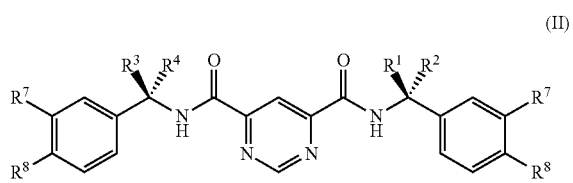

(II)

wherein:

R[7] and R[8] are independently selected from the group consisting of hydrogen, deuterium, halo, alkyl, deuteroalkyl, $CD_3$, $CD_3O$, cycloalkyl, hydroxy, alkoxy, aryl, heteroaryl, arylalkyl, heteroarylalkyl, alkenyl, tetrazole, alkynyl, $NO_2$, $NR^{10}R^{11}$, $NR^{10}NR^{10}R^{11}$, $NR^{10}N=CR^{10}R^{11}$, $NR^{10}SO_2R^{11}$, CN, $COOR^{10}$, $CONR^{10}R^{11}$, $SO_2NR^{10}R^{11}$, $SO_2R^{10}$, $OC(O)R^{10}$, $OC(O)NR^{10}R^{11}$, $NR^{10}C(O)R^{11}$, $NR^{10}CO_2R^{11}$, $(C_0\text{-}C_6)$-alkyl-$C(=NR^a)NHR^b$, $(C_0\text{-}C_6)$-alkyl-$NHC(=NR^a)NHR^b$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)$—NH—CN, O—$(C_0\text{-}C_6)$-alkyl-$C(O)NR^{10}R^{11}$, $S(O)_x$—$(C_0\text{-}C_6)$-alkyl-$C(O)OR^{10}$, $S(O)_x$—$(C_0\text{-}C_6)$-alkyl-$C(O)NR^{10}R^{11}$, $(C_0\text{-}C_6)$-alkyl-$C(O)NR^{10}$—$(C_0\text{-}C_6)$-alkyl-$NR^{10}R^{11}$, $(C_0\text{-}C_6)$-alkyl-$NR^{10}R^{11}$, $(C_0\text{-}C_6)$-alkyl-$NR^{10}$—$C(O)R^{10}$, $(C_0\text{-}C_6)$-alkyl-$NR^{10}$—$C(O)OR^{10}$, $(C_0\text{-}C_6)$-alkyl-$NR^{10}$—$C(O)$—$NR^{10}R^{11}$, $(C_0\text{-}C_6)$-alkyl-$NR^{10}$—$SO_2NR^{10}R^{11}$, and fluoroalkyl, wherein alkyl, cycloalkyl, alkoxy, alkenyl, alkynyl, and fluoroalkyl are optionally substituted;

R[7] and R[8] when taken together with the aryl ring to which they are attached may complete a 3- to 8-membered ring containing carbon atoms and optionally containing a heteroatom selected from O, S, or $NR^{50}$ and which is optionally substituted;

R[1], R[2], R[3], R[4] are independently selected from the group consisting of hydrogen, and deuterium, alkyl, deuteroalkyl, $CD_3$, haloalkyl, fluoroalkyl, cycloalkyl, alkenyl, alkynyl, aryl, heteroaryl, cycloalkyl-alkyl, arylalkyl, heteroarylalkyl, $COOR^{10}$, $CONR^{10}R^{11}$, $SO_2R^{10}$ and $SO_2NR^{10}R^{11}$ wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times;

R[10] and R[11] are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or R[10] and R[11] when taken together with the nitrogen to which they are attached complete a 3- to 8-membered ring containing carbon atoms and optionally containing a heteroatom selected from O, S, or $NR^{50}$ and which is optionally substituted;

R[50] is selected from the group consisting of hydrogen, deuterium, deuteroalkyl, $CD_3$, alkyl, aryl, heteroaryl, $C(O)R^{10}$, $C(O)NR^{10}R^{11}$, $SO_2R^{10}$ and $SO_2NR^{10}R^{11}$, wherein alkyl, aryl, and heteroaryl are optionally substituted;

x is selected from 0 to 2; or

N-oxides, pharmaceutically acceptable salts, prodrugs, formulations, polymorphs, tautomers, racemic mixtures, optically active enantiomers, diastereoisomers or stereoisomers thereof.

More specifically, the compounds of Formula (II) may be selected from, but are not limited to, the following:

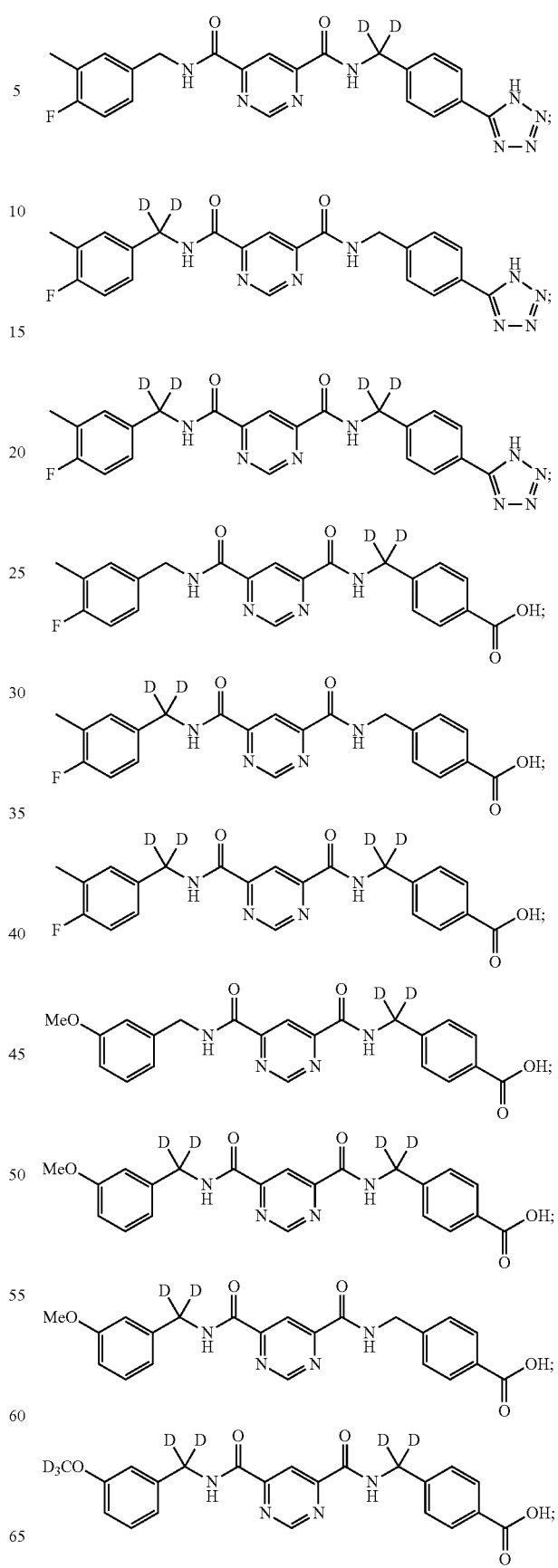

-continued
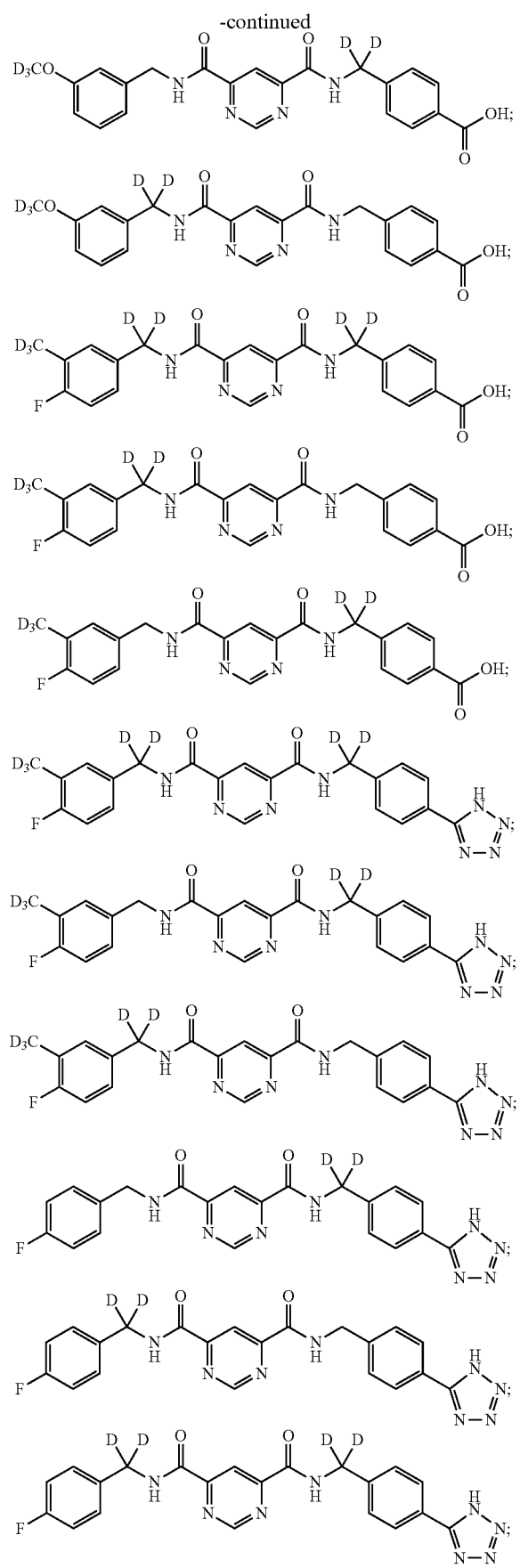
-continued
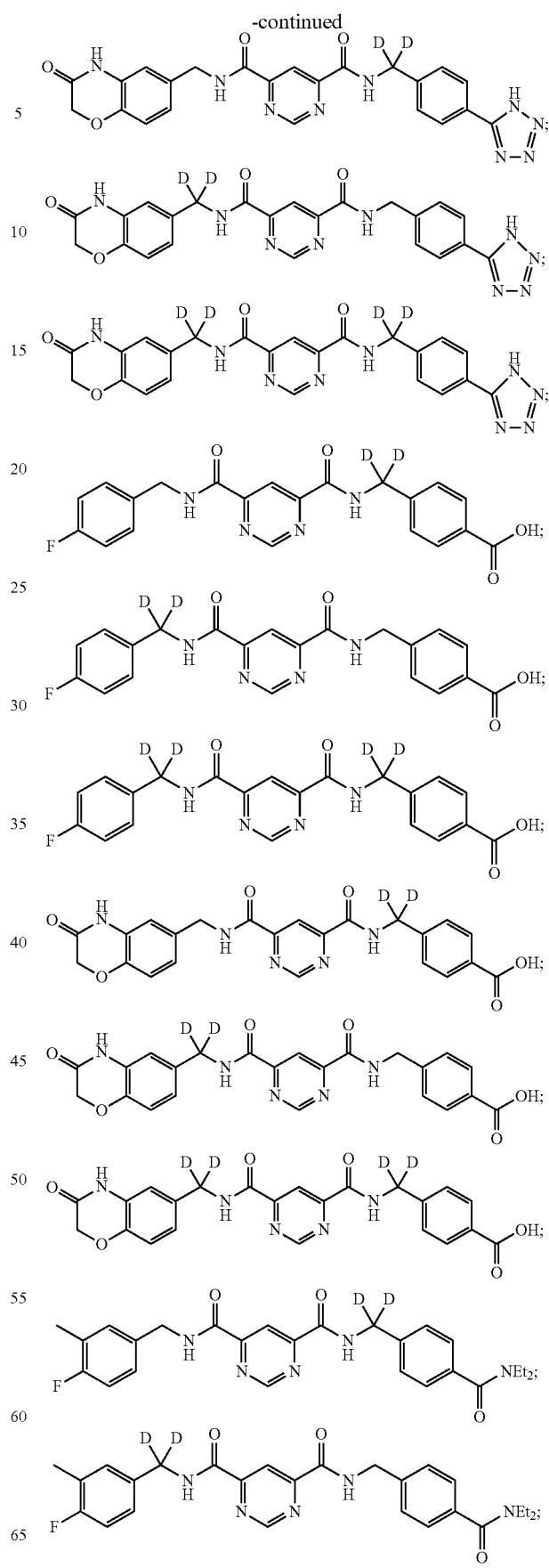

-continued
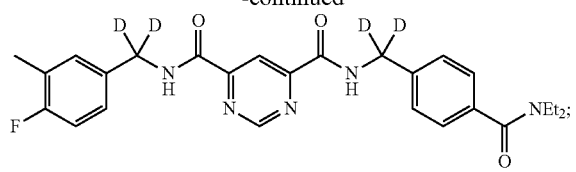
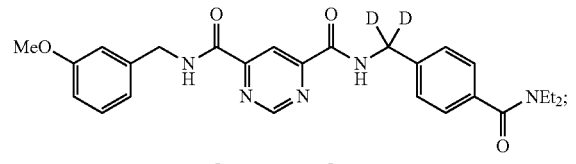
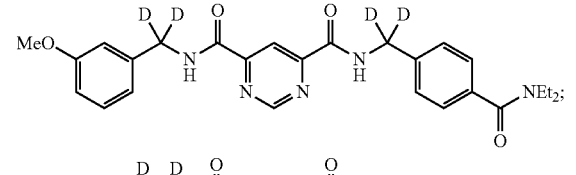
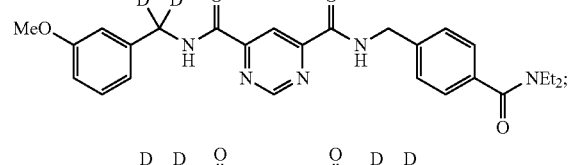
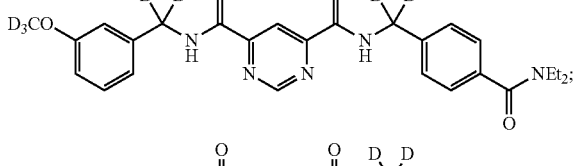
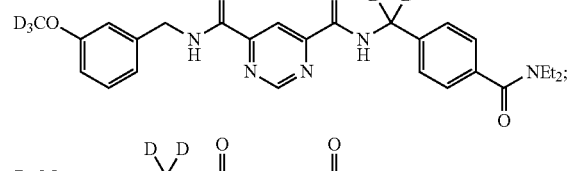
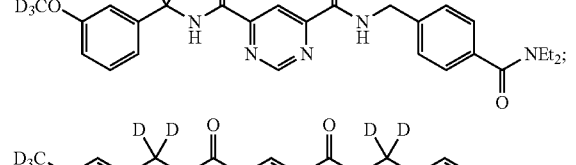
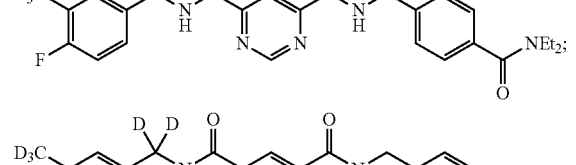
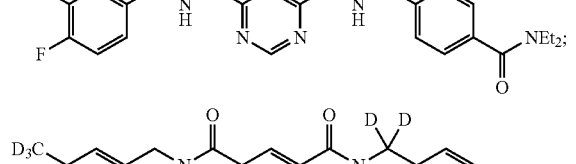
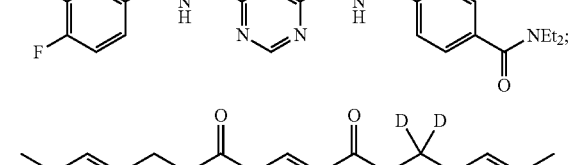
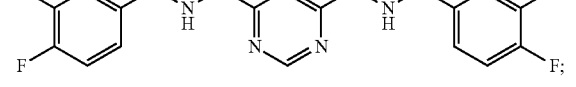
-continued
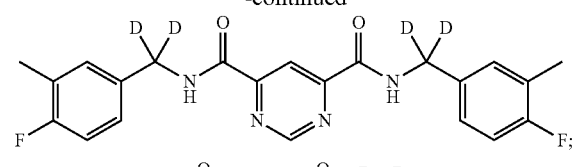
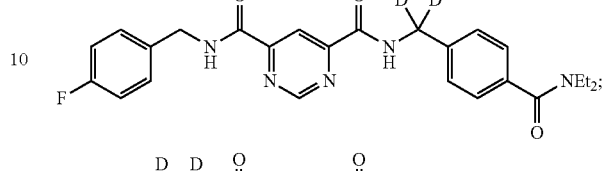
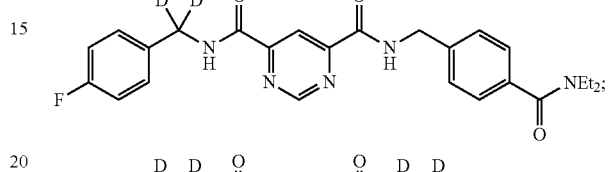
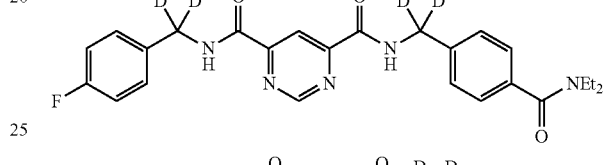
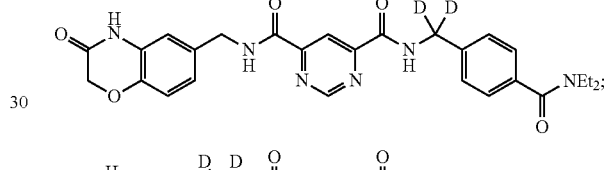
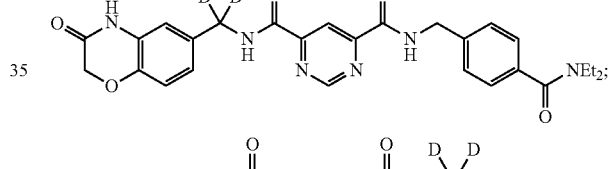
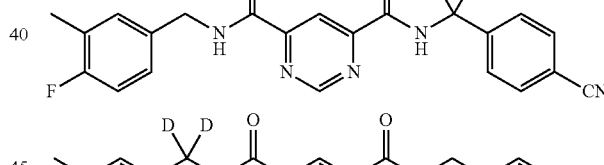
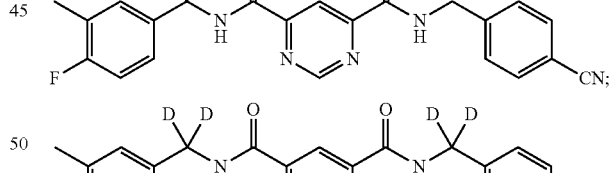
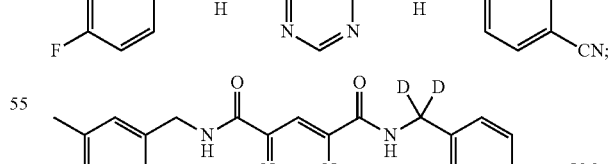
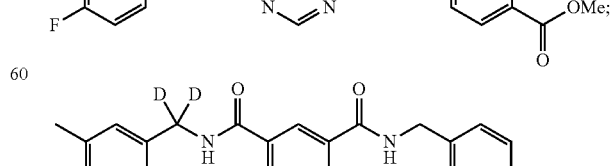
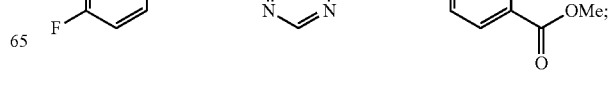

-continued

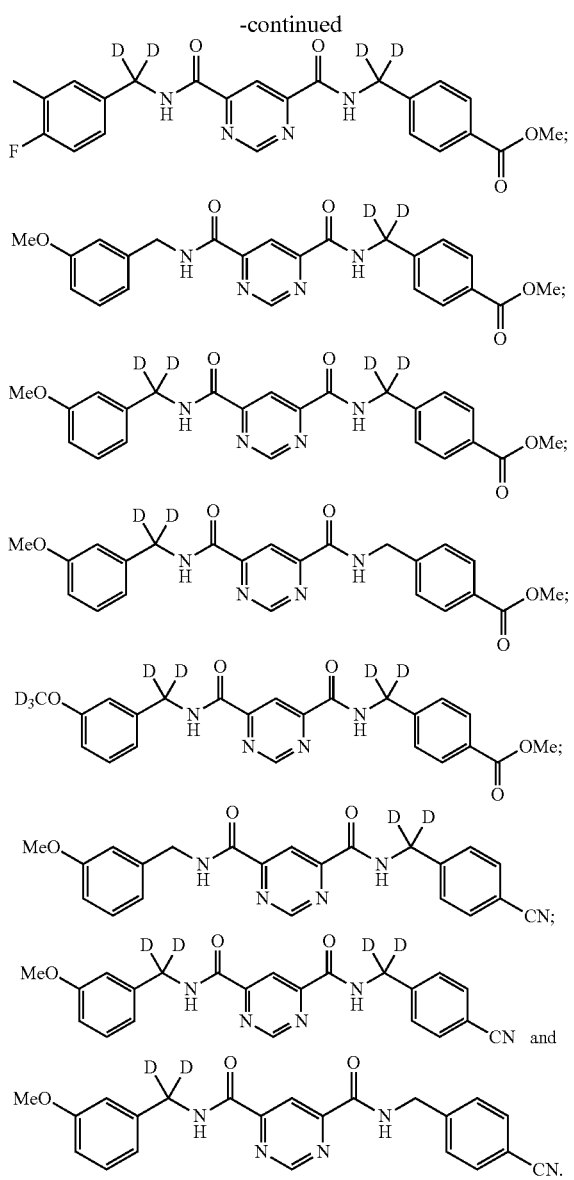

It is contemplated that the compounds of the present invention represented by the Formula described above include all diastereomers and enantiomers, as well as racemic mixtures as well as polymorphs. Racemic mixtures may be separated by chiral salt resolution or by chiral column HPLC chromatography.

In accordance therewith, some embodiments of the present invention provide a pharmaceutical composition which may include an effective amount of a partially deuterated bis-amide MMP-13 inhibiting compound of the present invention and a pharmaceutically acceptable carrier.

The present invention also is directed to methods of inhibiting MMP-13 and methods of treating diseases or symptoms mediated by an MMP-13 enzyme. Such methods include administering a substituted bis-amide MMP-13 inhibiting compound of the present invention, such as a compound of Formula (I), as defined above, or a pharmaceutically acceptable salt thereof. Examples of diseases or symptoms mediated by an MMP-13 enzyme include, but are not limited to, rheumatoid arthritis, osteoarthritis, abdominal aortic aneurysm, cancer, inflammation, atherosclerosis, multiple sclerosis, chronic obstructive pulmonary disease, ocular diseases, neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory, pain, inflammatory pain, bone pain, joint pain and fibrotic syndromes, intestinal bowel syndrome, allergies, Alzheimers disease, arterial plaque formation, viral infection, stroke, atherosclerosis, cardiovascular disease, reperfusion injury, trauma, chemical exposure or oxidative damage to tissues.

In some embodiments of the present invention, the partially deuterated bis-amide MMP-13 inhibiting compounds defined above are used in the manufacture of a medicament for the treatment of a disease mediated by an MMP-13 enzyme.

In some embodiments, the partially deuterated bis-amide MMP-13 inhibiting compounds defined above may be used in combination with a drug, agent or therapeutic such as, but not limited to: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) other anti-inflammatory agents or therapeutics useful for the treatment of chemokine mediated diseases or (i) a viscosupplement.

Examples of disease modifying antirheumatic drugs include, but are not limited to, methotrexate, azathioptrineluflunomide, penicillamine, gold salts, mycophenolate, mofetil and cyclophosphamide.

Examples of nonsteroidal anitinflammatory drugs include, but are not limited to, piroxicam, ketoprofen, naproxen, indomethacin, and ibuprofen.

Examples of COX-2 selective inhibitors include, but are not limited to, rofecoxib, celecoxib, and valdecoxib.

An example of a COX-1 inhibitor includes, but is not limited to, piroxicam.

Examples of immunosuppressives include, but are not limited to, methotrexate, cyclosporin, leflunimide, tacrolimus, rapamycin and sulfasalazine.

Examples of steroids include, but are not limited to, p-methasone, prednisone, cortisone, prednisolone and dexamethasone.

Examples of biological response modifiers include, but are not limited to, anti-TNF antibodies, TNF-α antagonists, IL-1 antagonists, anti-CD40, anti-CD28, IL-10 and anti-adhesion molecules.

Examples of anti-inflammatory agents or therapeutics include, but are not limited to, p38 kinase inhibitors, PDE4 inhibitors, TACE inhibitors, chemokine receptor antagonists, thalidomide, leukotriene inhibitors and other small molecule inhibitors of pro-inflammatory cytokine production.

Examples of viscosupplement include, but are not limited to, various molecular weight hyaluronic acids, Synvisc-one and Synvisc.

In accordance with another embodiment of the present invention, a pharmaceutical composition may include an effective amount of a compound of the present invention, a pharmaceutically acceptable carrier and a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) other anti-inflammatory agents or therapeutics useful for the treatment of chemokine mediated diseases or (i) a viscosupplement.

Standard in vitro assays for measuring human and rat microsomal stability is presented in Example 150. A standard in vivo method for measuring oral bioavailability in the rat is presented in Example 170. The in vivo pain inhibiting properties of the MMP inhibiting compounds of the present invention may be measured using any suitable animal model known in the art. A standard in vivo test for measuring inflammatory pain is described in Example 200 & a standard in vivo test for measuring OA pain and inflammation is described in Example 201. The MMP inhibiting activity of the bis-amide MMP inhibiting compounds of the present invention may be measured using any suitable assay known in the art. Standard in vitro assays for measuring MMP-1, 2, 3, 7, 9, 12 & 13 inhibiting activity are described in Examples 160-166.

The synthesis of the partially deuterated bis-amide MMP-13 inhibiting compounds of the invention and their biological activity assays are described in the following examples which are not intended to be limiting in any way.

EXAMPLES AND METHODS

Reagents were obtained from commercial sources and used without further purification unless otherwise stated. All reactions were performed using glassware that was oven dried overnight (100° C.). All solvents are of reagent grade. All reactions were carried out under nitrogen atmosphere unless otherwise stated. Organic reaction mixtures were concentrated using a Buchi rotary evaporator. Proton NMR spectra were recorded on a Varian Nuclear Magnetic Resonance spectrometer at 300 MHz.

Liquid chromatography coupled to mass spectrometry (LC-MS): The following Instrument and specifications were used to analyze the various compounds.
Liquid Chromatography:
Instrument: Shimadzu LC-10AD VP
Column: Agilent Zobax 3.5 SB-C18
Column internal diameter (ID): 4.6 mm
Column length: 50 mm
Gradient: 5% to 95% Acetonitrile and water both containing 0.1% formic acid.
Run time: 5 minutes
How rate: 1.5 ml/minute
High pressure: 4000 psi
Low pressure: 0 psi
Set temperature: 0° C.
Temperature Limit: 25° C.
LC-Mass Spec: Waters Micromass Quatro Ultima LC/MS (triple-quad MS), CTC Analytics PAL autosampler
Preparative, High Pressure Liquid Chromatography (Prep. HPLC): Revered Phase preparative purification condition is as follows:
Instrument: Waters UPLC system
Column: Waters Sunfire C18 Column
Column internal diameter (ID): 19 mm
Column length: 100 mm
Injection: 0.5-1 ml DMSO or MeOH
Gradient: 30% to 70% acetonitrile and water both containing 0.1% trifluoroacetic acid (TFA).
Run time: 4-7 minutes
Flow rate: 40 ml/minute Example 1

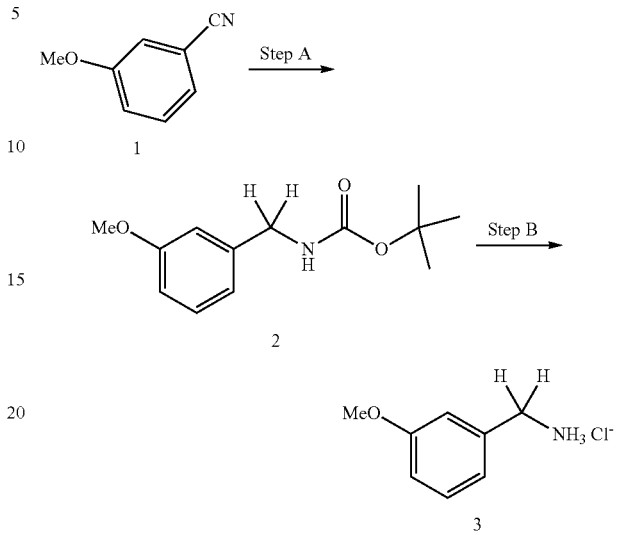

Step A

Following standard literature procedure (Caddick, S.; et al. Tetrahedron Letters, 41, p. 3513-3516, (2000)), commercially available 3-Methoxy benzonitrile (1) (4.0 mmole) (Aldrich) is added to a 100 round bottom flask containing a stir bar. To the flask is then added $NiCl_2*6H_2O$ (0.2 mmoles) and ditertbutlycarbonate (8.3 mmole) and mixture dissolved in 30 ml of anhydrous methanol under nitrogen atmosphere. The solution was then cooled to 0° C. and to the solution was slowly added in portions 1.0 grams of sodium borohydride making sure to keep the temperature ~0° C. After addition was complete the reaction was stirred under nitrogen atmosphere at 0° C. for 1 hour and then at room temperature for 24 hours. To the reaction was then added 0.5 ml of diethylenetriamine and mixture allowed to stir for an additional 1 hour. The volatile components of the reaction mixture was removed under reduced pressure to give a residue which was taken up in 100 ml of ethylacetate and organic layer washed with 10% citric acid, saturated sodium bicarbonate and then saturated sodium chloride in that order. The organic was separated and dried over anhydrous magnesium sulphate, filtered and the volatile components removed under reduced pressure to give a solid which was purified by column chromatography ($SiO_2$, Hexane:ethylacetate 70:30) to give 0.5 grams (53% yield) of (3-Methoxy-benzyl)-carbamic acid tert-butyl ester (2). $^1$H NMR (300 MHz, $CDCl_3$) δ 1.48 (s, 9H), 3.79 (s, 3H), 4.26-4.30 (br m, 2H), 4.90 (br s, 1H), 6.79-6.87 (m, 3H), 7.21-7.26 (m, 1H).

Step B

To 0.4 grams of (3-Methoxy-benzyl)-carbamic acid tert-butyl ester (2) was added 5 ml of a solution composed of 4 M HCl in anhydrous dioxane and mixture stirred under nitrogen atmosphere for 3 hours. The volatile components of the reaction mixture were then removed under reduced pressure to give a white solid which was triturated with 10 ml of diethyl ether and the resulting solid dried under vacuum to give 0.25 grams of 3-Methoxy-benzylamine (3) as the hydrochloride salt (86% yield). LC-MS (M+H) 138.

Example 2

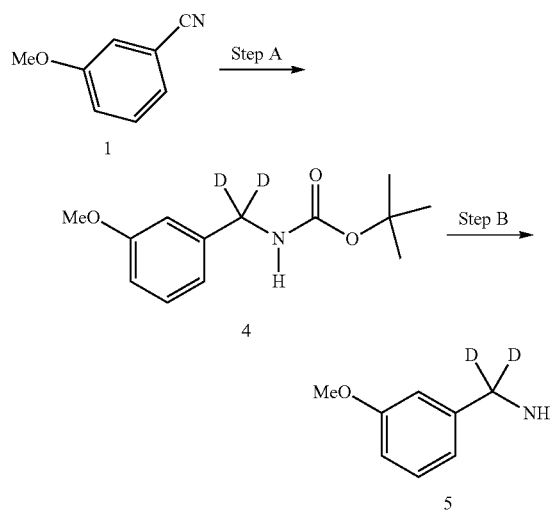

Step A

First commercially available 3-Methoxy benzonitrile (1) (4.0 mmole) (Aldrich) is added to a 50 ml round bottom flask containing a stir bar. To the flask is then added $NiCl_2*6D_2O$ (0.21 mmoles) [$NiCl_2*6D_2O$ was synthesized in the following manner: To a 25 ml round bottom flask was added 0.5 grams of commercially available $NiCl_2*6H_2O$ (Alfa Aesar) and dissolved with 5 ml of commercially available $D_2O$ (obtained from Cambridge Isotope Laboratories) and the volatile components removed under reduced pressure to give a yellow solid. To the solid was again added 5 ml of $D_2O$ and the volatile components removed under reduced pressure to give $NiCl_2*6D_2O$]. To the 50 ml flask was then added ditertbutlycarbonate (8.3 mmole) and mixture dissolved in 10 ml of anhydrous $CD_3OD$ (obtained from Acros Organics) and mixture stirred under nitrogen atmosphere until solution was complete. The solution was then cooled to 0° C. and to the solution was slowly added in portions a total of 1.0 grams of $NaBD_4$ (commercially obtained from Alfa Aesar) making sure to keep the temperature ~0° C. An additional 5 ml of $CD_3OD$ was added to wash the sides of the flask. After addition was complete the reaction was stirred under nitrogen atmosphere at 0° C. for 1 hour and then at room temperature for 12 hours. To the reaction mixture was then added 0.15 ml diethylenetriamine and mixture allowed to stir for an additional 20 minutes. The volatile components of the reaction mixture were then removed under reduced pressure to give a residue which was taken up in 100 ml of ethylacetate and organic layer washed with 10% citric acid, saturated sodium bicarbonate and then saturated sodium chloride in that order. The organic layer was separated and dried over anhydrous magnesium sulphate, filtered and the volatile components removed under reduced pressure to give a solid which was purified by column chromatography ($SiO_2$, Hexane:ethylacetate 70:30) to give 0.75 grams (78% yield) of [Dideutero-(3-methoxy-phenyl)-methyl]-carbamic acid tert-butyl ester (4). $^1H$ NMR (300 MHz, $CDCl_3$) δ 1.46 (s, 9H), 3.79 (s, 3H), 4.82 (br s, 1H), 6.79-6.90 (m, 3H), 7.21-7.29 (m, 1H).

Step B

To 0.75 grams of [Dideutero-(3-methoxy-phenyl)-methyl]-carbamic acid tert-butyl ester (4) in a 50 ml round bottom flask was added 5 ml of a solution composed of 4 M HCl in anhydrous dioxane and mixture stirred under nitrogen atmosphere for 3 hours. The volatile components of the reaction mixture were then removed under reduced pressure to give a white solid which was triturated with 10 ml of diethyl ether and the resulting solid dried under vacuum to give 0.35 grams of C,C-Dideutero-C-(3-methoxy-phenyl)-methylamine (5) as the hydrochloride salt (63% yield). $^1H$ NMR (300 MHz, $CD_3OD$) δ 3.81 (s, 3H), 6.85-7.05 (m, 3H), 7.30-7.39 (m, 1H). LC-MS (M+H) 140.

Example 3

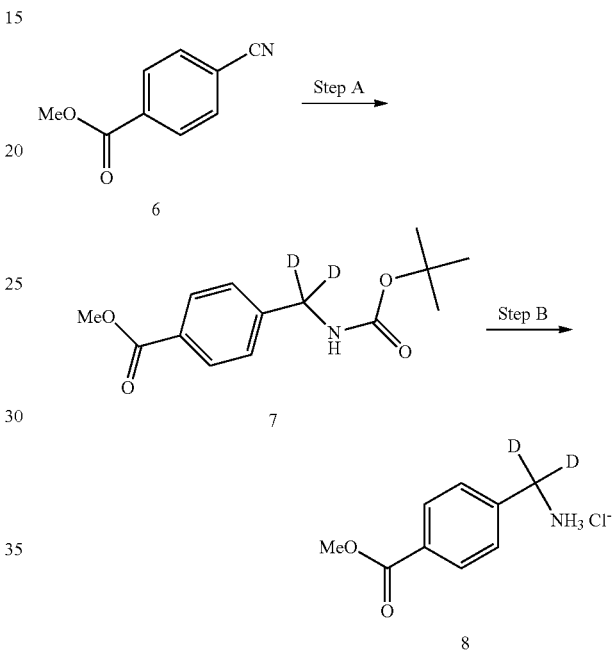

Step A

First commercially available 4-Cyano-benzoic acid methyl ester (6) (4.0 mmole) (Aldrich) is added to a 50 ml round bottom flask containing a stir bar. To the flask is then added $NiCl_2*6D_2O$ (0.21 mmoles) ($NiCl_2*6D_2O$ was synthesized following the method outlined in Example 2). To the 50 ml flask was then added ditertbutlycarbonate (6.8 mmole) and mixture dissolved in 12 ml of anhydrous $CD_3OD$ (obtained from Acros Organics) and mixture stirred under nitrogen atmosphere until solution was complete. The solution was then cooled to 0° C. and to the solution was slowly added in portions a total of 0.25 grams of $NaBD_4$ (commercially obtained from Alfa Aesar) making sure to keep the temperature ~0° C. After addition was complete the reaction was stirred under nitrogen atmosphere at 0° C. for 1 hour and then at room temperature for 24 hours. The volatile components of the reaction mixture were then removed under reduced pressure to give a residue which was taken up in 100 ml of ethylacetate and organic layer washed with 10% citric acid and then saturated sodium bicarbonate. The organic layer was separated and dried over anhydrous magnesium sulphate, filtered and the volatile components removed under reduced pressure to give a solid which was purified by column chromatography ($SiO_2$, Hexane:ethylacetate 70:30) to give 0.72 grams (66% yield) of 4-(tert-Butoxycarbonylamino-dideutero-methyl)-benzoic acid methyl ester (7). $^1$H NMR (300 MHz, CD$_3$OD) δ 1.46 (s, 9H), 3.90 (s, 3H), 4.90 (br s, 1H), 7.34 (d, 2H, J=8.1 Hz), 7.99 (d, 2H, J=8.1 Hz).

Step B

To 0.65 grams of 4-(tert-Butoxycarbonylamino-dideutero-methyl)-benzoic acid methyl ester (7) in a 25 ml round bottom flask was added 8 ml of a solution composed of 4 M HCl in anhydrous dioxane and mixture stirred under nitrogen atmosphere for 2 hours. The volatile components of the reaction mixture were then removed under reduced pressure to give a white solid which was triturated with diethyl ether and the resulting solid dried under vacuum to give 0.5 grams of 4-(Amino-dideutero-methyl)-benzoic acid methyl ester (8) as the hydrochloride salt (49% yield). $^1$H NMR (300 MHz, d6-DMSO) δ 1.46 (s, 9H), 3.84 (s, 3H), 6.63 (d, 2H, J=8.4 Hz), 7.97 (d, 2H, J=8.4 Hz), 8.60 (br s, 2H).

Example 4

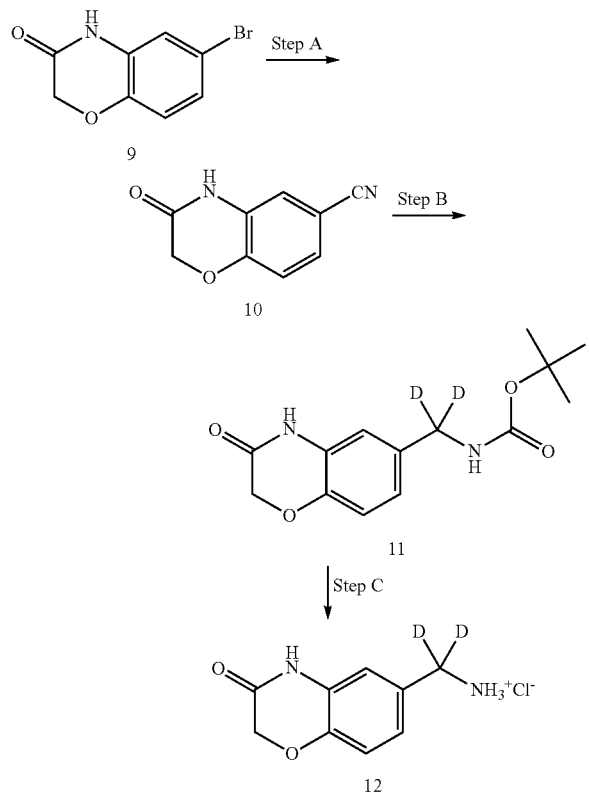

Step A

The synthesis of compound (10) is based on published literature procedure (Gege, C.; et al. J. Med. Chem. 55(2), 709-716, (2012)). First commercially available 6-bromo-4-H-benzo[1,4]oxazine-3-one (9) (4.3 mmole) (Alfa Aesar) is added to a thick walled glass vessel containing a stir bar. To the vessel is then added Copper (I) cyanide (12.2 mmoles) (obtained from Aldrich). The vessel was placed under vacuum then nitrogen atmosphere and then syringed 15 ml of anhydrous N-methylpyrolidinone and solution heated under closed nitrogen atmosphere using microwave radiation at 200° C. for 4 hours. The solution was then evaporated under reduced pressure to give an oil. To the oil was added 150 ml of ethylacetate and the organic layer washed with 10% citric acid and then both layers filtered though a celite plug and then the organic separated and washed with saturated NaHCO$_3$ and then saturated NaCl. The organic layer was separated and dried over anhydrous magnesium sulphate, filtered and the volatile components removed under reduced pressure to give a solid which was purified by column chromatography (SiO$_2$, methylene chloride:methanol 95:5) to give 0.2 grams (26% yield) of 3-Oxo-3,4-dihydro-2H-benzo[1,4]oxazine-6-carbonitrile (10). $^1$H NMR (300 MHz, d6-DMSO) δ 4.69 (s, 2H), 7.08 (d, 1H, J=8.4 Hz), 7.18 (s, 1H), 7.29 (d, 1H, J=8.4 Hz), 10.90 (s, 1H). LC-MS (M−H) 173.

Step B

3-Oxo-3,4-dihydro-2H-benzo[1,4]oxazine-6-carbonitrile (10) (1.0 mmole) is added to a 50 ml round bottom flask containing a stir bar. To the flask is then added NiCl$_2$*6D$_2$O (0.1 mmoles) (NiCl$_2$*6D$_2$O was synthesized following the method outlined in Example 2). To the 50 ml flask was then added ditertbutlycarbonate (1.8 mmole) and mixture partially dissolved in 3 ml of anhydrous CD$_3$OD (obtained from Acros Organics) and mixture cooled to 0° C. under nitrogen atmosphere. To the suspension was slowly added in portions a total of 75 milligrams of NaBD$_4$ (commercially obtained from Alfa Aesar) making sure to keep the temperature ~0° C. After addition was complete the reaction was stirred under nitrogen atmosphere at 0° C. for 1 hour and then at room temperature for 24 hours. The volatile components of the reaction mixture were then removed under reduced pressure to give a residue which was taken up in 150 ml of ethylacetate and organic layer washed with 10% citric acid and then saturated sodium bicarbonate. The organic layer was separated and dried over anhydrous magnesium sulphate, filtered and the volatile components removed under reduced pressure to give a solid which was purified by column chromatography (SiO$_2$, methylene chloride:methanol 90:10) to give 0.16 grams (55% yield) of [Dideutero-(3-oxo-3,4-dihydro-2H-benzo[1,4]oxazin-6-yl)-methyl]-carbamic acid tert-butyl ester (11). LC-MS (M−H) 279.

Step C

To 0.16 grams of [Dideutero-(3-oxo-3,4-dihydro-2H-benzo[1,4]oxazin-6-yl)-methyl]-carbamic acid tert-butyl ester (11) in a 25 ml round bottom flask was added 10 ml of a solution composed of 4 M HCl in anhydrous dioxane and mixture stirred under nitrogen atmosphere for 1 hour. The volatile components of the reaction mixture were then removed under reduced pressure to give a white solid which was triturated with diethyl ether and the resulting solid dried under vacuum to give 0.11 grams (91 of 6-(Amino-difluoro-methyl)-4H-benzo[1,4]oxazin-3-one (12) as the hydrochloride salt. LC-MS (M+H) 181

Examples 5-8

If one were to follow a similar procedure as that described in Example 3 using a substituted benzonitrile (A), NaBD$_4$ and NiCl$_2$*6D$_2$O one would obtain the resulting dideuterobenzylamine carbamic acid tert-butyl ester (B) which if one followed the procedure described in Example 3 in which the carbamic acid tert-butyl ester is treated with HCl in dioxane one would obtain the resulting dideuterobenzylamine (C) as the hydrochloride salt as indicated in the table below.

| Ex. | Amine A | Example carbamic acid tert-butyl ester B | Example Dideuterobenzylamine hydrochloride C |
|---|---|---|---|
| 5 | | | |
| 6 | | | |
| 7 | | | |
| 8 | | | |

Example 9

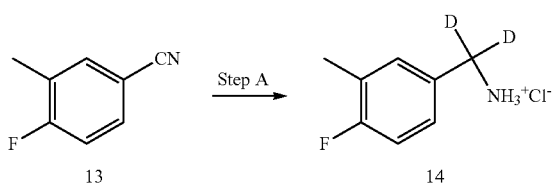

Step A

First commercially available 4-Fluoro-3-methyl-benzonitrile (13) (3.0 mmole) (Oakwood) is added to a 100 ml round bottom flask containing a stir bar. The flask was placed under vacuum then nitrogen and then 10 ml of anhydrous tetrahydrofuran was syringed in and mixture stirred until solution was complete. The solution was then cooled to −10° C. and then added in small portions LiAlD$_4$ (2.85 mmole) (obtained from Aldrich as a 90% pure reagent) making sure to keep the temperature ~0° C. After addition was complete the reaction was stirred under nitrogen atmosphere at 0° C. for 1 hour and then at room temperature for 48 hours. To the reaction was then added 0.15 ml of D$_2$O and then 0.1 ml of 20% NaOD and then 0.3 ml of D$_2$O in that order and mixture allowed to stir for 1 hour at room temperature. The reaction mixture was then filtered through celite and washed with methylene chloride. To the filtered organic liquid was then added 3 ml of a solution composed of 4 M HCl in anhydrous dioxane and the volatile components of the reaction mixture were then removed under reduced pressure to give a while solid. The white solid was triturated with diethyl ether and then placed under vacuum to give 0.5 grams of C,C-Dideutero-C-(4-fluoro-3-methyl-phenyl)-methylamine (14) as the hydrochloride salt (95% yield). $^1$H NMR (300 MHz, d6-DMSO) δ 2.21 (s, 3H), 7.10-7.49 (m, 3H), 8.50 (br s, 2H). LC-MS (M+H) 142.

Examples 10-13

If one were to follow a similar procedure as that described in Example 5 using a substituted benzonitrile (A), LiAlD$_4$ one would obtain the resulting dideuterobenzylamine which if one followed the procedure described in Example 5 in which the dideuterobenzylamine is treated with HCl in dioxane one would obtain the resulting dideuterobenzylamine (B) as the hydrochloride salt as indicated in the table below.

| Ex. | Amine A | Example Dideuterobenzylamine hydrochloride B |
|---|---|---|
| 10 | | |

| Ex. | Amine A | Example Dideuterobenzylamine hydrochloride B |
|---|---|---|
| 11 | 4-Br-C6H4-CN | 4-Br-C6H4-CD2-NH3+Cl- |
| 12 | C6H5-CN | C6H5-CD2-NH3+Cl- |
| 13 | 3-D3CO-C6H4-CN | 3-D3CO-C6H4-CD2-NH3+Cl- |

Example 14

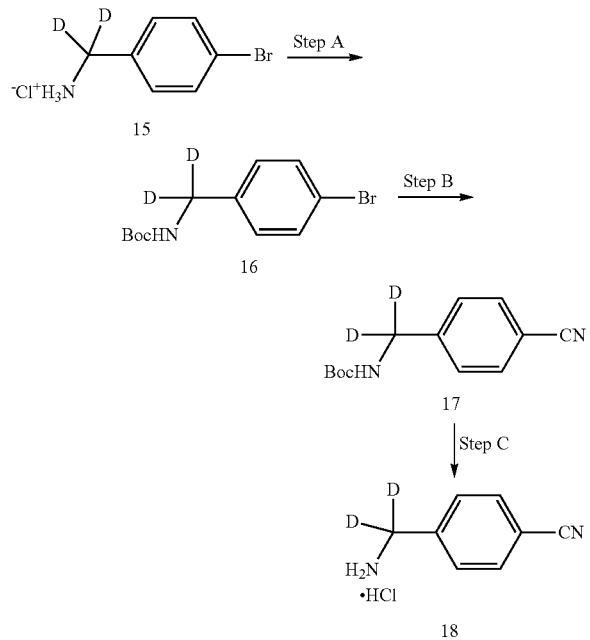

Step A

To make the tBoc protected amine (16) one could begin with taking one equivalent of the C-(4-Bromo-phenyl)-C, C-dideutero-methylamine hydrochloride (15) and then form the free base by first basifying it using aqueous base and then extracting it using methylene chloride to isolate the free amine. One equivalent of the dry free amine can then be dissolved in dry tetrahydrofuran (THF) (~50 mL) and then cooled to 0° C. To the cooled solution could then be added one equivalent of commercially available di-t-butyl dicarbonate (Aldrich) dissolved in dichloromethane (3-4 mL) followed by two equivalents of triethylamine (Et3N). The solution could then be allowed to warm to room temperature and then stirred for 3-4 h. The resulting reaction mixture can then be concentrated and then dissolved in methylene chloride and washed with aqueous 1N HCl (2×50 mL) and saturated NaHCO3 (50 mL). The organic layer can then be separated from the aqueous mixture and then dried over anhydrous MgSO4, filtered and concentrated to afford the crude tBoc protected amine (16).

Step B

One could combine 2 equivalents of ZnCN2 and 0.1 equivalents of Pd[PPh3]4 under nitrogen and then add the tBoc protected, bromo compound (16) (10-15 mmoles) dissolved in 25 mL anhydrous dimethylformamide (DMF). The resulting mixture can be heated to 100° C. for 18 h and then concentrated under reduced pressure to afford crude cyano compound (17) which can be purified by column chromatography to give pure [(4-Cyano-phenyl)-dideutero-methyl]-carbamic acid tert-butyl ester (17).

Step C

If one follows the method of Example 2, Step B, in which 1-2 grams (4-8 mmoles) of the [(4-Cyano-phenyl)-dideutero-methyl]-carbamic acid tert-butyl ester (17) can be suspended in a solution composed of 4 M HCl in anhydrous doxane and mixture stirred under nitrogen atmosphere for 3 hours. Then if the volatile components of the reaction mixture were then removed under reduced pressure one would produce a white solid which if triturated with diethyl ether and dried under vacuum one would produce the resulting amino acid (18) as the hydrochloride salt.

Example 15

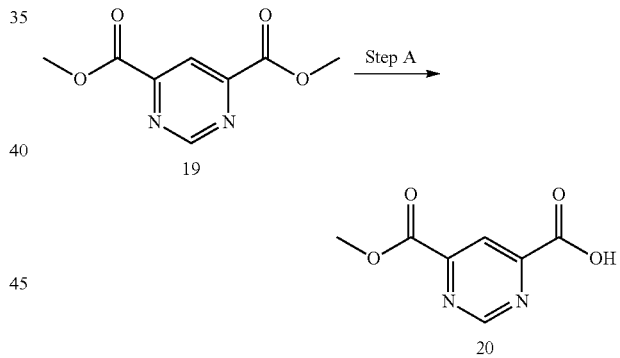

Step A

To a 100 ml round bottom flask containing a stir bar is added commercially available pyrimidine-4,6-dicarboxylic acid dimethyl ester (19) (obtained from Aldrich). To the solid was added a solution comprising 0.2 grams of sodium hydroxide dissolved in 10 ml anhydrous methanol and mixture stirred at room temperature under a nitrogen atmosphere for 1 hour. To the reaction mixture was then added 1.2 ml of a solution comprising 4 M hydrochloric acid in dioxane and mixture stirred for 10 minutes. To the reaction mixture was then added ~2 grams of silica gel (SiO2), and the volatile components removed under reduced pressure and solid added to a column and purified via column chromatography (SiO2, 40% ethylacetate in hexane) to give 0.77 grams (86%) of Pyrimidine-4,6-dicarboxylic acid monomethyl ester compound (20). $^1$H NMR (300 MHz, CD3OD) δ 4.04 (s, 3H), 8.59 (s, 1H), 9.46 (s, 1H). LC-MS (M+H) 183.

Example 16

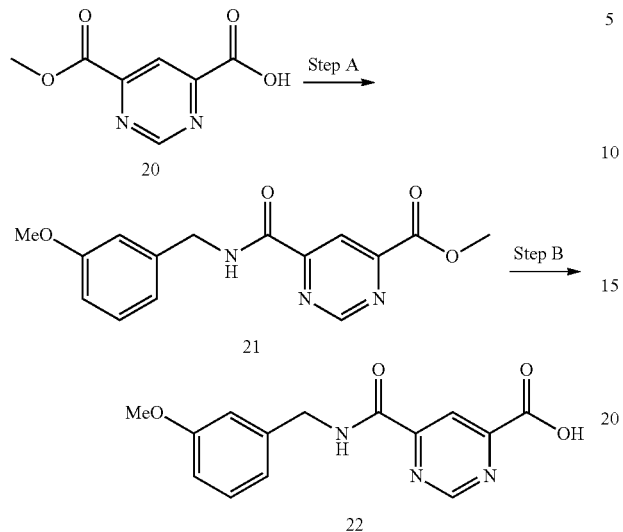

Step A

To a round bottom flask containing a stir bar was added Pyrimidine-4,6-dicarboxylic acid monomethyl ester compound (20) (0.82 mmole) and 3-Methoxy-benzylamine (3) (0.74 mmole) from Example 1 and 1-hydroxy-7-azabenzotriazole (0.82 mmol) (HOAT) (obtained from AK Scientific, Inc) and 2-(7-azabenzotriazole-1-yl)-N—N—N—N-tetramethyluronium-hexafluorophosphate (HATU) (0.90 mmol) (AK Scientific. Inc). To the mixture was then added 5 ml of anhydrous dimethylformamide (DMF) and mixture stirred at room temperature under a nitrogen atmosphere for 5 minutes. Then N-methylmorpholine (0.15 mL, 1.3 mmole) was injected and mixture stirred under nitrogen for 24 hours. The volatile components were then removed under reduced pressure to give a oil residue which was purified by column chromatography (SiO$_2$, 10-40% ethylacetate:hexane) to give 0.16 grams (64%) 6-(3-Methoxy-benzylcarbamoyl)-pyrimidine-4-carboxylic acid methyl ester (21) as a colorless oil. $^1$H NMR (300 MHz, CDCl$_3$) δ 3.80 (s, 3H), 4.07 (s, 3H), 4.66 (d, 2H, J=6.3 Hz), 6.85-6.95 (m, 3H), 7.26-7.31 (m, 1H), 8.30 (br s, 1H), 8.80 (s, 1H), 9.37 (s, 1H), LC-MS (M+H) 302.

Step B

To a round bottom flask containing 0.16 grams (0.53 mmole) of 6-(3-Methoxy-benzylcarbamoyl)-pyrimidine-4-carboxylic acid methyl ester (21) was added a stir bar and 3 ml of tetrahydrofuran (THF) and mixture stirred until solution was complete. To the solution was then added a 1 ml solution of 74 mg (1.32 mmole) of potassium hydroxide (KOH) in water and mixture stirred for 4 hours. To the mixture was then added concentrated hydrochloride acid until mixture was pH ~1. The volatile components of the reaction mixture were then removed under reduced pressure to give a white solid. The solid was taken up in 80 ml of ethyl acetate and organic washed with 40 ml of saturated NaCl and then organic separated and dried over magnesium sulfate (MgSO4), filtered the volatile components removed under reduced pressure to give 0.15 grams (98%) of 6-(3-Methoxy-benzylcarbamoyl)-pyrimidine-4-carboxylic acid (22) as a white solid. LC-MS (M+H) 288.

Example 17

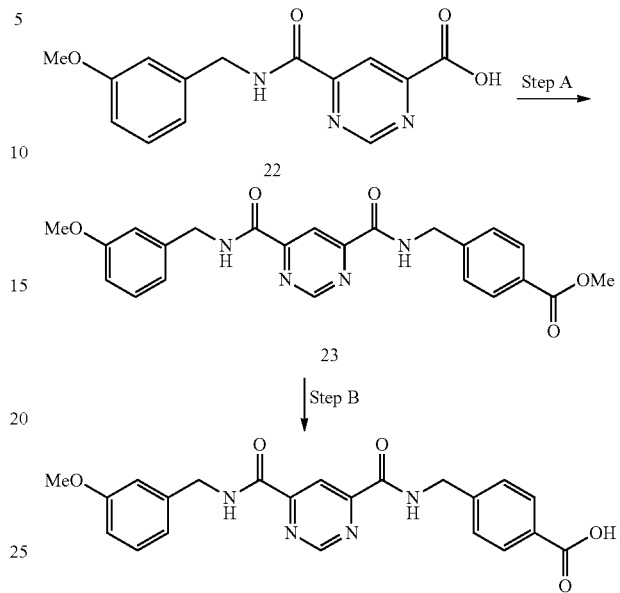

Step A

To a round bottom flask containing a stir bar and 6-(3-Methoxy-benzylcarbamoyl)-pyrimidine-4-carboxylic acid (22) (0.1 grams, 0.34 mmole) was added commercially available methyl 4-(aminomethyl)benzoate (0.35 mmol), 1-hydroxy-7-azabenzotriazole (0.35 mmol) (HOAT) and 2-(7-azabenzotriazole-1-yl)-N—N—N—N-tetramethyluronium-hexafluorophosphate (HATU) (0.40 mmol). To the mixture was then added 3 ml of anhydrous dimethylformamide (DMF) and mixture stirred for a few minutes. Then N-methylmorpholine (NMP) (0.71 mmole) was then added and mixture stirred under nitrogen for 48 hours. The volatile components were then removed under reduced pressure to give a oil residue which was purified by column chromatography (SiO2, 0-40% ethyl acetate:hexane) to give 78 milligrams (52%) of 4-({[6-(3-Methoxy-benzylcarbamoyl)-pyrimidine-4-carbonyl]-amino}-methyl)-benzoic acid methyl ester (23). $^1$H NMR (300 MHz, CDCl$_3$) δ 3.80 (s, 3H), 3.91 (s, 3H), 4.66 (d, 2H, J=6.3 Hz), 4.75 (d, 2H, J=6.0 Hz), 6.85-6.95 (m, 3H), 7.26-7.31 (m, 1H), 7.41 (d, 2H, J=8.7 Hz), 8.03 (d, 2H, J=8.7 Hz), 8.23 (br s, 1H), 8.30 (br s, 1H), 8.95 (s, 1H), 9.19 (s, 1H). LC-MS (M+H) 435.

Step B

To a 10 ml round bottom flask containing 76 mg (0.17 mmole) of 4-({[6-(3-Methoxy-benzylcarbamoyl)-pyrimidine-4-carbonyl]-amino}-methyl)-benzoic acid methyl ester (23) was added a stir bar and 2 ml of tetrahydrofuran (THF) and mixture stirred until solution was complete. To the solution was then added a 1 ml solution of 39 mg (0.69 mmole) of potassium hydroxide (KOH) in water and mixture stirred for 12 hours. To the mixture was then added 1N hydrochloride acid until mixture was pH ~2. The volatile components of the reaction mixture were then removed under reduced pressure to give a white solid. To the solid was added 5 ml of H$_2$O and mixture centrifuged and the liquid removed and solid dried under pump vacuum to give 55 mg (75%) of 4-({[6-(3-Methoxy-benzylcarbamoyl)-pyrimidine-4-carbonyl]-amino}-methyl)-benzoic acid (24) as a white solid. ¹H NMR (300 MHz, d6-DMSO) δ 3.70 (s, 3H), 4.47 (d, 2H, J=6.0 Hz), 4.57 (d, 2H, J=6.3 Hz), 6.75-6.89 (m, 3H), 7.15-7.25 (m, 1H), 7.42 (d, 2H, J=7.2 Hz), 7.87 (d, 2H, J=7.2 Hz), 8.44 (s, 1H), 9.45 (s, 1H), 9.65 (br s, 1H), 9.80 (br s, 1H). LC-MS (M+H) 421.

Example 18

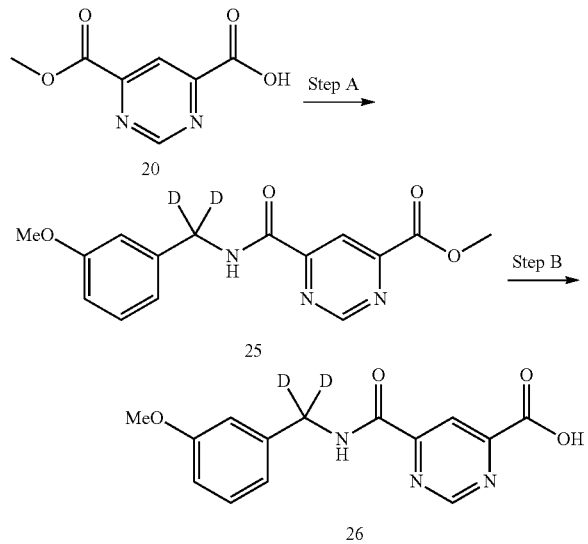

Step A

To a round bottom flask containing a stir bar was added Pyrimidine-4,6-dicarboxylic acid monomethyl ester compound (20) (0.94 mmole) and the hydrochloride salt of C,C-Dideutero-C-(3-methoxy-phenyl)-methylamine (5) (0.80 mmole) from Example 2 and 1-hydroxy-7-azabenzotriazole (0.82 mmol) (HOAT) (obtained from AK Scientific, Inc) and 2-(7-azabenzotriazole-1-yl)-N—N—N—N-tetramethyluronium-hexafluorophosphate (HATU) (0.93 mmol) (AK Scientific. Inc). To the mixture was then added 5 ml of anhydrous dimethylformamide and mixture stirred at room temperature under a nitrogen atmosphere for 5 minutes. Then N-methylmorpholine (0.2 ml, 1.7 mmole) was injected and mixture stirred under nitrogen for 20 hours. The volatile components were then removed under reduced pressure to give a oil residue which was purified by column chromatography (SiO₂, 10-40% ethyl acetate:hexane) to give 0.14 grams (58%) 6-{[Dideutero-(3-methoxy-phenyl)-methyl]-carbamoyl}-pyrimidine-4-carboxylic acid methyl ester (25) as a white crystalline solid. ¹H NMR (300 MHz, d6-DMSO) δ 3.80 (s, 3H), 4.07 (s, 3H), 6.80-6.95 (m, 3H), 7.26-7.31 (m, 1H), 8.30 (br s, 1H), 8.80 (s, 1H), 9.37 (s, 1H), LC-MS (M+H) 304.

Step B

To a round bottom flask containing 90 milligrams (0.29 mmole) of 6-{[Dideutero-(3-methoxy-phenyl)-methyl]-carbamoyl}-pyrimidine-4-carboxylic acid methyl ester (25) was added a stir bar and 2 ml of tetrahydrofuran and mixture stirred until solution was complete. To the solution was then added a 0.2 ml solution of 40% of NaOD in D₂O (commercially obtained from Cambridge Isotope Laboratories) and 1 ml of D₂O (obtained from Cambridge Isotope Laboratories) and mixture stirred for 1.5 hours. To the mixture was then added ~1 ml of a solution composed of 4 M hydrochloride acid in Dioxane and stirred for 10 minutes. The volatile components of the reaction mixture were then removed under reduced pressure to give a white solid which was triturated with water and then the solid placed under pump vacuum to give 84 milligrams (98%) of 6-{[Dideutero-(3-methoxy-phenyl)-methyl]-carbamoyl}-pyrimidine-4-carboxylic acid (26) as a white solid. ¹H NMR (300 MHz, d6-DMSO) δ 3.70 (s, 3H), 6.70-6.89 (m, 3H), 7.19-7.25 (m, 1H), 8.39 (s, 1H), 9.47 (s, 1H), 9.65 (br s, 1H). LC-MS (M+H) 290.

Example 19

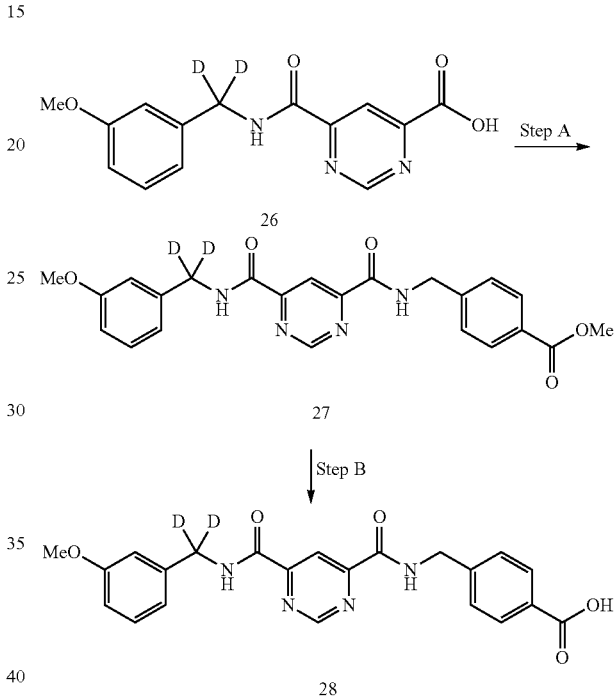

Step A

To a round bottom flask containing a stir bar and 6-{[Dideutero-(3-methoxy-phenyl)-methyl]-carbamoyl}-pyrimidine-4-carboxylic acid (26) (0.29 mmole) was added commercially available methyl 4-(aminomethyl)benzoate (0.30 mmol), 1-hydroxy-7-azabenzotriazole (0.29 mmol) (HOAT) and 2-(7-azabenzotriazole-1-yl)-N—N—N—N-tetramethyluronium-hexafluorophosphate (HATU) (0.34 mmol). To the mixture was then added 1 ml of anhydrous dimethylformamide and mixture stirred for a few minutes. Then N-methylmorpholine (0.66 mmole) was then added and mixture stirred under nitrogen for 24 hours. The volatile components were then removed under reduced pressure to give a oil residue which was purified by column chromatography (SiO₂, 0-40% ethyl acetate:hexane) to give 66 milligrams (52%) of 4-{[(6-{[Dideutero-(3-methoxy-phenyl)-methyl]-carbamoyl}-pyrimidine-4-carbonyl)-amino]-methyl}-benzoic acid methyl ester (27). ¹H NMR (300 MHz, CDCl₃) δ 3.80 (s, 3H), 3.91 (s, 1H), 4.75 (d, 2H, J=6.6 Hz), 6.85-6.95 (m, 3H), 7.25-7.31 (m, 1H), 7.42 (d, 2H, J=8.1 Hz), 8.03 (d, 2H, J=8.1 Hz), 8.23 (br s, 1H), 8.30 (br s, 1H), 8.95 (s, 1H), 9.19 (s, 1H). LC-MS (M+H) 437.

Step B

To a 10 ml round bottom flask containing 64 mg (0.15 mmole) of 4-{[(6-{[Dideutero-(3-methoxy-phenyl)-methyl]-carbamoyl}-pyrimidine-4-carbonyl)-amino]-methyl}-benzoic acid methyl ester (27) was added a stir bar and 1 ml of tetrahydrofuran (THF) and mixture stirred until solution was complete. To the solution was then added a 0.2 ml solution of 40% of NaOD in $D_2O$ (commercially obtained from Cambridge Isotope Laboratories) and 1 ml of $D_2O$ (obtained from Cambridge Isotope Laboratories) and mixture stirred for 24 hours. To the mixture was then added concentrated hydrochloride acid until mixture was pH ~2. The volatile components of the reaction mixture were then removed under reduced pressure to give a white solid. To the solid was added 5 ml of $H_2O$ and mixture centrifuged and the liquid removed and solid dried under pump vacuum to give a white solid which was purified by preparative thin layer chromatography (prep-TLC) ($SiO_2$, 10% methanol in methylene chloride) to isolate 20 mg (32%) of 4-{[(6-{[Dideutero-(3-methoxy-phenyl)-methyl]-carbamoyl}-pyrimidine-4-carbonyl)-amino]-methyl}-benzoic acid (28) as a white solid. ($R_f$=0.38, $SiO_2$, 10% methanol in methylene chloride), $^1$H NMR (300 MHz, $CD_3OD$) δ 3.76 (s, 3H), 4.69 (s, 2H), 6.75-6.95 (m, 3H), 7.20-7.25 (m, 1H), 7.46 (d, 2H, J=7.8 Hz), 7.98 (d, 2H, J=7.8 Hz), 8.68 (s, 1H), 9.37 (s, 1H). LC-MS (M+H) 423.

Examples 20-23

Following the procedure described in Example 18, Step A and using the substituted benzylamine hydrochloride salt (A), and Pyrimidine-4,6-dicarboxylic acid monomethyl ester compound (20) the resulting benzylamide product (B) was prepared as indicated in the table below.

| Ex. | Benzyl Amine A | Benzylamide B | Mass Spectrometry (M + H) |
|---|---|---|---|
| 20 | 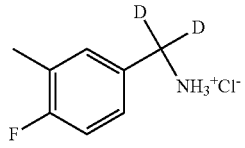 14 | 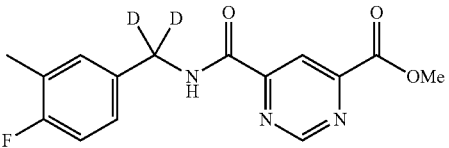 [SMILES: [2H]C([2H])(NC(=O)c1cc(C(=O)OC)ncn1)c1ccc(F)c(C)c1] 29 | 306 |
| 21 | 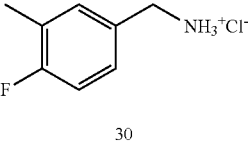 30 | 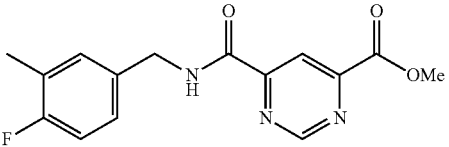 [SMILES: COC(=O)c1cc(C(=O)NCc2ccc(F)c(C)c2)ncn1] 31 | 304 |
| 22 | 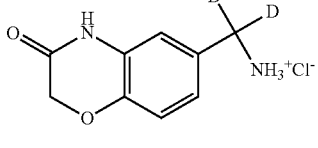 12 | 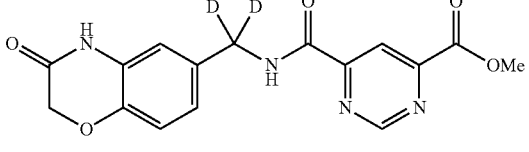 32 | 345 |
| 23 | 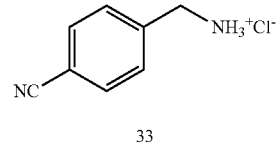 33 | 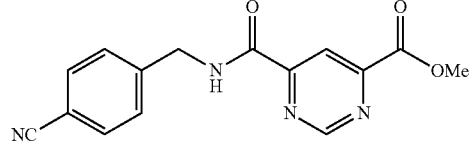 [SMILES: COC(=O)c1cc(C(=O)NCc2ccc(C#N)cc2)ncn1] 34 | 297 |

Examples 24-27

Following the procedure described in Example 18, Step B for the deuterated benzylamide product (B) or Example 16, Step B for the non-deuterated benzylamide product (B) the resulting free acid product (C) was prepared as indicated in the table below.

| Ex. | Benzylamide B | Acid C | Mass Spectrometry (M + H) |
|---|---|---|---|
| 24 | 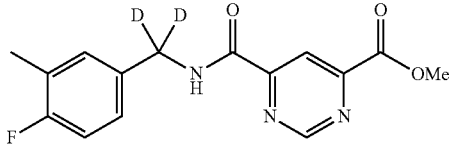 [SMILES: [2H]C([2H])(NC(=O)c1cc(C(=O)OC)ncn1)c1ccc(F)c(C)c1] 29 | 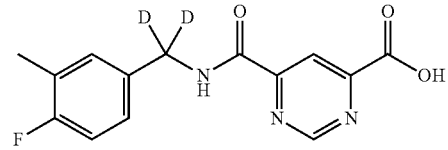 [SMILES: [2H]C([2H])(NC(=O)c1cc(C(=O)O)ncn1)c1ccc(F)c(C)c1] 35 | 292 |
| 25 | 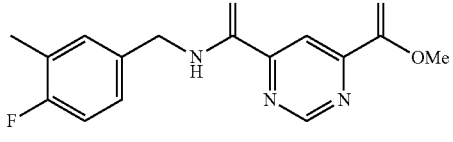 31 | 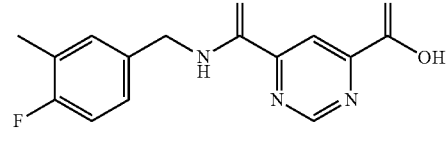 36 | 290 |
| 26 | 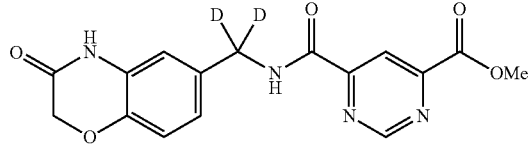 [SMILES: [2H]C([2H])(NC(=O)c1cc(C(=O)OC)ncn1)c1ccc2c(c1)NC(=O)CO2] 32 | 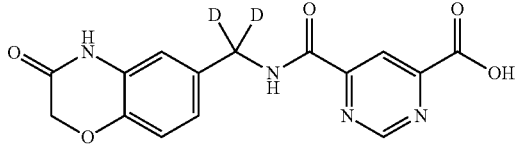 [SMILES: [2H]C([2H])(NC(=O)c1cc(C(=O)O)ncn1)c1ccc2c(c1)NC(=O)CO2] 37 | 331 |
| 27 | 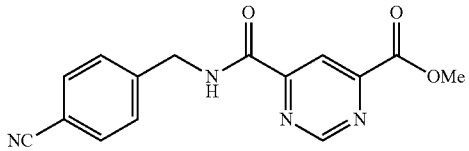 [SMILES: COC(=O)c1cc(C(=O)NCc2ccc(C#N)cc2)ncn1] 34 | 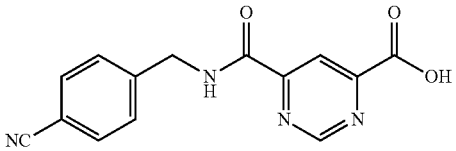 [SMILES: N#Cc1ccc(CNC(=O)c2cc(C(=O)O)ncn2)cc1] 38 | 283 |

Examples 28-32

Following the procedure described in Example 19, Step A for the free acid product (C) and coupling with a substituted benzylamine hydrochloride the resulting pyrimidine diamide (D) was prepared as indicated in the table below.

| Ex. | Acid C | Pyrimidine diamide D | Mass Spectrometry (M + H) |
|---|---|---|---|
| 28 | 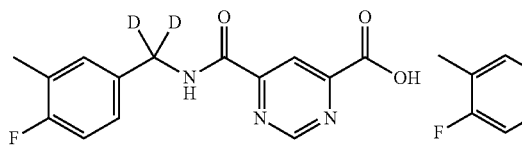 35 | 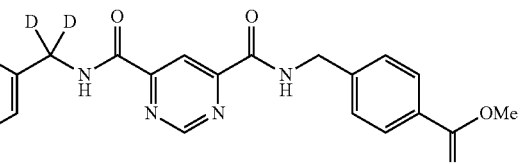 39 | 439 |

| Ex. | Acid C | Pyrimidine diamide D | Mass Spectrometry (M + H) |
|---|---|---|---|
| 29 | 36 | 40 | 437 |
| 30 | 37 | 41 | 478 |
| 31 | 38 | 42 | 404 |
| 32 | 38 | 43 | 402 |

Example 33

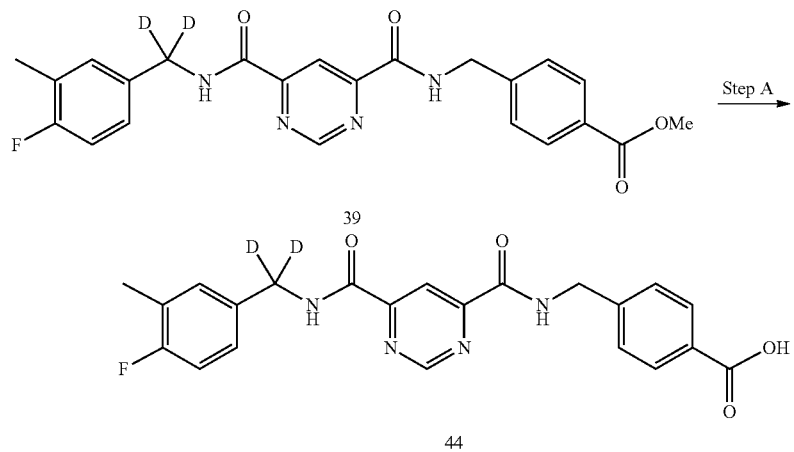

Step A

To a round bottom flask containing 4-{[(6-{[Dideutero-(4-fluoro-3-methyl-phenyl)-methyl]-carbamoyl}-pyrimidine-4-carbonyl)-amino]-methyl}-benzoic acid methyl ester (39) (0.158 g 0.360 mmol) in THF was added a 40% solution of NaOD in $D_2O$ (1 ml), $D_2O$ (1 ml) (both commercially obtained from Cambridge Isotope Laboratories) and reaction mixture stirred at room temperature for 2 hours. A white precipitate was observed to form and reaction mixture concentrated under reduced pressure then acidified with 15% aqueous HCl until the pH of the reaction mixture was ~2. The volatile components of the reaction mixture was removed under reduced pressure then the resulting solid was purified by reverses phase high pressure liquid chromatography (reversed phase-HPLC) to give 0.021 g (14%) of 4-{[(6-{[Dideutero-(4-fluoro-3-methyl-phenyl)-methyl]-carbamoyl}-pyrimidine-4-carbonyl)-amino]-methyl}-benzoic acid (44) as a white solid. δ $^1$HNMR (300 MHz, d6-DMSO) δ 2.18 (s, 3H), 4.57 (d, 2H, J=6.0 Hz), 7.02-7.24 (m, 3H), 7.42 (d, 2H, J=8.1 Hz), 7.87 (d, 2H, J=8.1 Hz), 8.45, (s, 1H), 9.45 (s, 1H), 9.64 (s, 1H), 9.77 (t, 1H, J=6.0 Hz). LC-MS (M+H): 425.

mixture stirred until solution was complete. To the solution was then added an aqueous solution of potassium hydroxide (KOH) (0.375 g, 0.67 mmol) and mixture stirred for 2 hours. To the mixture was then added concentrated hydrochloride acid until mixture was pH ~2. The volatile components of the reaction mixture were then removed under reduced pressure to give a white solid which was purified by preparative reversed phase HPLC to give 22 mg (28% yield) of 4-({[6-(4-Fluoro-3-methyl-benzylcarbamoyl)-pyrimidine-4-carbonyl]-amino}-methyl)-benzoic acid (45) as white solid. $^1$H NMR (300 MHz, d6-DMSO) δ 2.18 (s, 3H), 4.51 (d, 2H, J=6.0 Hz), 4.57 (d, 2H, J=6.0 Hz), 7.02-7.24 (m, 3H),

Example 34

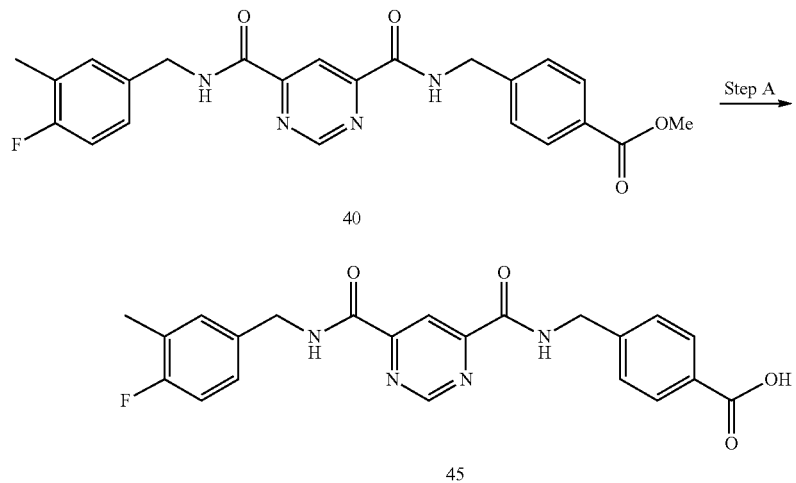

Step A

To a round bottom flask containing 73 mg (0.16 mmol) of 4-({[6-(4-Fluoro-3-methyl-benzylcarbamoyl)-pyrimidine-4-carbonyl]-amino}-methyl)-benzoic acid methyl ester (40) was added a stir bar and 1 ml of tetrahydrofuran (THF) and 7.42 (d, 2H, J=8.1 Hz), 7.88 (d, 2H, J=8.1 Hz), 8.45 (s, 1H), 9.46 (s, 1H), 9.67 (t, 1H, J=6.3 Hz), 9.78 (t, 1H, J=6.3 Hz). LC-MS (M+H) 423.

Example 35

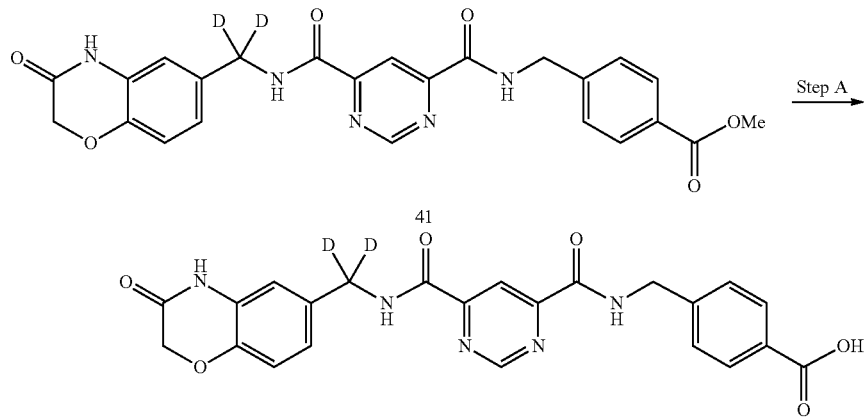

Step A

To a round bottom flask containing 4-{[(6-{[Dideutero-(3-oxo-3,4-dihydro-2H-benzo[1,4]oxazin-6-yl)-methyl]-carbamoyl}-pyrimidine-4-carbonyl)-amino]-methyl}-benzoic acid methyl ester (41) (23 mg 0.048 mmol) in THF was added a 40% solution of NaOD in D$_2$O (1 ml), D$_2$O (1 ml) (both commercially obtained from Cambridge Isotope Laboratories) and reaction mixture stirred at room temperature for 24 hours. To the reaction mixture was then added a solution composed of 4M HCl in dioxane until the pH of the reaction mixture was ~2. The volatile components of the reaction mixture was removed under reduced pressure to give a solid which was purified by preparative thin layer chromatography (prep-TLC) (SiO$_2$, 10% methanol in methylene chloride) to isolate 8 mg (36%) of 4-{[(6-{[Dideutero-(3-oxo-3,4-dihydro-2H-benzo[1,4]oxazin-6-yl)-methyl]-carbamoyl}-pyrimidine-4-carbonyl)-amino]-methyl}-benzoic acid (46) as a white solid. (R$_f$=0.46, SiO$_2$, 15% methanol in methylene chloride), $^1$H NMR (300 MHz, d6-DMSO) δ 4.49-4.54 (m, 4H), 6.87-6.88 (m, 3H), 7.27 (d, 2H, J=8.4 Hz), 7.81 (d, 2H, J=8.4 Hz), 8.45 (s, 1H), 9.44 (s, 1H), 9.63 (s, 1H), 9.68 (t, 1H, J=6.6 Hz), 10.66 (s, 1H). LC-MS (M+H) 464.

Example 36

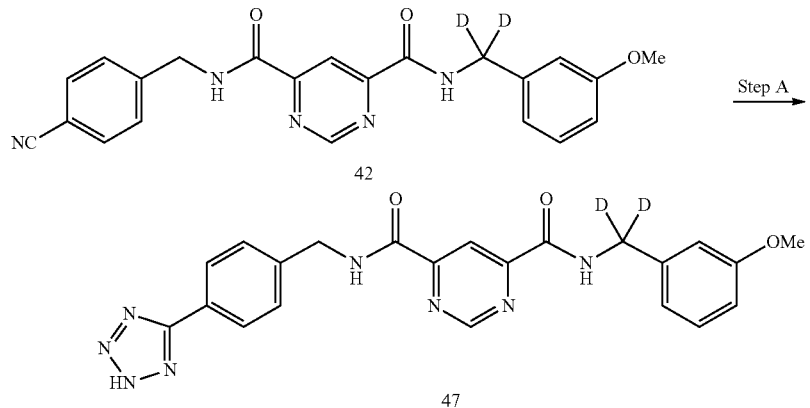

Step A

To a round bottom flask containing Pyrimidine-4,6-dicarboxylic acid 4-(4-cyano-benzylamide) 6-{[dideutero-(3-methoxy-phenyl)-methyl]-amide} (42) (0.12 g 0.29 mmol) was added 12 mg of dibutyltinoxide (0.048 mmole) and a stir bar. The flask was then placed under vacuum and then under a nitrogen atmosphere. To the flask was then added via syringe 3 ml of anhydrous toluene and mixture stirred under nitrogen for 5-10 minutes. To the flask was then added 0.15 ml (1.13 mmole) of trimethylsilylazide via syringe and mixture heated under nitrogen at 110° C. for 24 hours. The volatile components of the reaction mixture was removed under reduced pressure to give a reside which was purified by preparative thin layer chromatography (prep-TLC) (SiO2, 10% methanol-methylene chloride) to give 25 mg (19% yield) of Pyrimidine-4,6-dicarboxylic acid 4-{[dideutero-(3-methoxy-phenyl)-methyl]-amide}6-[4-(2H-tetrazol-5-yl)-benzylamide] (47) as a white solid. (SiO$_2$, R$_f$=0.30, 5% methanol in methylene chloride), δ $^1$HNMR (300 MHz, d6-DMSO) δ 3.70 (s, 3H), 4.53 (d, 2H, J=6.0 Hz), 6.78-6.90 (m, 3H), 7.21 (t, 1H, J=8.1 Hz), 7.36 (d, 2H, J=8.1 Hz), 7/91, (d, 2H, J=8.1 Hz), 8.46 (s, 1H), 9.47 (s, 1H), 9.64 (s, 1H), 9.69 (t, 1H, J=6.0 Hz). LC-MS (M+H): 447.

Example 37

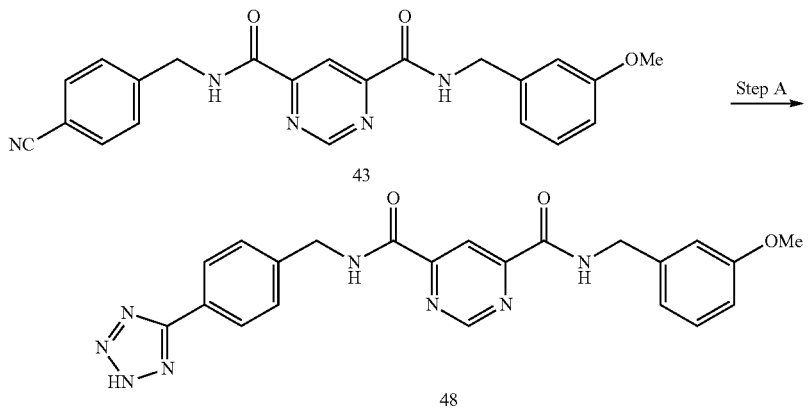

Step A

To a round bottom flask containing Pyrimidine-4,6-dicarboxylic acid 4-(4-cyano-benzylamide) 6-(3-methoxy-benzylamide) (43) (0.11 g 0.27 mmol) was added 11 mg of dibutyltinoxide (0.044 mmole) and a stir bar. The flask was then placed under vacuum and then under a nitrogen atmosphere. To the flask was then added via syringe 3 ml of anhydrous toluene and mixture stirred under nitrogen for 5-10 minutes. To the flask was then added 0.18 ml (1.64 mmole) of trimethylsilylazide via syringe and mixture heated under nitrogen at 110° C. for 24 hours. The volatile components of the reaction mixture was removed under reduced pressure to give a reside which was purified by preparative thin layer chromatography (prep-TLC) (SiO2, 10% methanol-methylene chloride) to give 20 mg (16% yield) of Pyrimidine-4,6-dicarboxylic acid 4-(3-methoxy-benzylamide) 6-[4-(2H-tetrazol-5-yl)-benzylamide] (48) as a white solid. (SiO$_2$, R$_f$=0.30, 5% methanol in methylene chloride) δ $^1$HNMR (300 MHz, d6-DMSO) δ 3.70 (s, 3H), 4.47 (d, 2H, J=6.3 Hz), 4.52 (d, 2H, J=6.3 Hz), 6.78-7.22 (m, 4H), 7.33 (d, 2H, J=8.1 Hz), 7.90, (d, 2H, J=8.1 Hz), 8.47 (s, 1H), 9.45 (s, 1H), 9.65-9.68 (m, 2H). LC-MS (M+H): 445.

Example 38

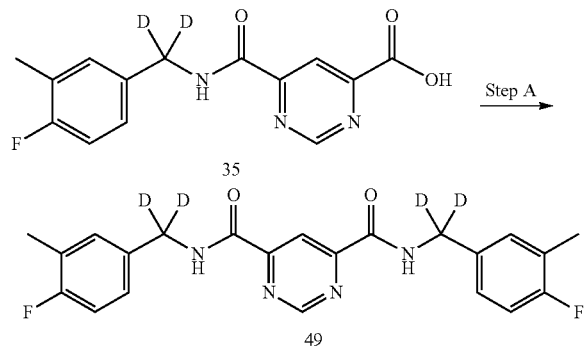

Step A

To a round bottom flask containing a stir bar and 6-{[Dideutero-(4-fluoro-3-methyl-phenyl)-methyl]-carbamoyl}-pyrimidine-4-carboxylic acid (35) (0.16 mmole) was added C,C-Dideutero-C-(4-fluoro-3-methyl-phenyl)-methyl-ammonium; chloride (14) (0.26 mmol), 1-hydroxy-7-azabenzotriazole (0.15 mmol) (HOAT) and 2-(7-azabenzotriazole-1-yl)-N—N—N—N-tetramethyluronium-hexafluorophosphate (HATU) (0.25 mmol). To the mixture was then added 1 ml of anhydrous dimethylformamide and mixture stirred for a few minutes. Then N-methylmorpholine (0.89 mmole) was then added and mixture stirred under nitrogen for 24 hours. The volatile components were then removed under reduced pressure to give a oil residue which was purified by preparative thin layer chromatography (prep-TLC) (SiO2, 10% methanol in methylene chloride) to give 25 mg (37%) of Pyrimidine-4,6-dicarboxylic acid bis-{[dideutero-(4-fluoro-3-methyl-phenyl)-methyl]-amide} (49). (SiO$_2$, R$_f$=0.55, 10% methanol in methylene chloride), $^1$H NMR (300 MHz, CD$_3$OD) δ 2.23 (s, 6H), 3.91 (s, 1H), 6.85-7.30 (m, 6H), 8.66 (s, 1H), 9.34 (s, 1H). LC-MS (M+H) 415.

Example 39

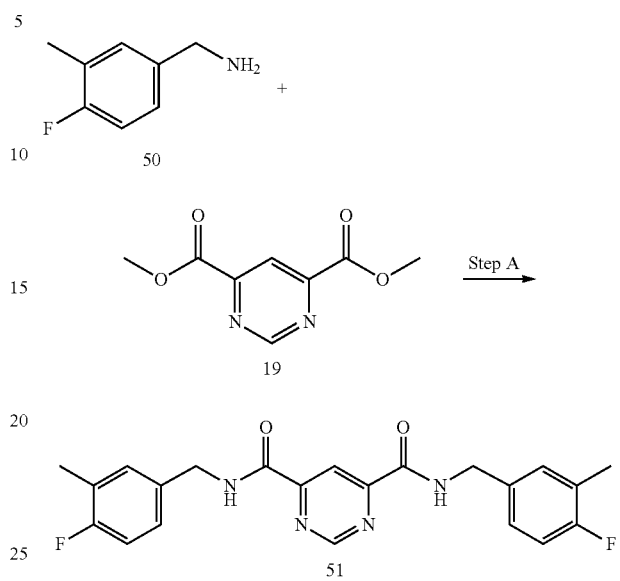

Step A

To a thick walled glass vessel containing a stir bar and 23 mg (0.11 mmole) of commercially available dimethyl pyrimidine-4,6-dicarboxylate (obtained from Oakwood Products) (19) was added a large excess (0.25 ml) of commercially available 4-Fluoro-3-methyl-benzylamine (50) (obtained from Aldrich) and 0.5 ml of anhydrous dimethylformamide and mixture heated while stirring under closed nitrogen atmosphere at 85° C. using microwave radiation (Biotage) for 24 hours. The volatile components of the reaction mixture were removed under reduced pressure to give a solid which was recrystallized from diethyl ether to give 0.42 grams (87%) of Pyrimidine-4,6-dicarboxylic acid bis-(4-fluoro-3-methyl-benzylamide) (51) as a white crystal solid. $^1$H NMR (300 MHz, CD$_3$OD) δ 2.23 (s, 6H), 4.55 (s, 4H), 6.85-7.30 (m, 6H), 8.66 (s, 1H), 9.34 (s, 1H). LC-MS (M+H) 411.

Example 40

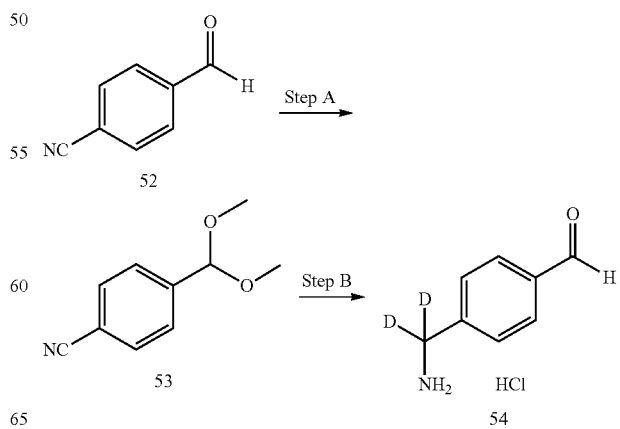

Step A

To a solution of commercially available 4-Formyl-benzonitrile (52) (1.31 g, 10 mmol) in anhydrous methanol (25 ml) was added p-Toluenesulfonic acid (172 mg, 1 mmol), and the reaction mixture was heated at 70° C. for 10 hours. The volatile components of the reaction mixture were removed under reduced pressure to give a residue. To the residue was added ethyl acetate (50 mL) and the resulting organic solution was washed with sat. NaHCO$_3$ solution, separated and then dried over anhydrous sodium sulfate. The mixture was filtered and the volatile components of the reaction mixture were then removed under reduced pressure to give a solid which was purified by column chromatography (SiO$_2$) using hexane-ethyl acetate (8:2) to give the resulting 4-Dimethoxymethyl-benzonitrile (53) as an oil (1.2 g, 70%). LC-MS (M+H): 172

Step B

To a solution of (53) (253 mg, 1.48 mmol) in THF at 0° C., LiAlD$_4$ (0.062 g, 1.48 mmol) was added portion-wise being careful to maintain the temperature of the reaction mixture to ~0° C. The reaction mixture was then stirred at 0° C. for an hour and then allowed to stir it at room temp for another 3 h. The reaction mixture was then quenched with 0.062 g of D$_2$O, 0.062 g of NaOD (using a 40% NaOD solution in D$_2$O), and then three portions of 0.062 g of D$_2$O in that order. The reaction mixture was then filtered through celite and washed with CH$_2$Cl$_2$. The combined solutions were then dried over sodium sulfate and then filtered. To the organic solution was then added a solution of 4N HCl in dioxane (15 mL) and the reaction mixture stirred for 10 hours. Hexane (30 mL) was then added to give a white precipitate which was filtered and dried to give the desired 4-(Amino-difluoro-methyl)-benzaldehyde (282 mg, 82%) (55) as the hydrochloride salt. LC-MS (M+H): 138

Example 41

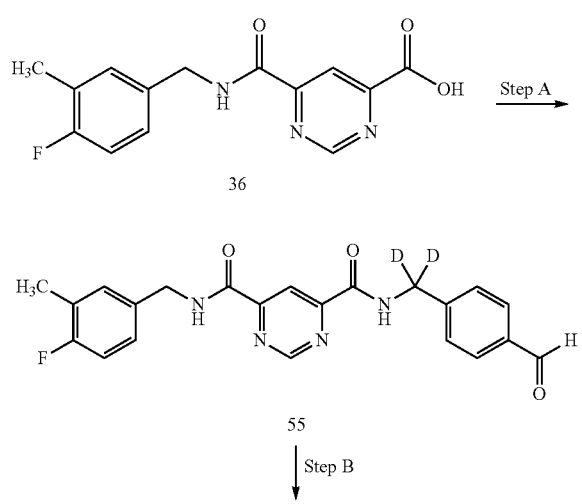

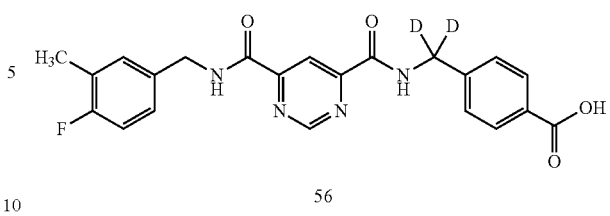

56

Step A

To a round bottom flask containing a stir bar was added 6-(4-Fluoro-3-methyl-benzylcarbamoyl)-pyrimidine-4-carboxylic acid (36) (0.290 g, 1 mmol), the hydrochloric acid salt of 4-(Amino-difluoro-methyl)-benzaldehyde HCl salt 55 (0.173 g, 1 mmol), 1-hydroxy-7-azabenzotriazole (HOAT) (0.132 g, 1 mmol) and anhydrous DMF (3 mL) and mixture stirred for 2-3 minutes. Then N-methylmorpholine (0.2 mL) and 2-(7-azabenzotriazole-1-yl)-N—N—N—N-tetramethyluronium-hexafluorophosphate (HATU) (0.437 g, 1.14 mmol) were then added at room temperature and the reaction was stirred for 1 hour. The volatile components of the reaction mixture were then removed under reduced pressure to give a residue which was taken up in ethyl acetate and organic washed with 10% citric acid, separated and organic layer dried over sodium sulfate. The solid was filtered the volatile components of the reaction mixture reduced under reduced pressure to give a residue. The residue was then purified by column chromatography (SiO$_2$, 0-50% ethyl acetate-hexane) to give the desired Pyrimidine-4,6-dicarboxylic acid 4-{[dideutero-(4-formyl-phenyl)-methyl]-amide}6-(4-fluoro-3-methyl-benzylamide) (55) as a white solid (0.146 g, 36%). LC-MS (M+H): 409.

Step B

To a solution of Pyrimidine-4,6-dicarboxylic acid 4-{[dideutero-(4-formyl-phenyl)-methyl]-amide}6-(4-fluoro-3-methyl-benzylamide) (55) (114 mg, 0.28 mmol) in acetic acid (15 mL) was added sulfamic acid (55 mg, 0.56 mmol) and mixture stirred for 10 min. To this reaction mixture was then added at room temperature a solution composed of Sodium chlorite (38 mg, 0.42 mmol) in water (1 mL) and mixture stirred for 3 h. To the reaction mixture was added enough water to cause precipitation of the reaction mixture. The white precipitate was filtered and dried to give 75 mg of a white solid. The solid was purified by column chromatography (SiO$_2$, ethyl acetate-MeOH, 9:1) to give the desired 4-(Dideutero-{[6-(4-fluoro-3-methyl-benzylcarbamoyl)-pyrimidine-4-carbonyl]-amino}-methyl)-benzoic acid (56) (45 mg, 38%) as a white solid. $^1$HNMR (300 MHz, d6-DMSO) δ 2.18 (s, 3H), 4.44 (d, 2H, J=6.3 Hz)), 7.02-7.23 (m, 3H), 7.42 (d, 2H, J=8.4 Hz), 7.87 (d, 2H, J=8.4 Hz), 8.44, (s, 1H), 8.46 (s, 1H), 9.45 (s, 1H), 9.65 (t, 1H, J=6.0 Hz), 9.75 (s, 1H). LC-MS (M+H): 425.

Examples 42-46

If one were to follow the procedure described in Example 19, Step A for the free acid product (C) and if one were to couple the substituted benzylamine hydrochloride (D) the resulting pyrimidine diamide (E) would be prepared.

| Ex. | Acid C | Benzyl amine hydrochloride D |
|---|---|---|
| 42 | (structure 35) | (structure 8) |
| 43 | (structure 26) | (structure 8) |
| 44 | (structure 37) | (structure 8) |
| 45 | (structure 60) | (structure 8) |
| 46 | (structure 62) | (structure 8) |

| Ex. | Pyrimidine diamide E |
|---|---|
| 42 | (structure 57) |

| | |
|---|---|
| 43 | 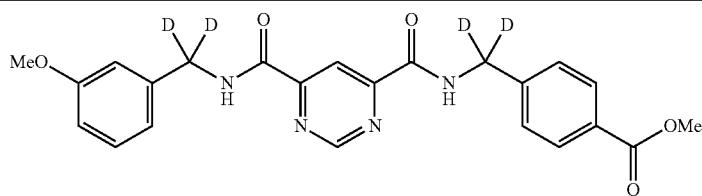 58 |
| 44 | 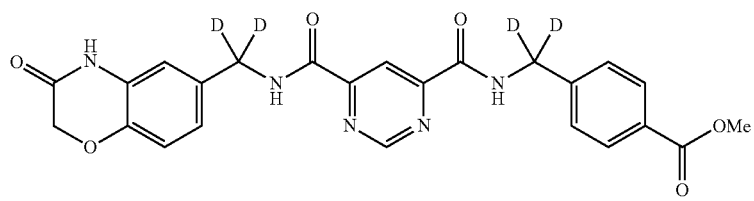 [SMILES: [2H]C([2H])(NC(=O)c1cc(C(=O)NC([2H])([2H])c2ccc3c(c2)NC(=O)CO3)ncn1)c1ccc(C(=O)OC)cc1] 59 |
| 45 | 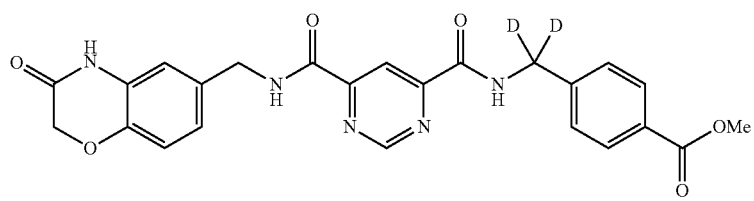 [SMILES: [2H]C([2H])(NC(=O)c1cc(C(=O)NCc2ccc3c(c2)NC(=O)CO3)ncn1)c1ccc(C(=O)OC)cc1] 61 |
| 46 | 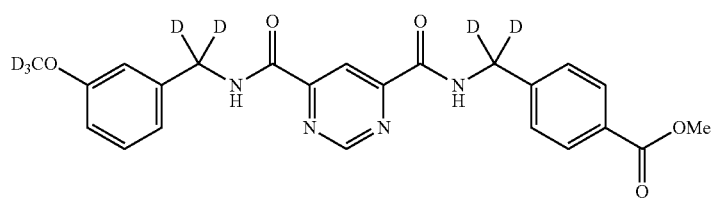 63 |
Examples 47-51
If one were to follow the procedure described in Example 33, Step A for the diamide ester product (E) the resulting pyrimidine acid (F) would be prepared.
| Ex. | Pyrimidine diamide ester product E | Pyrimidine diamide E |
|---|---|---|
| 47 | 35 | 64 |

| Ex. | Pyrimidine diamide ester product E | Pyrimidine diamide E |
|---|---|---|
| 48 | (26) MeO-C6H4-CD2-NH-C(O)-pyrimidine-C(O)-OH | (65) MeO-phenyl-CD2-NH-C(O)-pyrimidine-C(O)-NH-CD2-phenyl-COOH |
| 49 | (37) benzoxazinone-CD2-NH-C(O)-pyrimidine-C(O)-OH | (66) benzoxazinone-CD2-NH-C(O)-pyrimidine-C(O)-NH-CD2-phenyl-COOH |
| 50 | (60) benzoxazinone-CH2-NH-C(O)-pyrimidine-C(O)-OH | (67) benzoxazinone-CH2-NH-C(O)-pyrimidine-C(O)-NH-CD2-phenyl-COOH |
| 51 | (62) D3CO-phenyl-CD2-NH-C(O)-pyrimidine-C(O)-OH | (68) D3CO-phenyl-CD2-NH-C(O)-pyrimidine-C(O)-NH-CD2-phenyl-COOH |

Example 52

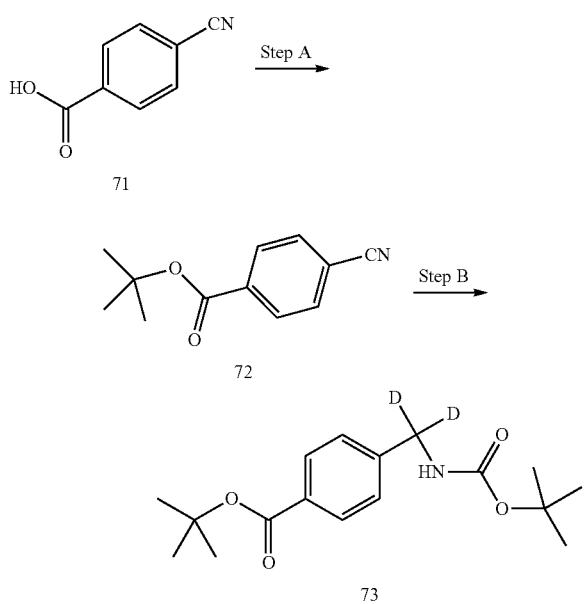

Step A

First commercially available 4-Cyano-benzoic acid (71) (35.3 mmole) (Acros) is added to a 250 ml round bottom flask containing a stir bar. To the flask is then added dry toluene (45 mL) and Di-tert-butoxymethyl dimethylamine (28 mL) (Alfa Aesar) at 80° C. At this temperature the mixture was stirred at 80° C. under nitrogen atmosphere for 24 h. After cooling to room temperature the volatile components of the reaction mixture were removed under reduced pressure to give a solid which was taken up in 200 ml of diethyl ether and organic layer washed three times with 10% aqueous sodium hydroxide solution (3×60 ml) and then twice with 10% citric acid solution (2×60 ml) and then once with saturated $NaHCO_3$ and then organic separated and dried over sodium sulphate, filtered and the resulting solid purified by column chromatography ($SiO_2$, 10% methylene chloride in hexane) to give 3.1 grams (43% yield) of 4-Cyano-benzoic acid tert-butyl ester (72) as a white crystalline solid. NMR (300 MHz, $CDCl_3$) δ 1.60 (s, 9H), 7.71 (d, 2H, J=8.1 Hz), 8.07 (d, 2H, J=8.1 Hz). LC-MS (M+H) 204

Step B

To one equivalent (4.92 mmoles) of 4-Cyano-benzoic acid tert-butyl ester (72) in a thick walled vessel was added one equivalent of di-tert-butyl dicarbonate and 0.43 grams of 10% Palladium on activated carbon (Aldrich) and 40 ml of deuterated ethanol ($CH_3CH_2OD$) and mixture shaken at room temperature using a Parr hydrognator in the presence of Deuterium gas (D₂) (Aldrich) at 50 psi for 24 hours. The mixture was then filtered through a medium porosity fritted glass funnel containing celite and the retentate washed with another 20 ml ethanol. The organic washes were combined and the volatile components of the reaction mixture were then removed under reduced pressure to give the desired 4-(tert-Butoxycarbonylamino-dideutero-methyl)-benzoic acid tert-butyl ester (73). NMR (300 MHz, CDCl₃) δ 1.44 (S, 9H), 1.58 (s, 9H), 4.80 (br. s, 1H), 7.31 (d, 2H, J=8.4 Hz), 7.88 (d, 2H, J=8.4 Hz). LC-MS (M+Na) 332.

Example 53

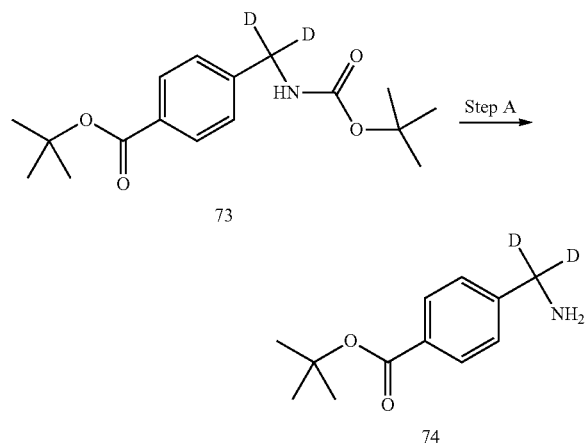

Step A

Following the method of Lin and co-workers (Lin, L. S.; et al. Tetrahedron Letters, 41, 7013-7016, 2000), to a 25 ml round bottom flask containing 0.32 gram (1.0 mmole) of 4-(tert-Butoxycarbonylamino-dideutero-methyl)-benzoic acid tert-butyl ester (73) was added 15 ml of tert-butyl acetate and mixture stirred until solution was complete. To the solution was then added 0.3 ml of concentrated sulphuric acid and mixture stirred under a nitrogen atmosphere for 2 hours. The reaction mixture was then made basic with saturated sodium bicarbonate and the mixture extracted with ethyl acetate and the organic layer separated and washed with saturated sodium chloride. The organic layer was then separated and dried over sodium sulphate, filtered and the volatile components of the reaction mixture were then removed under reduced pressure to give the desired 4-(Amino-dideutero-methyl)-benzoic acid tert-butyl ester (74). LC-MS (M+H) 210.

Example 54

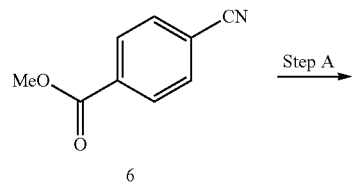

Step A

To one equivalent (37.2 mmoles) of 4-Cyano-benzoic acid methyl ester (6) in a thick walled glass vessel was added 1.1 equivalents of di-tert-butyl dicarbonate and 1 grams of 10% Palladium on activated carbon (Aldrich) and 70 ml of deuterated ethanol (CH₃CH₂OD obtained from Cambridge Isotope Laboratories) and mixture shaken at room temperature using a Parr hydrognator in the presence of Deuterium gas (D₂) (Aldrich) at 45 psi for 20 hours. The mixture was then filtered through a medium porosity fritted glass funnel containing celite and the retentate washed with methylene chloride. The organic washes were combined and the volatile components of the reaction mixture were then removed under reduced pressure to give 9.5 grams (95% yield) of the desired 4-(tert-Butoxycarbonylamino-dideutero-methyl)-benzoic acid methyl ester (7). ¹H NMR (300 MHz, CD₃OD) δ1.46 (s, 9H), 3.90 (s, 3H), 4.90 (br s, 1H), 7.34 (d, 2H, J=8.1 Hz), 7.99 (d, 2H, J=8.1 Hz). LC-MS (M+Na) 290.

Step B

To 9 grams (33.7 mmole) of 4-(tert-Butoxycarbonylamino-dideutero-methyl)-benzoic acid methyl ester (7) in a 250 ml round bottom flask was added 115 ml of a solution composed of 4 M HCl in anhydrous dioxane and mixture stirred under nitrogen atmosphere for 5 hours. The volatile components of the reaction mixture were then removed under reduced pressure to give ½ the original volume of reaction mixture. To the reaction mixture was then added 100 ml of diethyl ether and solid filtered through a medium porosity fritted glass funnel. The filtered solid was washed with another 50 ml of diethyl either and then dried under pump vacuum to give 6.0 grams (88% yield) of the desired 4-(Amino-dideutero-methyl)-benzoic acid methyl ester (8) as the hydrochloride salt. ¹H NMR (300 MHz, d6-DMSO) δ 1.46 (s, 9H), 3.84 (s, 3H), 6.63 (d, 2H, J=8.4 Hz), 7.97 (d, 2H, J=8.4 Hz), 8.60 (br s, 2H). LC-MS (M+H) 168.

Examples 55-59

If one were to follow a similar procedure as that described in Example 18 using the pyrimidine compound (20) and amine (A) one would obtain compounds (B) as indicated in the table below.

| Ex. | Amine A | Compound 20 | Example Monoamide Pyrimidine B |
|---|---|---|---|
| 55 | 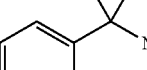 | 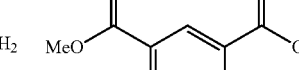 | 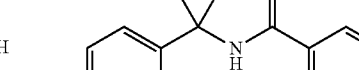 |
| 56 | 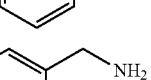 | 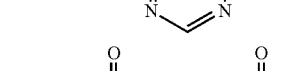 | 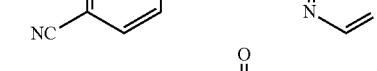 |
| 57 | 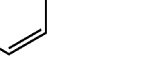 | 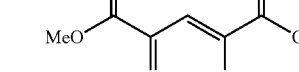 | 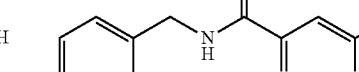 |
| 58 |  | 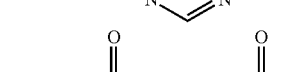 |  |
| 59 | 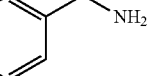 | 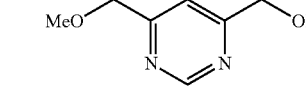 | 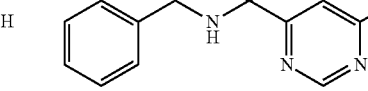 |
Examples 60-81
If one were to follow a similar procedure as that described in Example 19, Step A using the mono acid pyrimidine Acid (B) and amine (C) to give the resulting diamide pyrimidine (D) one would obtain compounds as indicated in the table below.
| Ex. | Monoamide Pyrimidine Acid B | Amine C |
|---|---|---|
| 60 | | |
| 61 | | |
| 62 | | |
| 63 | | |

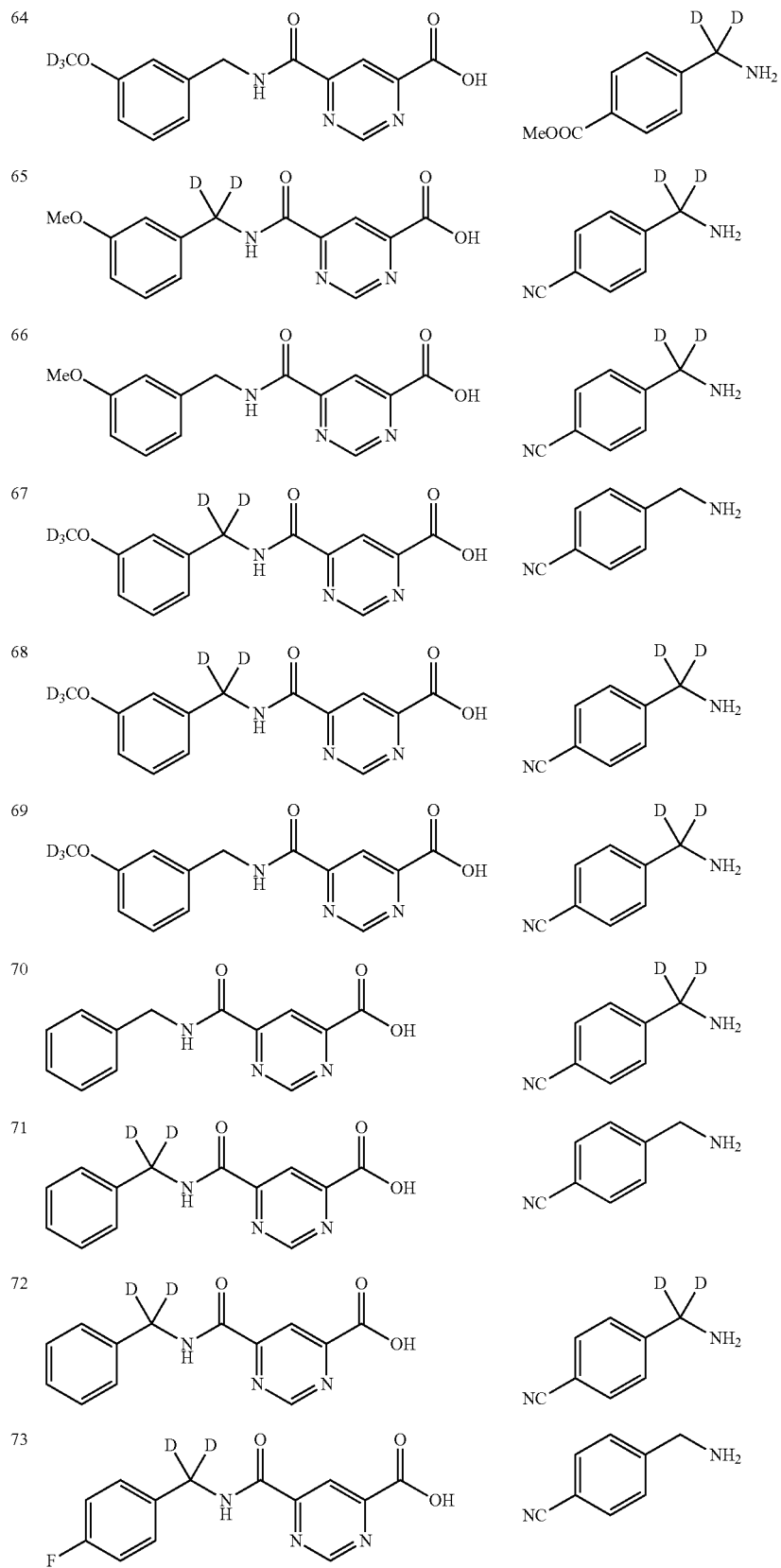

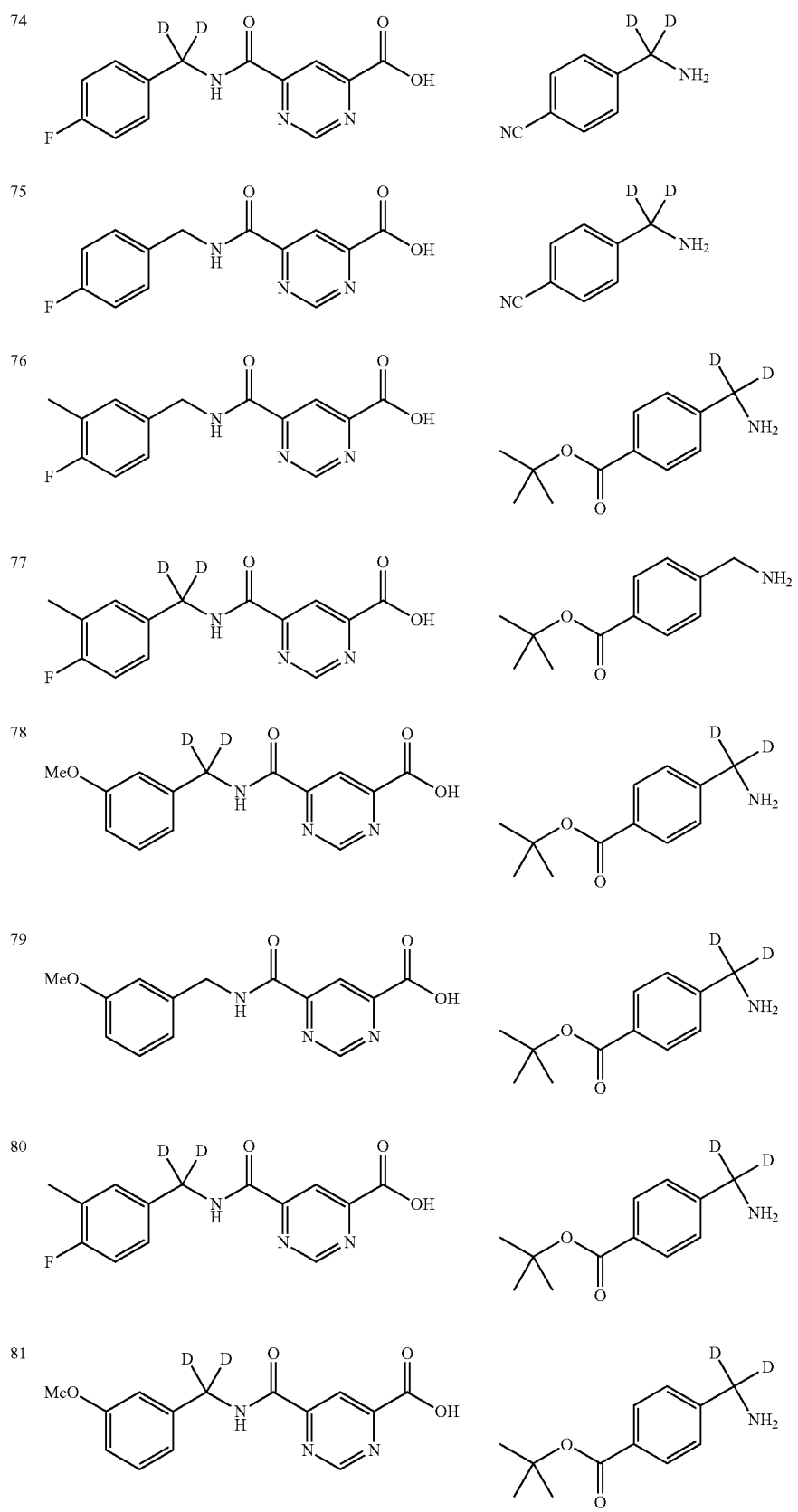

-continued
| Ex. | Diamide Pyrimidine Examples D |
|---|---|
| 60 | 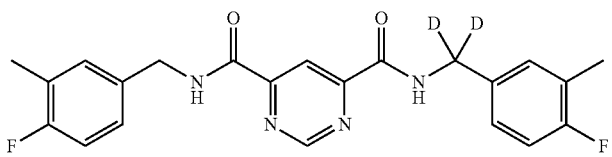 [SMILES: [2H]C([2H])(NC(=O)c1cc(C(=O)NCc2ccc(F)c(C)c2)ncn1)c1ccc(F)c(C)c1] |
| 61 | 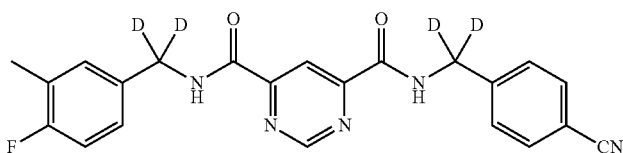 [SMILES: [2H]C([2H])(NC(=O)c1cc(C(=O)NC([2H])([2H])c2ccc(F)c(C)c2)ncn1)c1ccc(C#N)cc1] |
| 62 | 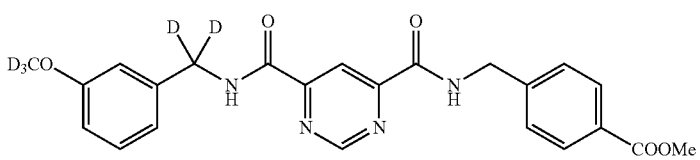 |
| 63 | 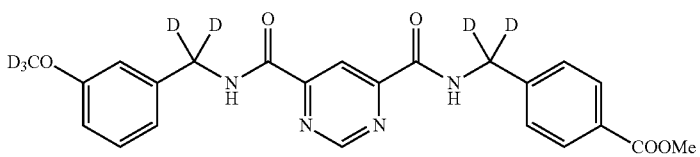 |
| 64 | 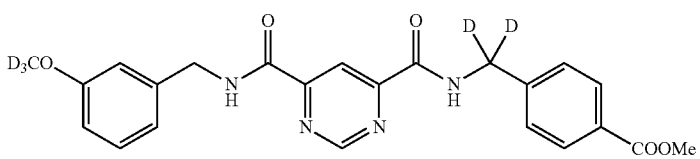 |
| 65 | 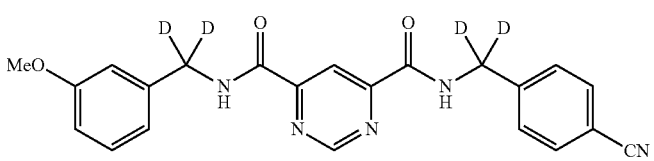 [SMILES: [2H]C([2H])(NC(=O)c1cc(C(=O)NC([2H])([2H])c2cccc(OC)c2)ncn1)c1ccc(C#N)cc1] |
| 66 | 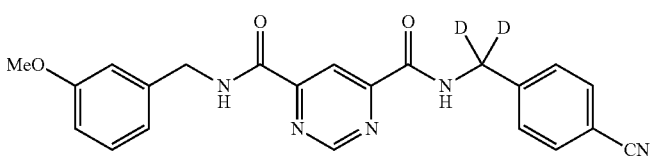 [SMILES: [2H]C([2H])(NC(=O)c1cc(C(=O)NCc2cccc(OC)c2)ncn1)c1ccc(C#N)cc1] |
| 67 | 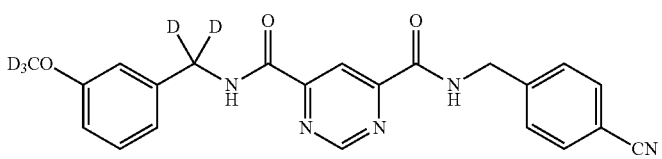 |
| 68 | 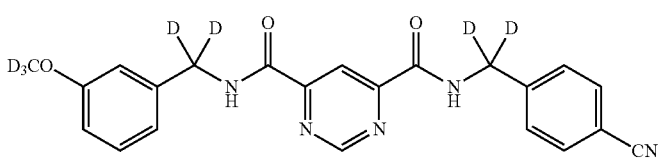 |

-continued
| 69 | 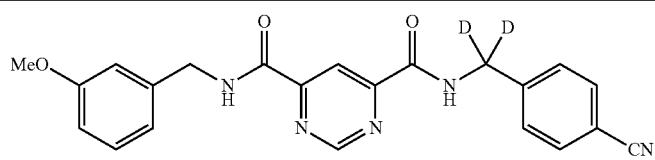 |
| --- | --- |
| 70 | 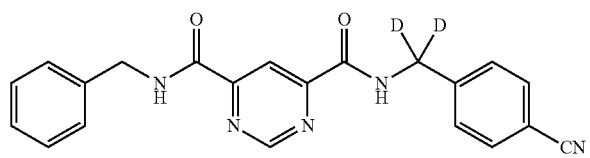 [SMILES: [2H]C([2H])(NC(=O)c1cc(C(=O)NCc2ccccc2)ncn1)c1ccc(C#N)cc1] |
| 71 | 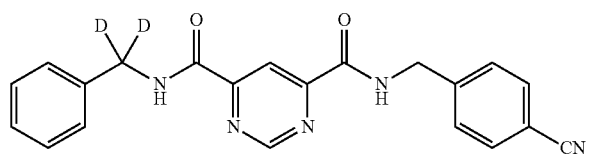 [SMILES: [2H]C([2H])(NC(=O)c1cc(C(=O)NCc2ccc(C#N)cc2)ncn1)c1ccccc1] |
| 72 | 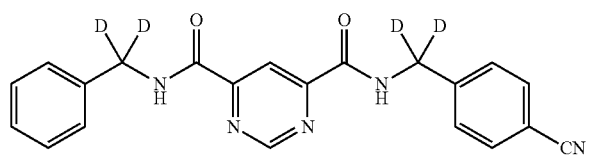 [SMILES: [2H]C([2H])(NC(=O)c1cc(C(=O)NC([2H])([2H])c2ccc(C#N)cc2)ncn1)c1ccccc1] |
| 73 | 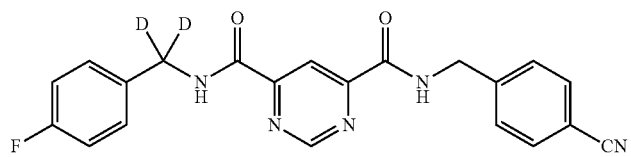 [SMILES: [2H]C([2H])(NC(=O)c1cc(C(=O)NCc2ccc(C#N)cc2)ncn1)c1ccc(F)cc1] |
| 74 | 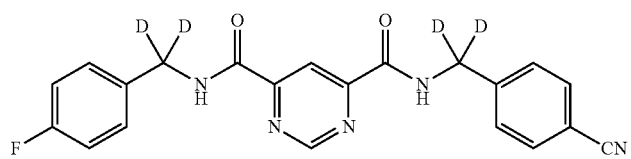 [SMILES: [2H]C([2H])(NC(=O)c1cc(C(=O)NC([2H])([2H])c2ccc(C#N)cc2)ncn1)c1ccc(F)cc1] |
| 75 | 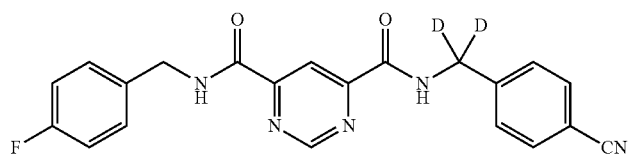 [SMILES: [2H]C([2H])(NC(=O)c1cc(C(=O)NCc2ccc(F)cc2)ncn1)c1ccc(C#N)cc1] |
| 76 | 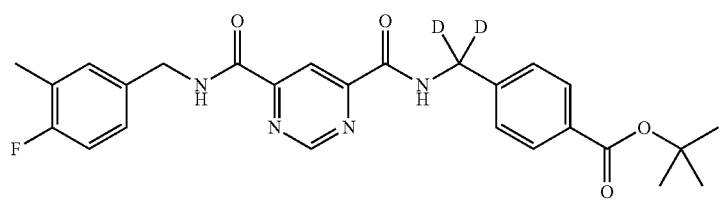 [SMILES: [2H]C([2H])(NC(=O)c1cc(C(=O)NCc2ccc(F)c(C)c2)ncn1)c1ccc(C(=O)OC(C)(C)C)cc1] |
| 77 | 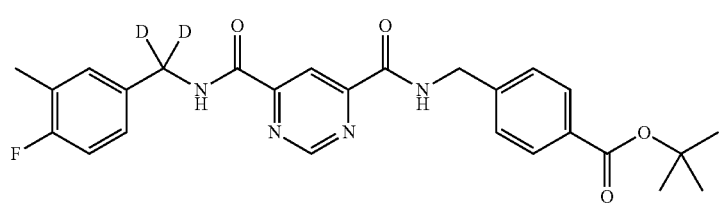 [SMILES: [2H]C([2H])(NC(=O)c1cc(C(=O)NCc2ccc(C(=O)OC(C)(C)C)cc2)ncn1)c1ccc(F)c(C)c1] |

| | | |
|---|---|---|
| 78 | 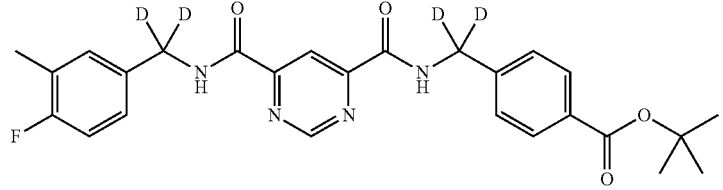 [SMILES: [2H]C([2H])(NC(=O)c1cc(C(=O)NC([2H])([2H])c2ccc(F)c(C)c2)ncn1)c1ccc(C(=O)OC(C)(C)C)cc1] | |
| 79 | 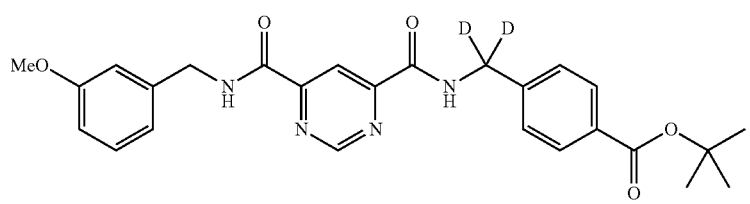 [SMILES: [2H]C([2H])(NC(=O)c1cc(C(=O)NCc2cccc(OC)c2)ncn1)c1ccc(C(=O)OC(C)(C)C)cc1] | |
| 80 | 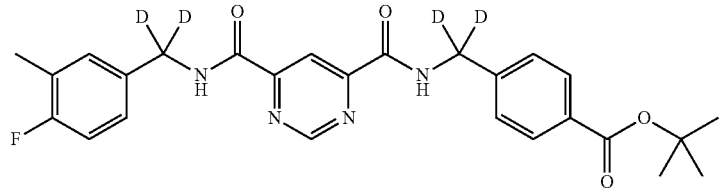 [SMILES: [2H]C([2H])(NC(=O)c1cc(C(=O)NC([2H])([2H])c2ccc(F)c(C)c2)ncn1)c1ccc(C(=O)OC(C)(C)C)cc1] | |
| 81 | 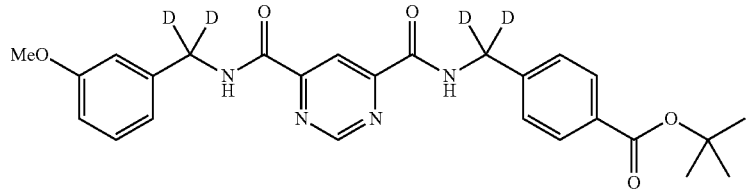 [SMILES: [2H]C([2H])(NC(=O)c1cc(C(=O)NC([2H])([2H])c2cccc(OC)c2)ncn1)c1ccc(C(=O)OC(C)(C)C)cc1] | |
Examples 82-123
If one were to follow a similar procedure as that described in Example 36 using the Diamide Pyrimidine (D) to give the resulting tetrazole (E) one would obtain compounds as indicated in the table below.
| Ex. | Diamide Pyrimidine Examples D | Diamide Pyrimidine Examples E |
|---|---|---|
| 82 | 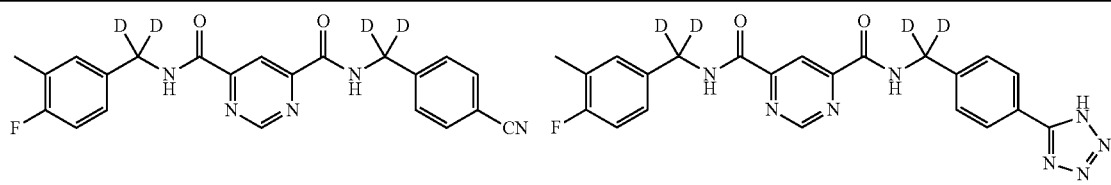 | |
| 83 | 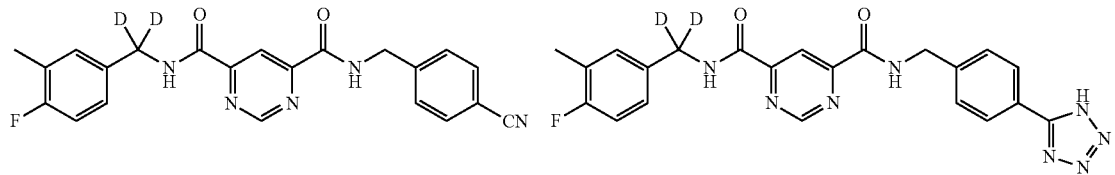 | |
| 84 | 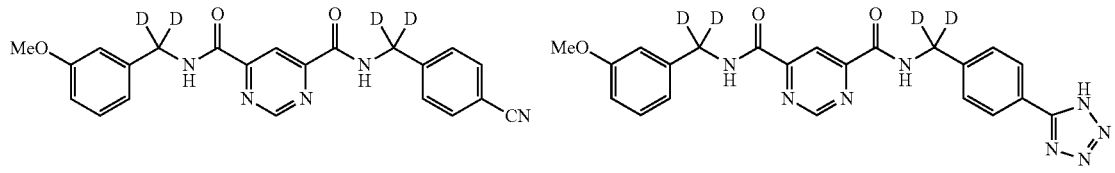 | |

| Ex. | Diamide Pyrimidine Examples D | Diamide Pyrimidine Examples E |
|---|---|---|
| 85 | 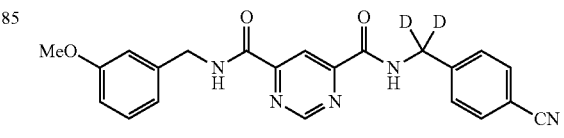 | 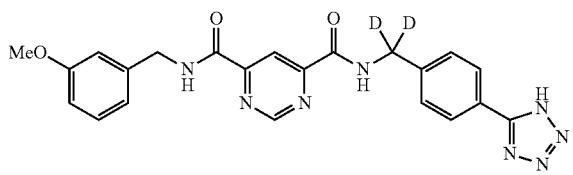 [SMILES: [2H]C([2H])(NC(=O)c1cc(C(=O)NCc2cccc(OC)c2)ncn1)c1ccc(-c2nnn[nH]2)cc1] |
| 86 | 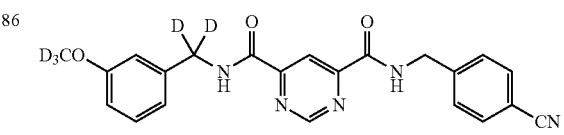 | 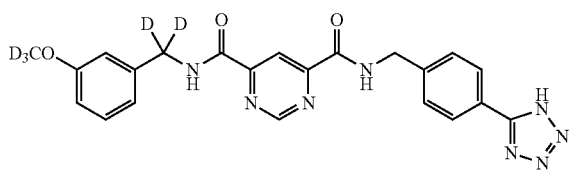 |
| 87 | 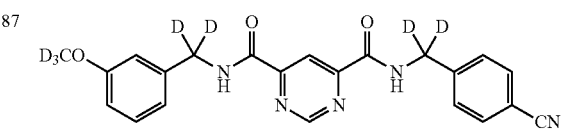 | 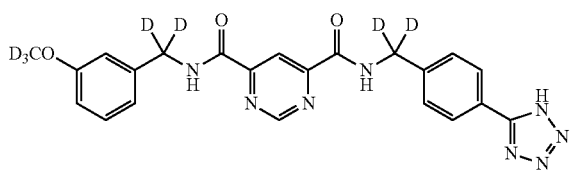 |
| 88 | 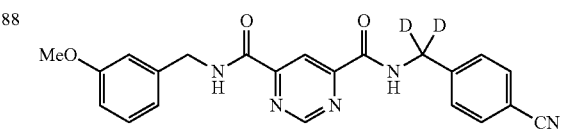 | 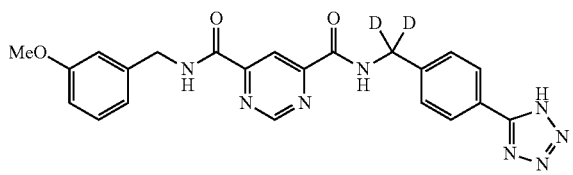 [SMILES: [2H]C([2H])(NC(=O)c1cc(C(=O)NCc2cccc(OC)c2)ncn1)c1ccc(-c2nnn[nH]2)cc1] |
| 89 | 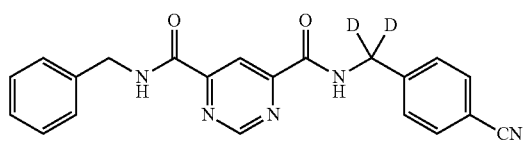 [SMILES: [2H]C([2H])(NC(=O)c1cc(C(=O)NCc2ccccc2)ncn1)c1ccc(C#N)cc1] | 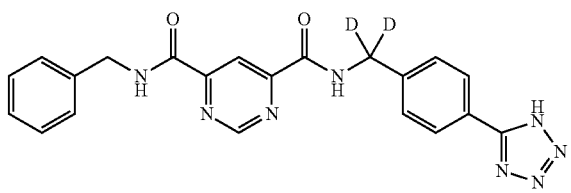 [SMILES: [2H]C([2H])(NC(=O)c1cc(C(=O)NCc2ccccc2)ncn1)c1ccc(-c2nnn[nH]2)cc1] |
| 90 | 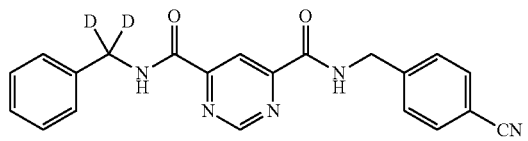 [SMILES: [2H]C([2H])(NC(=O)c1cc(C(=O)NCc2ccc(C#N)cc2)ncn1)c1ccccc1] | 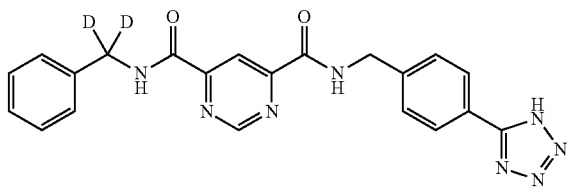 [SMILES: [2H]C([2H])(NC(=O)c1cc(C(=O)NCc2ccc(-c3nnn[nH]3)cc2)ncn1)c1ccccc1] |
| 91 | 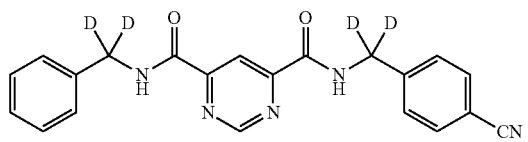 [SMILES: [2H]C([2H])(NC(=O)c1cc(C(=O)NC([2H])([2H])c2ccc(C#N)cc2)ncn1)c1ccccc1] | 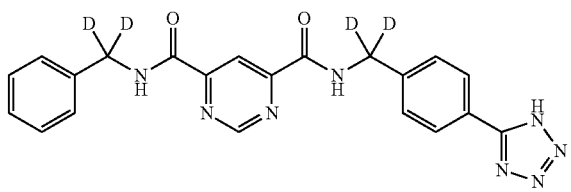 [SMILES: [2H]C([2H])(NC(=O)c1cc(C(=O)NC([2H])([2H])c2ccc(-c3nnn[nH]3)cc2)ncn1)c1ccccc1] |
| 92 | 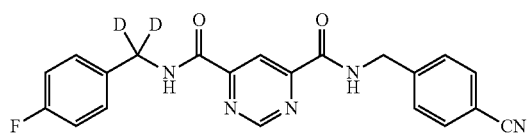 | 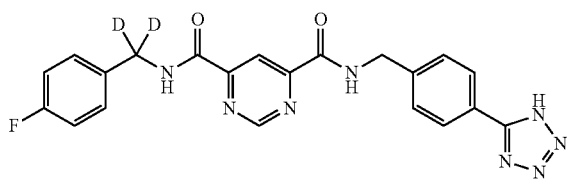 [SMILES: [2H]C([2H])(NC(=O)c1cc(C(=O)NCc2ccc(-c3nnn[nH]3)cc2)ncn1)c1ccc(F)cc1] |

| Ex. | Diamide Pyrimidine Examples D | Diamide Pyrimidine Examples E |
|---|---|---|
| 93 | | |
| 94 | | |
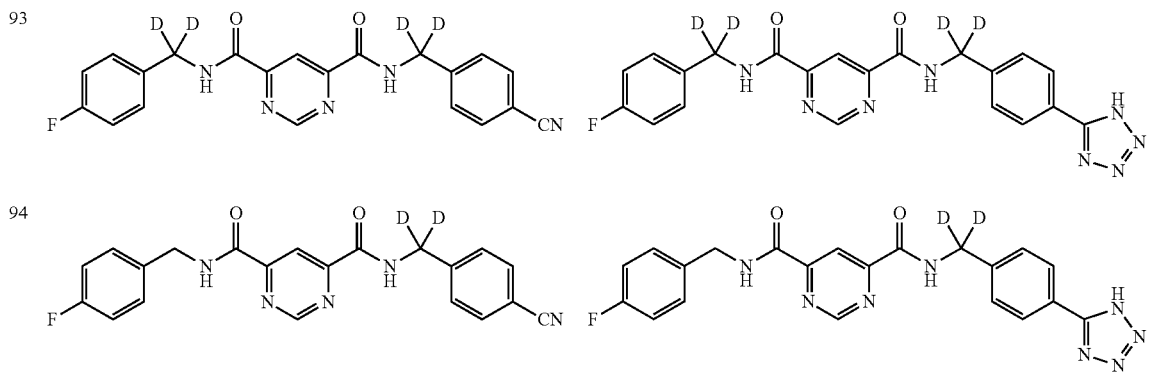
Examples 95-103
If one were to follow a similar procedure as that described in Example 33 using the Pyrimidine (D) to give the resulting Acid (F) one would obtain compounds as indicated in the table below.
| Ex. | Diamide Pyrimidine Examples D | Diamide Pyrimidine Examples F |
|---|---|---|
| 95 | | |
| 96 | | |
| 97 | | |
| 98 | | |
| 99 | | |
| 100 | | |
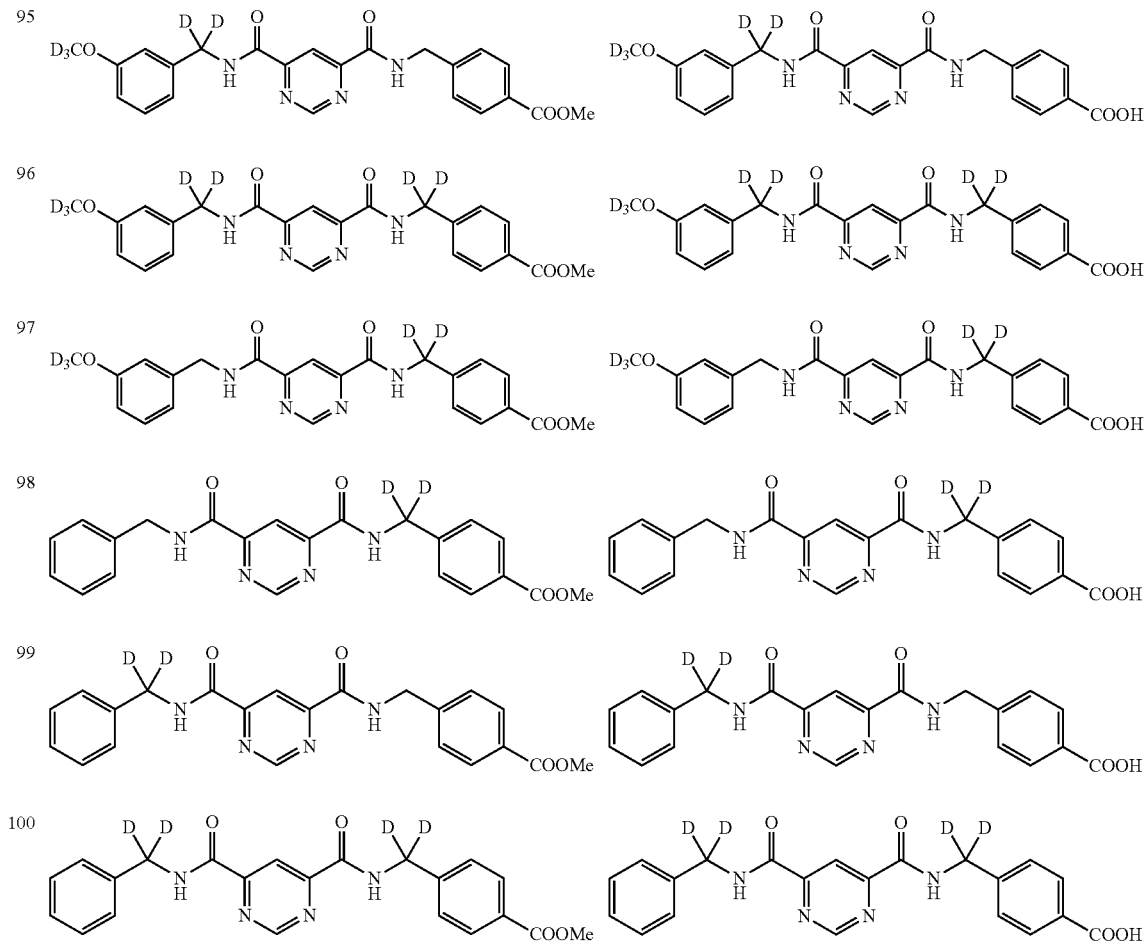

| Ex. | Diamide Pyrimidine Examples D | Diamide Pyrimidine Examples F |
|---|---|---|
| 101 | 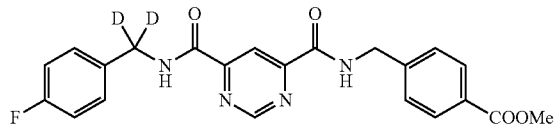 [SMILES: [2H]C([2H])(NC(=O)c1cc(C(=O)NCc2ccc(C(=O)OC)cc2)ncn1)c1ccc(F)cc1] | 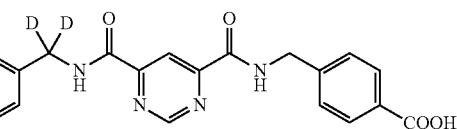 |
| 102 | 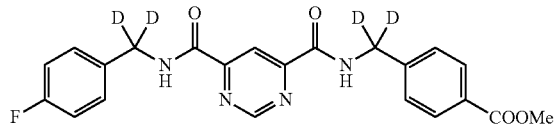 [SMILES: [2H]C([2H])(NC(=O)c1cc(C(=O)NC([2H])([2H])c2ccc(C(=O)OC)cc2)ncn1)c1ccc(F)cc1] | 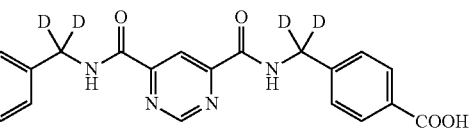 |
| 103 | 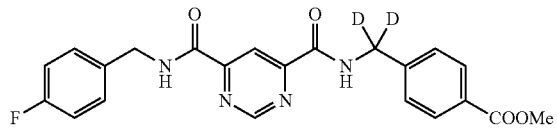 [SMILES: [2H]C([2H])(NC(=O)c1cc(C(=O)NCc2ccc(F)cc2)ncn1)c1ccc(C(=O)OC)cc1] | 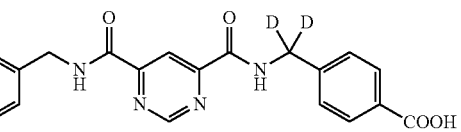 |

Example 104-117

If the Diamide Pyrimidine Acid compounds (F) and diethylamine were coupled in the presence of (Benzotriazole-1-yl-oxy-tris-(dimethylamino)-phosphonium hexafluorophosphate) (PyBop) or the reagents, HATU and HOAT at room temperature in dry THF one could obtain after column chromatography or Prep TLC the resulting amide compound (G) indicated in the table below.

| Ex. | Diamide Pyrimidine Acid Examples F | Diamide Pyrimidine amide Examples G |
|---|---|---|
| 104 | 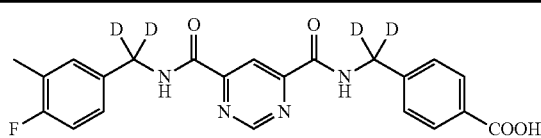 | 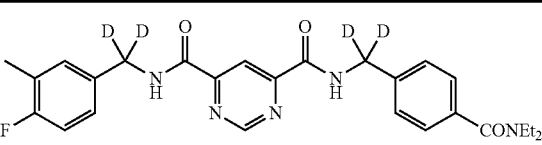 |
| 105 | 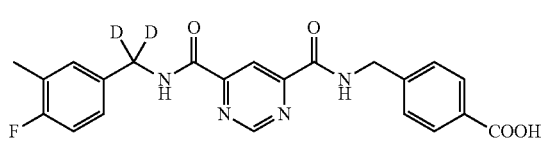 [SMILES: [2H]C([2H])(NC(=O)c1cc(C(=O)NCc2ccc(C(=O)O)cc2)ncn1)c1ccc(F)c(C)c1] | 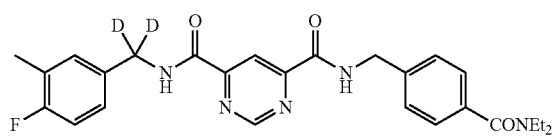 |
| 106 | 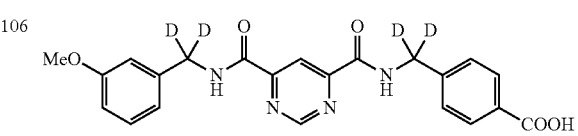 | 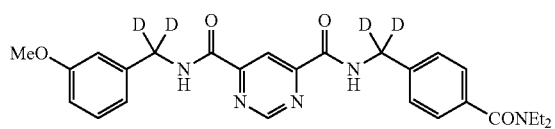 |
| 107 | 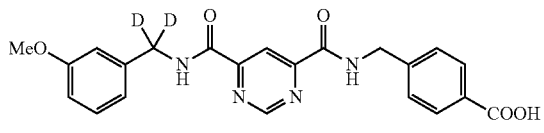 [SMILES: [2H]C([2H])(NC(=O)c1cc(C(=O)NCc2ccc(C(=O)O)cc2)ncn1)c1cccc(OC)c1] | 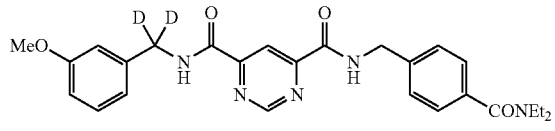 |
| 108 | 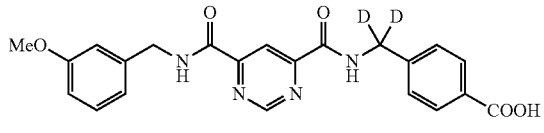 [SMILES: [2H]C([2H])(NC(=O)c1cc(C(=O)NCc2cccc(OC)c2)ncn1)c1ccc(C(=O)O)cc1] | 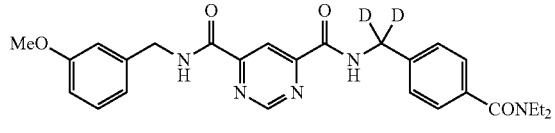 |
| 109 | 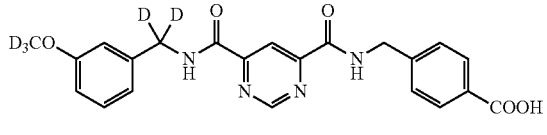 | 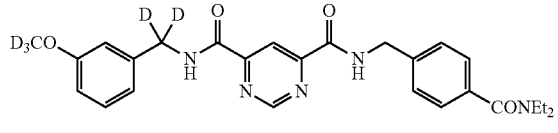 |

| Ex. | Diamide Pyrimidine Acid Examples F | Diamide Pyrimidine amide Examples G |
|---|---|---|
| 110 | 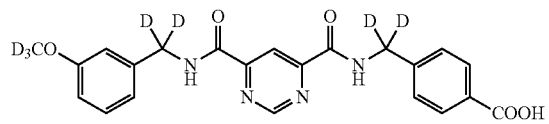 | 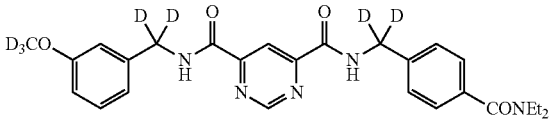 |
| 111 | 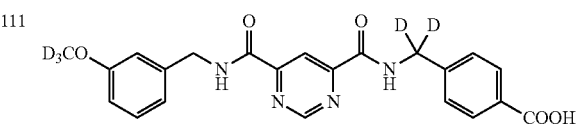 | 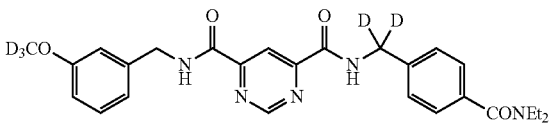 |
| 112 | 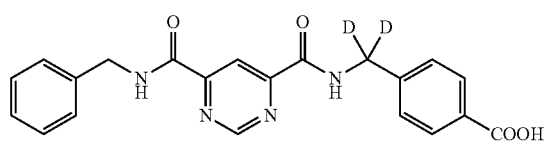 [SMILES: [2H]C([2H])(NC(=O)c1cc(C(=O)NCc2ccccc2)ncn1)c1ccc(C(=O)O)cc1] | 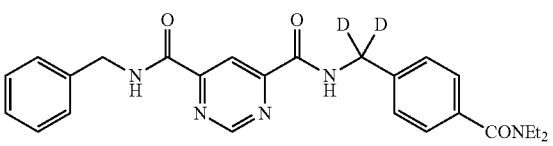 |
| 113 | 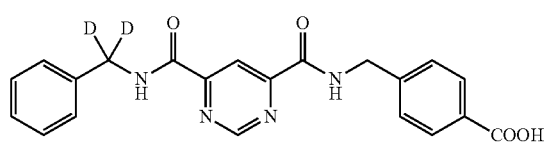 [SMILES: [2H]C([2H])(NC(=O)c1cc(C(=O)NCc2ccc(C(=O)O)cc2)ncn1)c1ccccc1] | 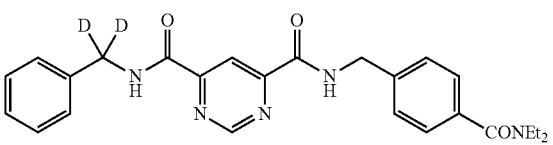 |
| 114 | 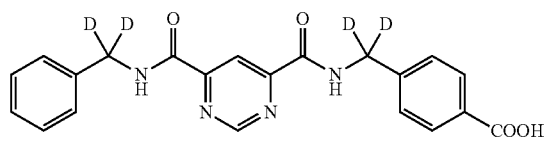 [SMILES: [2H]C([2H])(NC(=O)c1cc(C(=O)NC([2H])([2H])c2ccc(C(=O)O)cc2)ncn1)c1ccccc1] | 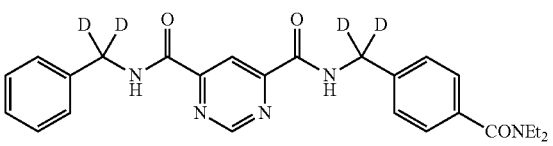 |
| 115 | 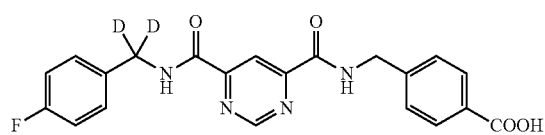 [SMILES: [2H]C([2H])(NC(=O)c1cc(C(=O)NCc2ccc(C(=O)O)cc2)ncn1)c1ccc(F)cc1] | 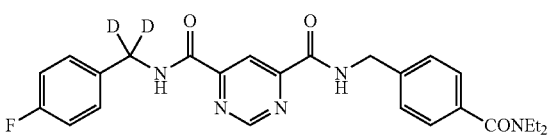 |
| 116 | 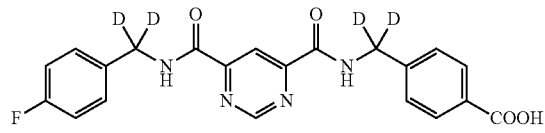 [SMILES: [2H]C([2H])(NC(=O)c1cc(C(=O)NC([2H])([2H])c2ccc(C(=O)O)cc2)ncn1)c1ccc(F)cc1] | 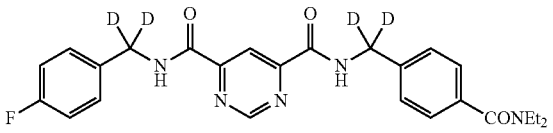 |
| 117 | 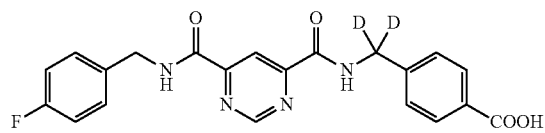 [SMILES: [2H]C([2H])(NC(=O)c1cc(C(=O)NCc2ccc(F)cc2)ncn1)c1ccc(C(=O)O)cc1] | 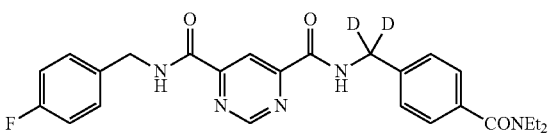 |

Example 118

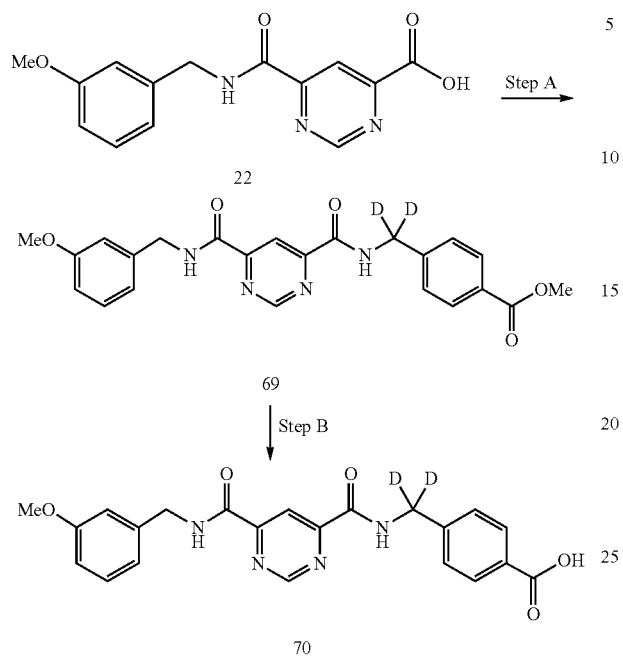

Step A

To a round bottom flask containing a stir bar and 6-(3-Methoxy-benzylcarbamoyl)-pyrimidine-4-carboxylic acid (22) (0.05 grams, 0.17 mmole) was added 4-(Amino-dideutero-methyl)-benzoic acid methyl ester (8) as the hydrochloride salt (synthesized via Example 3) (0.19 mmole), 1-hydroxy-7-azabenzotriazole (0.20 mmol) (HOAT) and 2-(7-azabenzotriazole-1-yl)-N—N—N—N-tetramethyluronium-hexafluorophosphate (HATU) (0.21 mmol). To the mixture was then added 1 ml of anhydrous dimethylformamide (DMF) and mixture stirred for a few minutes. Then N-methylmorpholine (NMP) (0.71 mmole) was then added and mixture stirred under nitrogen for 24 hours. The volatile components were then removed under reduced pressure to give a oil residue which was purified by column chromatography (SiO2, 0-40% ethyl acetate:hexane) to give 43 milligrams (57%) of 4-(Dideutero-{[6-(3-methoxy-benzyl-carbamoyl)-pyrimidine-4-carbonyl]-amino}-methyl)-benzoic acid methyl ester (69). $^1$H NMR (300 MHz, CDCl$_3$) δ 3.80 (s, 3H), 3.91 (s, 3H), 4.66 (d, 2H, J=6.3 Hz), 4.75 (d, 2H, J=6.0 Hz), 6.85-6.95 (m, 3H), 7.25-7.31 (m, 1H), 7.42 (d, 2H, J=8.4 Hz), 8.03 (d, 2H, J=8.4 Hz), 8.23 (br s, 1H), 8.30 (br s, 1H), 8.95 (s, 1H), 9.19 (s, 1H). LC-MS (M+H) 437.

Step B

To a 10 ml round bottom flask containing 43 mg (0.1 mmole) of 4-(Dideutero-{[6-(3-methoxy-benzylcarbamoyl)-pyrimidine-4-carbonyl]-amino}-methyl)-benzoic acid methyl ester (69) was added a stir bar and 1 ml of tetrahydrofuran (THF) and mixture stirred until solution was complete. To the solution was then added 1 ml of CD$_3$OD, 0.1 ml solution of 40% of NaOD in D$_2$O (commercially obtained from Cambridge Isotope Laboratories) and 0.5 ml of D$_2$O (obtained from Cambridge Isotope Laboratories) and mixture stirred for 2.5 hours. To the mixture was then added 3 ml of a solution composed of 4 M HCl in dioxane. The volatile components of the reaction mixture were then removed under reduced pressure to give a white solid. To the solid was added 2 ml of H$_2$O and mixture triturated and resulting solid residue dried under pump vacuum to give a white solid which was purified by preparative thin layer chromatography (prep-TLC) (SiO$_2$, 10% methanol in methylene chloride) to isolate 20 mg (48%) of 4-(Diduetero-{[6-(3-methoxy-benzylcarbamoyl)-pyrimidine-4-carbonyl]-amino}-methyl)-benzoic acid (70) as a white solid. (R$_f$=0.4, SiO$_2$, 10% methanol in methylene chloride), $^1$H NMR (300 MHz, d6-DMSO) δ 3.70 (s, 3H), 4.47 (d, 2H, J=6.3 Hz), 6.75-6.90 (m, 3H), 7.18-7.22 (m, 3H), 7.78 (d, 2H, J=8.1 Hz), 8.45 (s, 1H), 9.44 (s, 1H), 9.61-9.65 (m, 2H). LC-MS (M+H) 423.

Example 150

In-Vitro Assay for Determining Microsomal Stability of Select Compounds in Human and Rat Microsomes Human and Rat microsomal stability was determined for select compounds following the method of Houston (Houston, J B; Biochem. Pharmacol. 47, (1994), 1469). 1 μM concentration of compound and separate human and Rat microsomes (0.3 mg/mL, BD bioscience) were used in the in-vitro assay. To ensure proper energy supply for microsomal degradation of compound, an energy regenerating system comprised of 100 mM potassium phosphate, 2 mM NADPH, 3 mM MgCl$_2$, pH=7.4 and the microsomal protein is added to each sample and the resulting suspension is then incubated in duplicate for 60 min at 37° C. in a rotary shaker. A control is run for each test agent in duplicate omitting NADPH to detect NADPH-free degradation. At T=0 and T=60 min., an aliquot is removed from each experimental and control reaction and then mixed with an equal volume of ice-cold Stop Solution (consisting of 0.3% acetic acid in acetonitrile containing haloperidol and diclofenac as internal standards). Stopped reactions are then incubated for at least ten minutes at −20° C., and an additional volume of water is then added. The samples are then centrifuged to remove precipitated protein, and the supernatants are then analyzed by LC-MS/MS to determine the percentage of compound remaining. The LC-MS/MS system used was an Agilent 6410 mass spectrometer coupled with an Agilent 1200 HPLC and a CTC PAL chilled autosampler, all controlled by MassHunter software (Agilent), or an ABI2000 mass spectrometer coupled with an Agilent 1100 HPLC and a CTC PAL chilled autosampler, all controlled by Analyst software (ABI). After separation on a C18 reverse phase HPLC column (Agilent, Waters, or equivalent) using an acetonitrile-water gradient system, peaks were analyzed by mass spectrometry (MS) using ESI ionization in MRM mode. Verapamil (high metabolized) and Warfarin (low metabolized) are used as controls to test the activity of the microsomal proteins. Table 15 and 16 below show the microsomal stability of select compounds in both human and Rat microsomes.

TABLE 15
In-vitro Human Microsomal Stability Of Select Compounds.
| Compound Structure & ID # | Compound Concentration (microMoles) | Test Species | Mean Remaining Parent with NADPH (%)[1] |
|---|---|---|---|
| 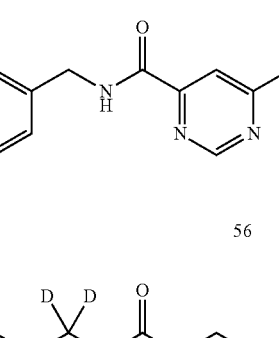 45 | 1 | Human | 103 |
| 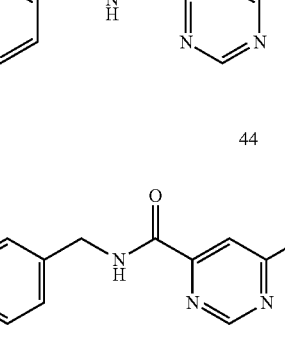 56 | 1 | Human | 104 |
| 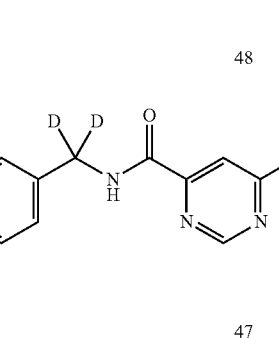 44 | 1 | Human | 95.6 |
| 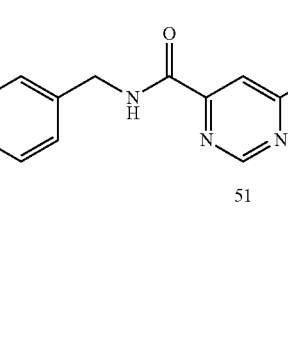 48 | 1 | Human | 88.1 |
|  47 | 1 | Human | 95.3 |
| 51 | 1 | Human | 5.3 |

TABLE 15-continued

In-vitro Human Microsomal Stability Of Select Compounds.

| Compound Structure & ID # | Compound Concentration (microMoles) | Test Species | Mean Remaining Parent with NADPH (%)[1] |
|---|---|---|---|
| 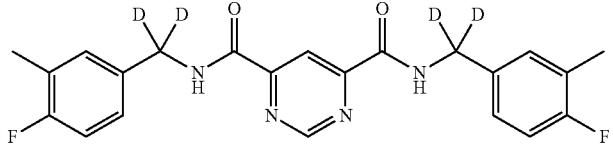<br>49 | 1 | Human | 5.5 |

[1] at T = 60 minutes

TABLE 16

In-vitro Rat Microsomal Stability Of Select Compounds.

| Compound Structure & ID # | Compound Concentration (microMoles) | Test Species | % Mean Remaining Parent with NADPH (%)[1] |
|---|---|---|---|
| 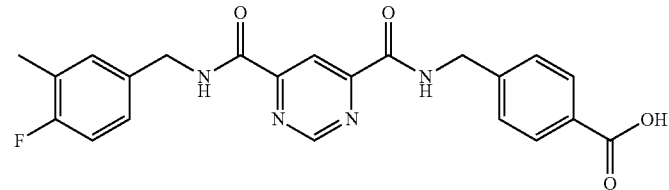<br>45 | 1 | Rat | 90.7 |
| 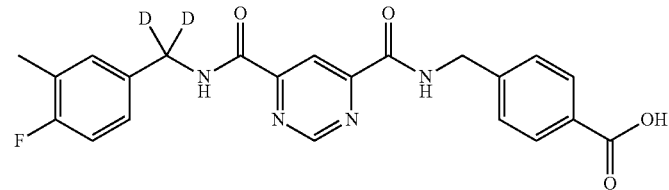<br>44 | 1 | Rat | 87.4 |
| 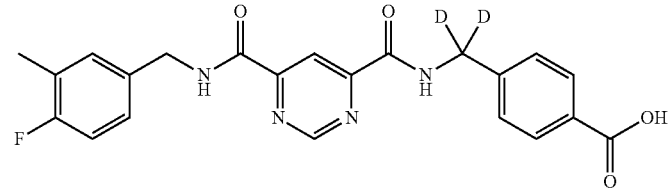<br>56 | 1 | Rat | 98.5 |
| 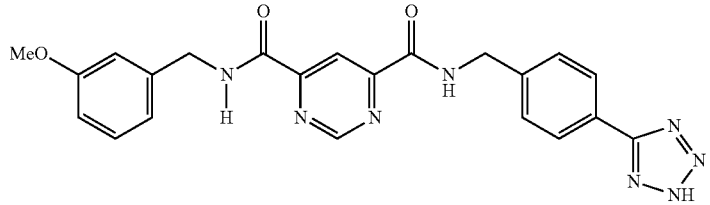<br>48 | 1 | Rat | 52.8 |

TABLE 16-continued

In-vitro Rat Microsomal Stability Of Select Compounds.

| Compound Structure & ID # | Compound Concentration (microMoles) | Test Species | % Mean Remaining Parent with NADPH (%)[1] |
|---|---|---|---|
| ![compound 47] 47 | 1 | Rat | 57.4 |
| ![compound 51] 51 | 1 | Rat | 0.6 |
| ![compound 49] 49 | 1 | Rat | 1.7 |

[1] at T = 60 minutes

Example 160

Assay for Determining MMP-2 Inhibition

MMP-2 inhibitor activity was carried out via the method of Knight (Knight, C. G. et. al, *FEBS LETT.* 296 (3), (1992), 263-266), using an assay buffer comprised of 50 mM Tris-HCl, pH 7.6, 200 mM NaCl, 5 mM $CaCl_2$ and 1 µM $ZnSO_4$. A concentration of MMP inhibitor of the present invention was tested (10 microMolar) in duplicate runs. Catalytic domain of MMP-2 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was then started by the addition of 10 µM of fluorescent substrate Mca-P-L-G-L-Dpa-A-R-NH2 (Kd ~8 microMolar). The fluorescent product, McaPLG, was then measured at excitation of 355 nm and emission 405 nm by an automatic plate multireader at 37° C. A positive control was separately run using the broad spectrum MMP inhibitor GM6001 as a control compound (MMP-2 IC50=0.5 nanoMolar). Any inhibition <50% is considered not active under these assay conditions. Table 17 summarizes the results of the inhibition study.

TABLE 17

Percent MMP-2 Inhibition (Inhibition <50% is considered not active).

| Compound Structure/ID# | Compound Concentration | Substrate | Substrate Concentration | Average Percent Inhibition |
|---|---|---|---|---|
|  44 | 10 microMolar | Mca-P-L-G-L-Dpa-A-R-NH2 | 10 microMolar | 8.19% |

Example 161

Assay for Determining MMP-9 Inhibition

MMP-9 inhibitor activity was carried out via the method of Bickett, D. M.; (Bickett, D. M., et al *Analytical Biochemistry* 212, (1993), 58-64), using an assay buffer comprised of 50 mM Tris-HCl, pH 7.6, 200 mM NaCl, 5 mM CaCl$_2$ and 1 μM ZnSO4. A concentration of MMP inhibitor of the present invention was tested (10 microMolar) in duplicate runs. Catalytic domain of MMP-9 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was then started by the addition of 10 μM of fluorescent substrate DNP-Pro-Cha-Gly-Cys(Me)-His-Ala-Lys(N-Me-Abz)-NH2 [Cha=β-cyclohexylalanyl; Abz=2-aminobenzoyl(anthraniloyl)] (Kd ~7 microMolar). The fluorescent product, DnpPChaG, was then measured at excitation of 365 nm and emission 450 nm by an automatic plate multireader at 37° C. A positive control was separately run using the broad spectrum MMP inhibitor GM6001 as a control compound (MMP-9 IC50=0.2 nanoMolar). Any inhibition <50% is considered not active under these assay conditions. Table 18 summarizes the results of the inhibition study.

TABLE 18

Percent MMP-9 Inhibition (Inhibition <50% is considered not active).

| Compound Structure/ID# | Compound Concentration | Substrate | Substrate Concentration | Average Percent Inhibition |
|---|---|---|---|---|
| (structure) 44 | 10 microMolar | DNP-Pro-Cha-Gly-Cys(Me)-His-Ala-Lys(N-Me-Abz)-NH2 | 10 microMolar | 2.39% |

Example 162

Assay for Determining MMP-1 Inhibition

MMP-1 inhibitor activity of the MMP inhibitors of the present invention was carried out via the method of Knight (Knight, C. G. et. al, *FEBS LETT.* 296 (3), (1992), 263-266), using an assay buffer comprised of 50 mM Tris-HCl, pH 7.6, 200 mM NaCl, 5 mM CaCl$_2$ and 1 μM ZnSO4. A concentration of MMP inhibitor of the present invention was tested (10 microMolar) in duplicate runs. Catalytic domain of MMP-1 (human recombinant) enzyme was added to the compound solution. The mixture of enzyme and compound in assay buffer was then thoroughly mixed and incubated for 60 minutes at 37° C. Upon the completion of incubation, the assay was then started by the addition of 10 μM of fluorescent substrate DNP-Pro-Cha-Gly-Cys(Me)-His-Ala-Lys(N-Me-Abz)-NH2 [Cha=β-cyclohexylalanyl; Abz=2-aminobenzoyl(anthraniloyl)] (10 μM). The fluorescent product, DnpPChaG, was then measured at an excitation wavelength of 365 nm and emission wavelength of 450 nm using an automatic plate multireader at 37° C. A positive control was also run separately using the broad spectrum MMP inhibitor Tyr-hydroxamic acid as a control compound. Any inhibition <50% is considered not active under these assay conditions. Table 19 summarizes the results of the inhibition study.

TABLE 19

Percent MMP-1 Inhibition (Inhibition <50% is considered not active).

| Compound Structure/ID# | Compound Concentration | Substrate | Substrate Concentration | Average Percent Inhibition |
|---|---|---|---|---|
| (structure) 44 | 10 microMolar | DNP-Pro-Cha-Gly-Cys(Me)-His-Ala-Lys(N-Me-Abz)-NH2 | 10 microMolar | 1.83% |

Example 163

Assay for Determining MMP-7 Inhibition

If one were interested in measuring the MMP-7 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 µM ZnSO4 is used. A single concentration could be tested (i.e., 1 microMolar) in duplicate runs. Catalytic domain of MMP-7 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 µM of fluorescent substrate Mca-P-L-G-L-Dpa-A-R-NH2. The fluorescent product, McaPLG, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

Example 164

Assay for Determining MMP-3 Inhibition

MMP-3 inhibitor activity of the MMP inhibitors of the present invention was carried out via the method of Knight (Knight, C. G. et. al, *FEBS LETT.* 296 (3), (1992), 263-266), using an assay buffer comprising of 50 mM Tris-HCl, pH 7.6, 200 mM NaCl, 5 mM $CaCl_2$ and 1 µM ZnSO4. A concentration of MMP inhibitor of the present invention was tested (10 microMolar) in duplicate runs. Catalytic domain of MMP-3 (human recombinant) enzyme was then added to the compound solution. The mixture of enzyme and compound in assay buffer was then thoroughly mixed and incubated for 60 minutes at 37° C. Upon the completion of incubation, the assay was then started by the addition of 10 µM of fluorescent substrate McaRPKPVENValWRK(Dnp)NH$_2$. The fluorescent product, McaRPK, was then measured at an excitation wavelength of 355 nm and emission wavelength of 405 nm using an automatic plate multireader at 37° C. A positive control was then run separately using the broad spectrum MMP inhibitor Tyr-hydroxamic acid as a control compound. Any inhibition <50% is considered not active under these assay conditions. Table 20 summarizes the results of the inhibition study.

TABLE 20

Percent MMP-3 Inhibition (Inhibition <50% is considered not active).

| Compound Structure/ID# | Compound Concentration | Substrate | Substrate Concentration | Average Percent Inhibition |
| --- | --- | --- | --- | --- |
| 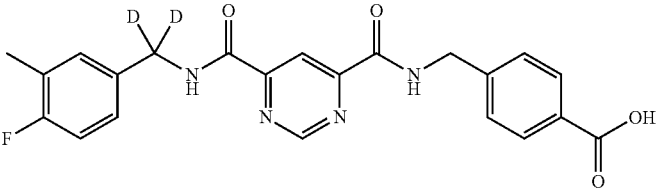<br>44 | 10 microMolar | McaRPKVE NvalWRK (Dnp)NH$_2$ | 10 microMolar | 1.31% |

Example 165

Assay for Determining MMP-12 Inhibition

MMP-12 inhibitor activity was carried out by first separating the cleaved and uncleaved substrates by charge via electrophoretic mobility shift and then measuring the fluorescence of the separated products and comparing them with control reactions to determine inhibition of enzyme activity. The MMP-12 assay was then run using an assay buffer comprising of 100 mM HEPES, pH 7.5, 0.01% Brij-35, 1.5 mM NaCl and 2 mM $CaCl_2$. A concentration of MMP inhibitor of the present invention was tested (10 microMolar) in duplicate runs. The reaction was started by first adding the substrate and then incubating the reaction mixture for 1 hour at room temperature. The reaction was then terminated via the addition of a stop buffer consisting of 100 mM HEPES (pH 7.5), 30 mM EDTA, 0.015% Brij-35, and 5% DMSO. A positive control was separately run using the broad spectrum MMP inhibitor GM6001 as a control compound. Any inhibition <50% is considered not active under these assay conditions. Table 21 summarizes the results of the inhibition study.

TABLE 21

Percent MMP-12 Inhibition (Inhibition <50% is considered not active).

| Compound Structure/ID# | Compound Concentration | Substrate | Substrate Concentration | Average Percent Inhibition |
|---|---|---|---|---|
| 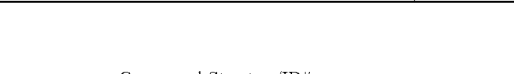<br>44 | 10 microMolar | Fluorescein-labeled peptide | 4 microMolar | 0.68% |

Example 166

Assay for Determining MMP-13 Inhibition

MMP-13 inhibitor activity of the MMP inhibitors of the present invention was measured using the method of Knight (Knight, C. G. et. al, *FEBS LETT.* 296 (3), (1992), 263-266), using an assay buffer comprising of 50 mM Tris-HCl, pH 7.6, 200 mM NaCl, 5 mM $CaCl_2$ and 1 μM ZnSO4. A concentration of MMP inhibitor of the present invention was tested (1 microMolar) in duplicate runs. Catalytic domain of MMP-13 (human recombinant) enzyme was then added to the compound solution. The mixture of enzyme and compound in assay buffer was then thoroughly mixed and incubated for 60 minutes at 37° C. Upon the completion of incubation, the assay was then started by the addition of 10 μM of fluorescent substrate Mca-P-L-G-L-Dpa-A-R-NH2. The fluorescent product, McaPLG, was then measured at an excitation wavelength of 355 nm and emission wavelength of 405 nm using an automatic plate multireader at 37° C. A positive control was also run separately using the broad spectrum MMP inhibitor GM6001 as a control compound. Any inhibition <50% is considered not active under these assay conditions. Table 22 summarizes the results of the single concentration inhibition study. The time-dependent increase in fluorescence is measured at the 355 nm excitation and 405 nm emission by automatic plate multireader. The $IC_{50}$ values for MMP-13 inhibition are then calculated from the initial reaction rates Inhibition activity of some highly potent compounds of the present invention are summarized in Table 23.

TABLE 22

Percent MMP-13 Inhibition (Inhibition <50% is considered not active).

| Compound Structure/ID# | Compound Concentration | Substrate | Substrate Concentration | Average Percent Inhibition |
|---|---|---|---|---|
| 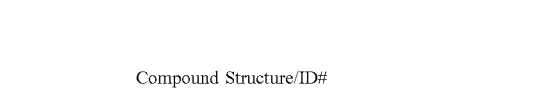<br>47 | 1 microMolar | Mca-P-L-G-L-Dpa-A-R-NH2 | 10 microMolar | 92.0% |

TABLE 23

MMP-13 IC50 Determination of Select Compounds.

| Compound Structure/ID# | $IC_{50}$ (nM) |
|---|---|
| 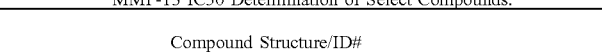<br>44 | <100 nM |

TABLE 23-continued

MMP-13 IC50 Determination of Select Compounds.

| Compound Structure/ID# | IC$_{50}$ (nM) |
|---|---|
| 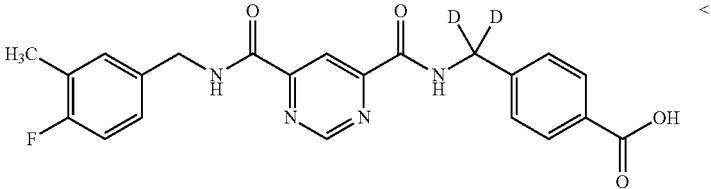 56 | <100 nM |
| 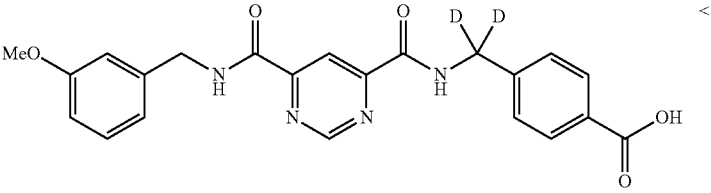 70 | <100 nM |

Example 170

In Vivo Rat Pharmacokinetics (PK) of Select Compounds

Understanding the pharmacokinetics of a test article in species typically employed in preclinical testing is an essential component of drug discovery. Select compounds of the present invention were orally dosed in rats in order to determine their relative bioavailablility.

Procedure:

Six (6) male Lewis rats were used. Fasting was conducted at least 16 hours prior to dose administration. Food was returned at approximately 4 hours post dose. The animals were placed into 2 groups of 3 animals per group. The oral (PO) formulation for Groups 1 & 2 were prepared on the day of dosing at a target concentration of 0.5 mg/mL in 0.5% Methylcellulose (400 cps) to produce a white, homogeneous suspension. Dosing was performed as outlined in Table 24:

TABLE 24

In vivo Rat PK Study Protocol via Oral (PO) Administration of Select MMP Inhibitors.

| Group | No. of Male Rats | Compound Structure/ID# | Dose (mg/Kg) | Dose Volume (mL/kg) | Vehicle | Route |
|---|---|---|---|---|---|---|
| 1 | 3 | 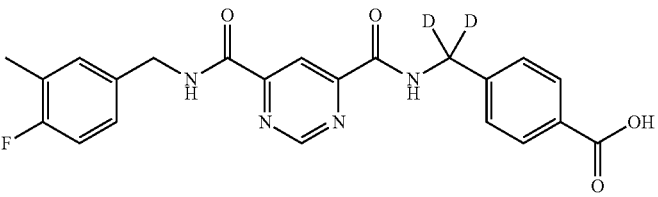 56 | 1.0 | 2 | 0.5% MC | PO |
| 2 | 3 | 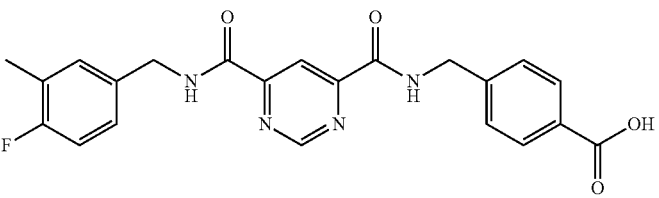 45 | 1.0 | 2 | 0.5% MC | PO |

Conc. = concentration;
MC = Methylcellulose;
PO = oral by gavage

Each animal in Group 1 received prepared compound (56) by oral dose administration at a target dose level of 1.0 mg/kg and at a dose volume of 2 mL/kg. Each animal in Group 2 received prepared compound (45) by oral dose administration at a target dose level of 1.0 mg/kg and at a dose volume of 2 mL/kg (Table 24). Whole blood samples (0.250 mL; $K_2$EDTA anticoagulant) were collected from each animal through a jugular vein catheter. Whole blood samples were collected from all animals pre-dose, and at 0.25, 0.5, 1, 2, 4, 8, 16, and 24 hours after dose administration. All blood samples were immediately placed on ice until processing. Whole blood samples were centrifuged at 2200×g for 10 minutes in a refrigerated centrifuge (5±3° C.) to isolate plasma. The plasma samples were transferred to individual polypropylene vials and immediately placed on dry ice before storage at nominally −20±5° C. The plasma samples some time later were then thawed and extracted and analyzed by high pressure liquid chromatography (HPLC) coupled to Mass Spectrometery (MS) (Table 25). Pharmacokinetic parameters (Table 25) were estimated using WinNonlin® pharmacokinetic software (Version No. 5.2.1) using a non-compartmental approach consistent with the PO route of administration. Pharmacokinetic results of select compounds are presented in Table 26.

TABLE 25

Definition of PK Parameters & HPLC-MS Conditions.

| Parameter | Description of Parameter or Conditions |
|---|---|
| AUC(0-t) | The area under the concentration versus time curve from time zero to the time after dosing at which the last quantifiable concentration of the drug was observed; estimated by the linear or linear/log trapezoidal method. |
| T½ | The apparent terminal elimination half life. |
| AUC(0-inf) | The area under the arithmetic mean concentration versus time curve from time zero to infinity. |
| Cmax | Maximum observed concentration, occurring at Tmax. |
| Tmax | Time of maximum observed concentration. For non-steady state data, the entire curve is considered. |
| LC Conditions & MS Instrument | Agilent 1200 Series Binary Pump, Leap CTC PAL autosampler, supelco Discovery C18 column (50 × 2.1 mm), mobile phase: water (0.1% formic acid) and acetonitrile (0.1% formic acid); A 1.0 min gradient was utilitized going from 1% to 98% of Mobile Phase B for a total run time of 2.40 minutes. The mass spectrometer was a API 5000 |

TABLE 26

Mean PK Results for Oral (PO) Administration of Select Compounds in Male Lewis Rats.

| Compound Structure/ID# | Dose level (mg/kg) | AUC(0-t) (ng•hr/mL) | AUC (0-inf) (ng•hr/mL) | T1/2 (hr) | Cmax (ng/mL) | Tmax (hr) |
|---|---|---|---|---|---|---|
| 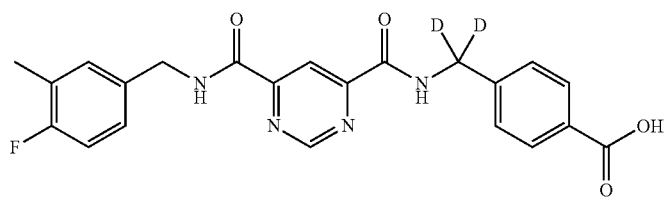 56 | 1.0 | 697 | 705 | 1.22 | 362 | 0.75 |
| 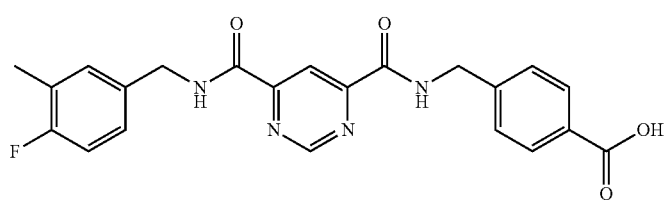 45 | 1.0 | 414 | 428 | 1.84 | 310 | 0.41 |

Example 200

Measuring Inflammatory Pain Inhibition-Carrageena (CARR)-Induced Inflammation in Rats If one were to measure the inflammatory pain inhibiting affects of the MMP inhibitors of the present invention, one could use the Carrageenan model for measuring neuropathic pain as presented in LaBuda, C. J., and Fuchs, P. N. Neuroscience Letters, 304, (2001), 137-140.

Acute Model:

Subcutaneous injection into the hind paw of a rat: An acute inflammatory condition is produced by a subcutaneous injection of 3% lambda Carrageenan (0.12 ml) into the plantar surface of one hind paw under light isoflurane anesthesia. Usually, there is an additional control group that receives an equal volume of saline Animals would then receive the MMP inhibitors of the present invention 3½ hours after the CARR injection, The MMP inhibitor can be given orally (PO), by Intraarticular (IA) injection or using a transdermal delivery system (TDS) as taught by Paudel (Paudel, K. S. et al. Ther. Deliv. 1(1), 109-131, (2010)). Transdermal skin permeation of the MMP-13 inhibitor can be applied passively using patches and/or by using chemical (i.e. liposomes, alcohol et al.) or mechanical (i.e. low and high frequency ultrasound) enhancers which enhance the permeation of the compound through the skin. Quantification of pain behavior could then be measured via incapacitance meter. Following the procedure of Bove and coworkers (Bove S E, Calcaterra S L, Brooker R M, Huber C M, Guzman R E, Juneau P L et al. Osteoarthritis Cartilage 11(11), 821-30, (2003)), animals can be placed in a plexiglass housing of the incapacitance meter and allowed to acclimate for 5 minutes. The position of the animal can be such that each hind paw rests on a separate force plate. The force exerted by each hind paw can be averaged over a 1-2 second interval, and the mean of three readings can constitute 1 data point. The data can be expressed as absolute right vs. left hind paw, the ratio of right/left and the % total right hind paw load bearing weight.

Chronic Model:

Intra-articular injection. A longer lasting state of inflammation is produced by performing intra-articular injection of CARR (0.1 ml, 3%) into the tibial joint under isoflurane anesthesia. This route of administration induces an inflammatory condition that can last for up to 7 days following injection and is an established model of arthritic inflammatory pain. Quantification of pain behavior could then be measured via incapacitance meter.

Example 201

Medial Meniscal Tear (MMT) Rat Model Of OA

The Medical Mensical Tear (MMT)-rat model is one of the more popular surgical models that mimic post-traumatic OA in humans by destabilizing the joint and therefore is directly relevant to the study of OA & OA-induced pain (Janusz, M. J.; Bendele, A. M et al. Osteoarthritis Cartilage, 10, 785-91, (2002). Bove and coworkers (Bove, S. E. et al. Osteoarthritis Cartilage, 14, 1041-1048, (2006)) report the development of tactile allodynia following MMT surgery.

MMT Protocol:

If one were interested in performing the MMT-rat model in order to test the bioactivity of the MMP inhibitors of the present invention, one would take Male Lewis rats (10 per group) weighing 170-200 grams each and anesthetize them with isoflurane in order to prepare them for surgery. A skin incision can then be made over the medial aspect of the right knee joint, and the medial collateral ligament can then be exposed by blunt dissection. Then the meniscus can be cut through the full thickness to simulate a complete tear. Skin and subcutis would then be sutured closed. Once-daily oral dosing of a vehicle group, an NSAID (positive control) group and a MMP inhibitor group of the present invention would be initiated the day after surgery and continued for 28 days after surgery. In addition to oral dosing, one can also look at Intraarticular (IA) injection and/or the use of a transdermal delivery system (TDS). If done intraarticularly it would be done by the injection of a vehicle group, a Synvisc® (a hyaluronic acid as a positive control) group and a group taking the MMP inhibitor of the present invention on the day after surgery and repeated every four days for 28 days after surgery. If done using TDS one would have the same groups as when dosing IA but would apply the materials (i.e. vehicle, hyaluronic acid, steroid or MMP-13 inhibitor) transdermally using a batch or in combination with chemical or mechanical enhancers. The animals could be bled via the tail vein in order to collect plasma on day-1 and day 27 for biomarker analysis. Pain read-out could involve incapacitance (every other day), von Frey (every other day) and gait (twice/week) testing. At the end of the study the animals could then be euthanized, and the right knees collected for histopathologic evaluation of chondroprotective effects.

What is claimed is:

1. A compound according to Formula (I):

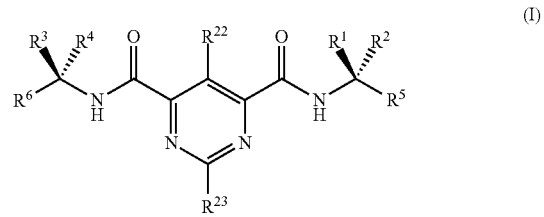

wherein:
$R^5$ and $R^6$ are independently selected from the group consisting of alkyl, alkenyl, alkynyl, cycloalkyl, heterocyclyl, aryl, and heteroaryl, wherein alkyl, alkenyl, alkynyl, cycloalkyl, heterocyclyl, aryl, and heteroaryl are optionally substituted one or more times and wherein two substituents in the cycloalkyl-, aryl-, or heteroarylring when taken together with the nitrogen or carbon to which they are attached optionally complete an additional 3- to 8-membered ring containing carbon atoms and optionally containing one or more heteroatoms selected from O, $SO_x$, or $NR^{50}$ and which is optionally substituted or partially saturated;

$R^1$, $R^2$, $R^3$, $R^4$ are independently selected from the group consisting of hydrogen, deuterium, alkyl, deuteroalkyl, $CD_3$, haloalkyl, fluoroalkyl, cycloalkyl, alkenyl, alkynyl, aryl, heteroaryl, cycloalkyl-alkyl, arylalkyl, heteroarylalkyl, $COOR^{10}$, $CONR^{10}R^{11}$, $SO_2R^{10}$ and $SO_2NR^{10}R^{11}$, wherein at least one or more of the groups $R^1$, $R^2$, $R^3$ $R^4$ is deuterium each with an isotopic enrichment that is ≥1%, and wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times;

$R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{22}$ and $R^{23}$ are independently selected from the group consisting of hydrogen, deuterium, halo, alkyl, deuteroalkyl, $CD_3$, cycloalkyl, hydroxy, alkoxy, aryl, heteroaryl, arylalkyl, heteroarylalkyl, alkenyl, alkynyl, $NO_2$, $NR^{10}R^{11}$, $NR^{10}NR^{10}R^{11}$, $NR^{10}N=CR^{10}R^U$, $NR^{10}SO_2R^{11}$, CN, $COOR^{10}$, and fluoroalkyl, wherein alkyl, cycloalkyl, alkoxy, alkenyl, alkynyl, and fluoroalkyl are optionally substituted;

$R^{50}$ is selected from the group consisting of hydrogen, deuterium, deuteroalkyl, $CD_3$, alkyl, aryl, heteroaryl, $C(O)R^{10}$, $C(O)NR^{10}R^{11}$, $SO_2R^{10}$ and $SO_2NR^{10}R^{11}$, wherein alkyl, aryl, and heteroaryl are optionally substituted;

x is selected from 0 to 2; or

N-oxides, pharmaceutically acceptable salts, formulations, polymorphs, tautomers, racemic mixtures, optically active enantiomers, diastereoisomers, or stereoisomers thereof.

2. A compound according to Formula (II):

(II)

wherein:

$R^7$ and $R^8$ are independently selected from the group consisting of hydrogen, deuterium, halo, alkyl, deuteroalkyl, $CD_3$, $CD_3O$, cycloalkyl, hydroxy, alkoxy, aryl, heteroaryl, arylalkyl, heteroarylalkyl, alkenyl, tetrazole, alkynyl, $NO_2$, $NR^{10}R^{11}$, $NR^{10}NR^{10}R^{11}$, $NR^{10}N=CR^{10}R^{11}$, $NR^{10}SO_2R^{11}$, CN, $COOR^{10}$, $CONR^{10}R^{11}$, $SO_2NR^{10}R^{11}$, $SO_2R^{10}$, $OC(O)R^{10}$, $OC(O)NR^{10}R^{11}$, $NR^{10}C(O)R^{11}$, $NR^{10}CO_2R^{11}$, $(C_0$-$C_6)$-alkyl-$C(=NR^a)NHR^b$, $(C_0$-$C_6)$-alkyl-NHC$(=NR^a)NHR^b$, $(C_0$-$C_6)$-alkyl-$C(O)OR^{10}$, $(C_0$-$C_6)$-alkyl-$C(O)NR^{10}R^{11}$, $(C_0$-$C_6)$-alkyl-$C(O)$—NH—CN, O—$(C_0$-$C_6)$-alkyl-$C(O)NR^{10}R^{11}$, $S(O)_x$—$(C_0$-$C_6)$-alkyl-$C(O)OR^{10}$, $S(O)_x$—$(C_0$-$C_6)$-alkyl-$C(O)NR^{10}R^{11}$, $(C_0$-$C_6)$-alkyl-$C(O)NR^{10}$—$(C_0$-$C_6)$-alkyl-$NR^{10}R^{11}$, $(C_0$-$C_6)$-alkyl-$NR^{10}R^{11}$, $(C_0$-$C_6)$-alkyl-$NR^{10}$—$C(O)R^{10}$, $(C_0$-$C_6)$-alkyl-$NR^{10}$—$C(O)OR^{10}$, $(C_0$-$C_6)$-alkyl-$NR^{10}$—$C(O)$—$NR^{10}R^{11}$, $(C_0$-$C_6)$-alkyl-$NR^{10}$—$SO_2NR^{10}R^{11}$, and fluoroalkyl, wherein alkyl, cycloalkyl, alkoxy, alkenyl, alkynyl, and fluoroalkyl are optionally substituted;

$R^7$ and $R^8$ when taken together with the aryl ring to which they are attached may complete a 3- to 8-membered ring containing carbon atoms and optionally containing a heteroatom selected from O, S, or $NR^{50}$ and which is optionally substituted;

$R^1$, $R^2$, $R^3$, $R^4$ are independently selected from the group consisting of hydrogen, and deuterium, alkyl, deuteroalkyl, $CD_3$, haloalkyl, fluoroalkyl, cycloalkyl, alkenyl, alkynyl, aryl, heteroaryl, cycloalkylalkyl, arylalkyl, heteroarylalkyl, $COOR^{10}$, $CONR^{10}R^{11}$, $SO_2R^{10}$ and $SO_2NR^{10}R^{11}$ $SO_2NR^{10}R^{11}$, wherein at least one or more of the groups $R^1$, $R^2$, $R^3$ $R^4$ is deuterium each with an isotopic enrichment that is ≥1%, and wherein alkyl, haloalkyl, fluoroalkyl, cycloalkyl, alkenyl, alkynyl, aryl, heteroaryl, cycloalkyl-alkyl, arylalkyl, and heteroarylalkyl are optionally substituted one or more times $R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{50}$ is selected from the group consisting of hydrogen, deuterium, deuteroalkyl, $CD_3$, alkyl, aryl, heteroaryl, $C(O)R^{10}$, $C(O)NR^{10}R^{11}$, $SO_2R^{10}$ and $SO_2NR^{10}R^{11}$, wherein alkyl, aryl, and heteroaryl are optionally substituted;

x is selected from 0 to 2; or

N-oxides, pharmaceutically acceptable salts, formulations, polymorphs, tautomers, racemic mixtures optically active enantiomers, diastereoisomers or stereoisomers thereof.

3. A compound according to claim 1, wherein $R^5$ and $R^6$ is selected from the group consisting of:

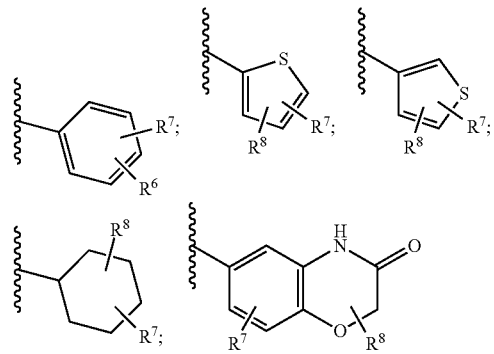

wherein
$R^7$ and $R^8$ is independently selected from the group consisting of

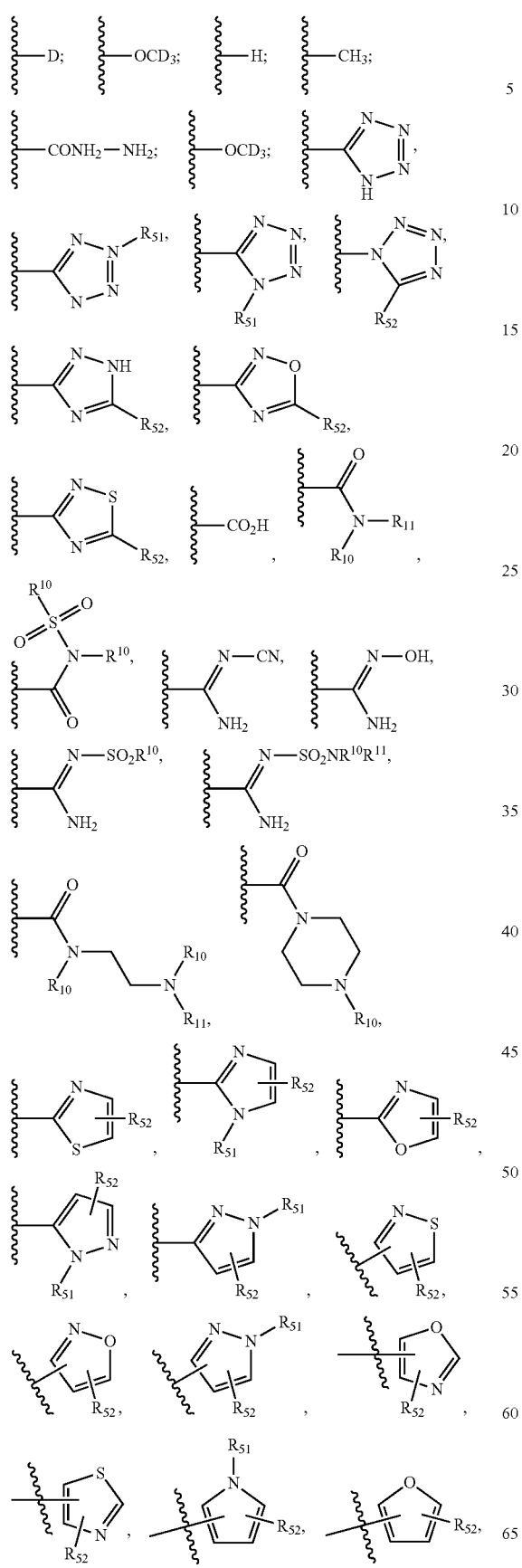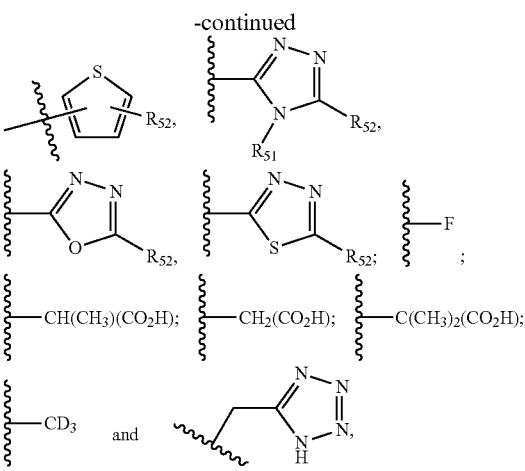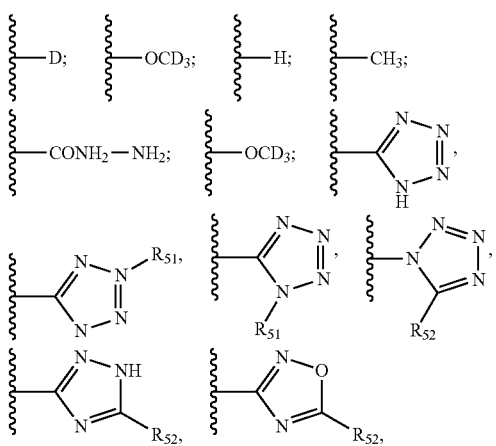

$R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{51}$ is selected from the group consisting of hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted;

$R^{52}$ is selected from the group consisting of hydrogen, halo, hydroxy, alkoxy, fluoroalkoxy, alkyl, aryl, heteroaryl, arylalkyl, cycloalkylalkyl, heteroarylalkyl, haloalkyl, $C(O)NR^{10}R^{11}$ and $SO_2NR^{10}R^{11}$, wherein alkoxy, fluoroalkoxy, alkyl, aryl, heteroaryl, arylalkyl, cycloalkylalkyl, heteroarylalkyl and haloalkyl are optionally substituted.

4. A compound according to claim 2, wherein $R^7$ and $R^8$ is selected from the group consisting of:

103

-continued

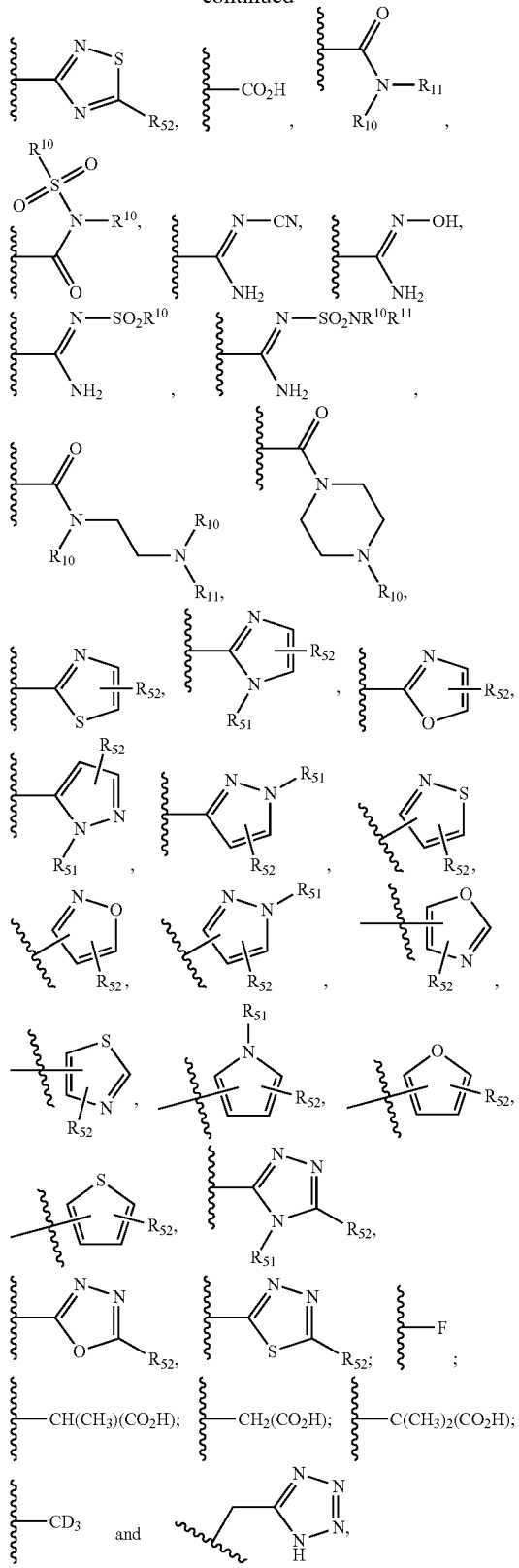

$R^{10}$ and $R^{11}$ are independently selected from the group consisting of hydrogen, deuterium, alkyl, deuteroalkyl, $CD_3$, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{10}$ and $R^{11}$ when taken together with the nitrogen to which they are attached complete a 3- to 8-membered ring containing carbon atoms and optionally containing a heteroatom selected from O, S, or $NR^{50}$ and which is optionally substituted;

$R^{51}$ is selected from the group consisting of hydrogen, alkyl, aryl, heteroaryl, arylalkyl, cycloalkylalkyl, heteroarylalkyl and haloalkyl, wherein alkyl, aryl, heteroaryl, arylalkyl, cycloalkylalkyl, heteroarylalkyl and haloalkyl are optionally substituted;

$R^{52}$ is selected from the group consisting of hydrogen, halo, hydroxy, alkoxy, fluoroalkoxy, alkyl, aryl, heteroaryl, arylalkyl, cycloalkylalkyl, heteroarylalkyl, haloalkyl, $C(O)NR^{10}R^{11}$ and $SO_2NR^{10}R^{11}$, wherein alkoxy, fluoroalkoxy, alkyl, aryl, heteroaryl, arylalkyl, cycloalkylalkyl, heteroarylalkyl and haloalkyl are optionally substituted.

5. A compound selected from the group consisting of:

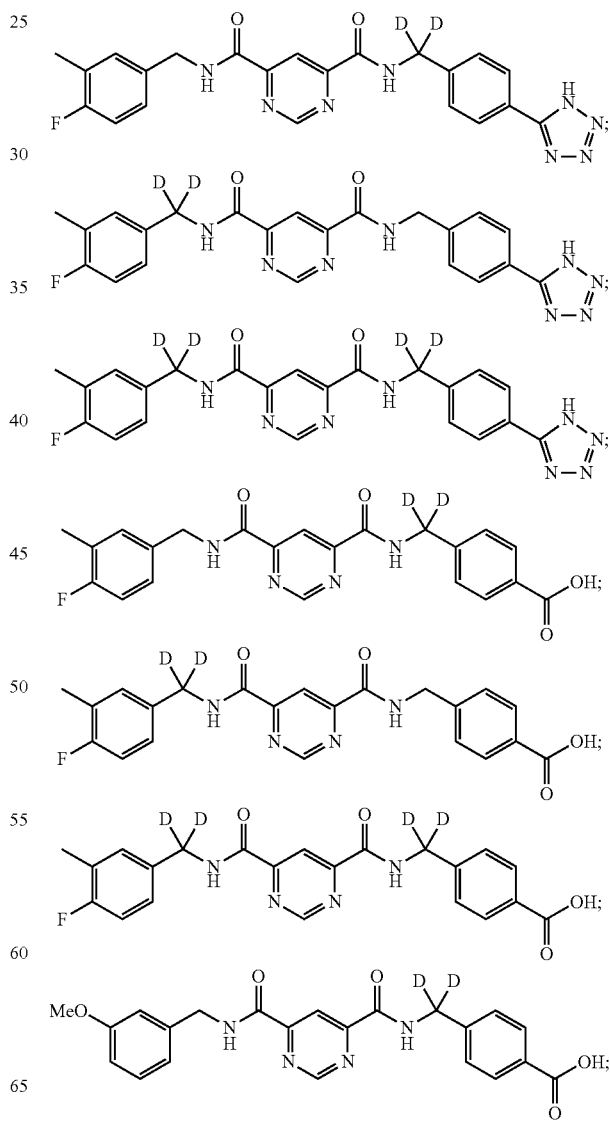

-continued

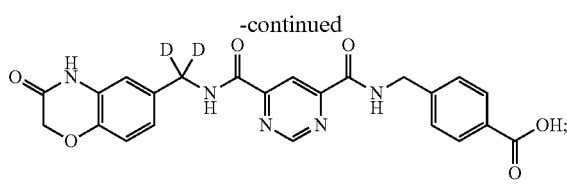
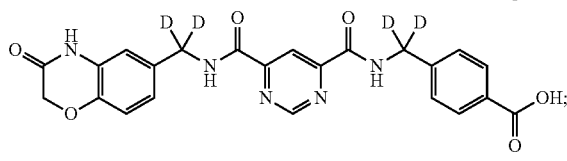
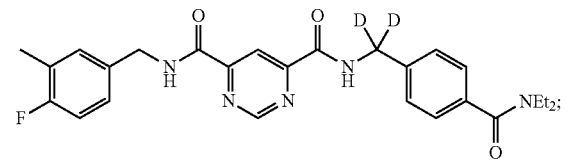
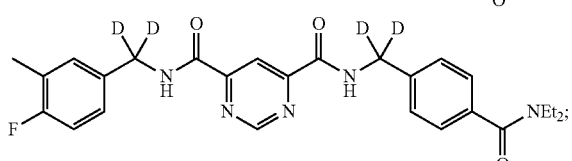
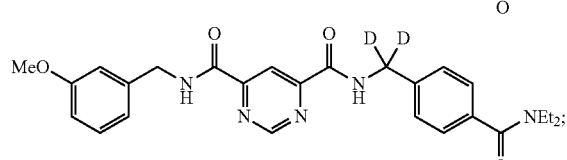
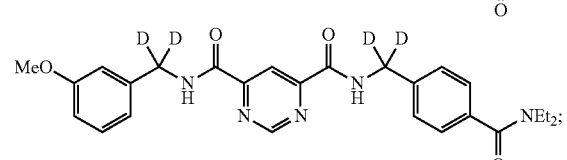
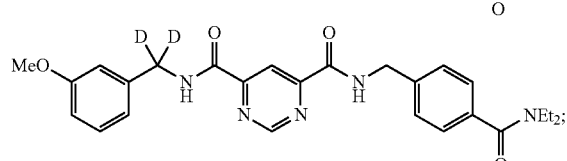
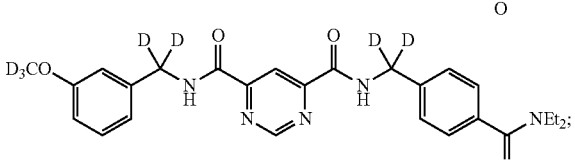
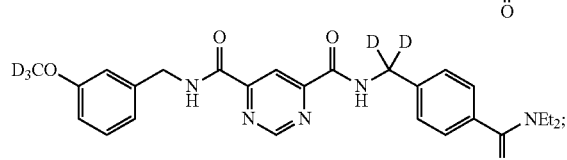
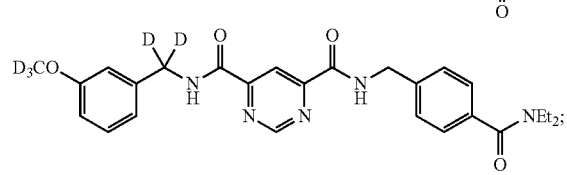
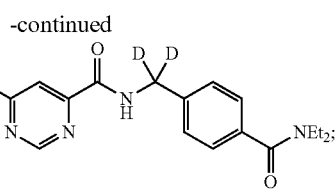
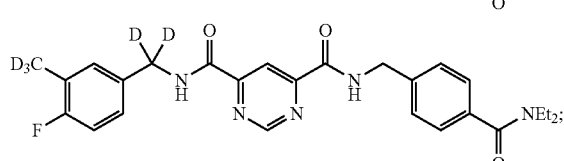
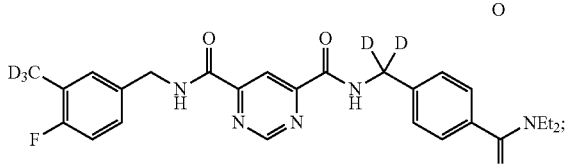
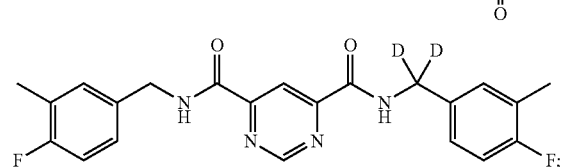
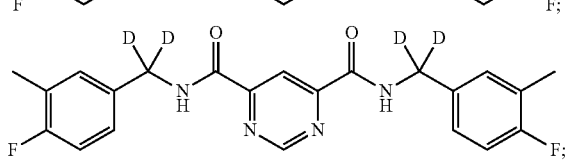
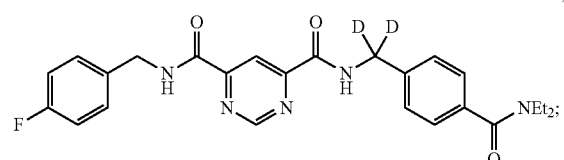
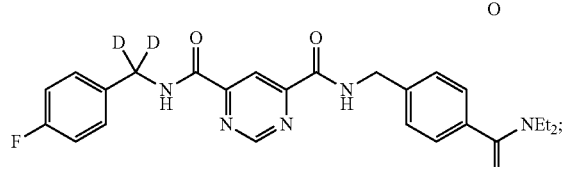
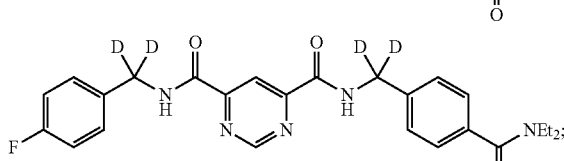
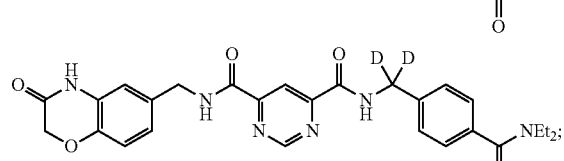
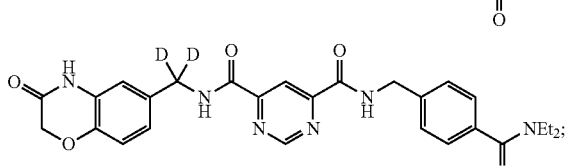
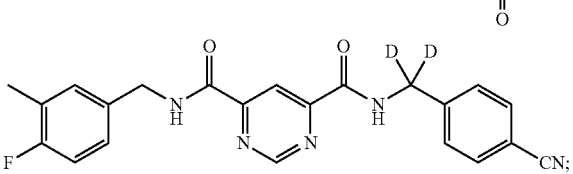

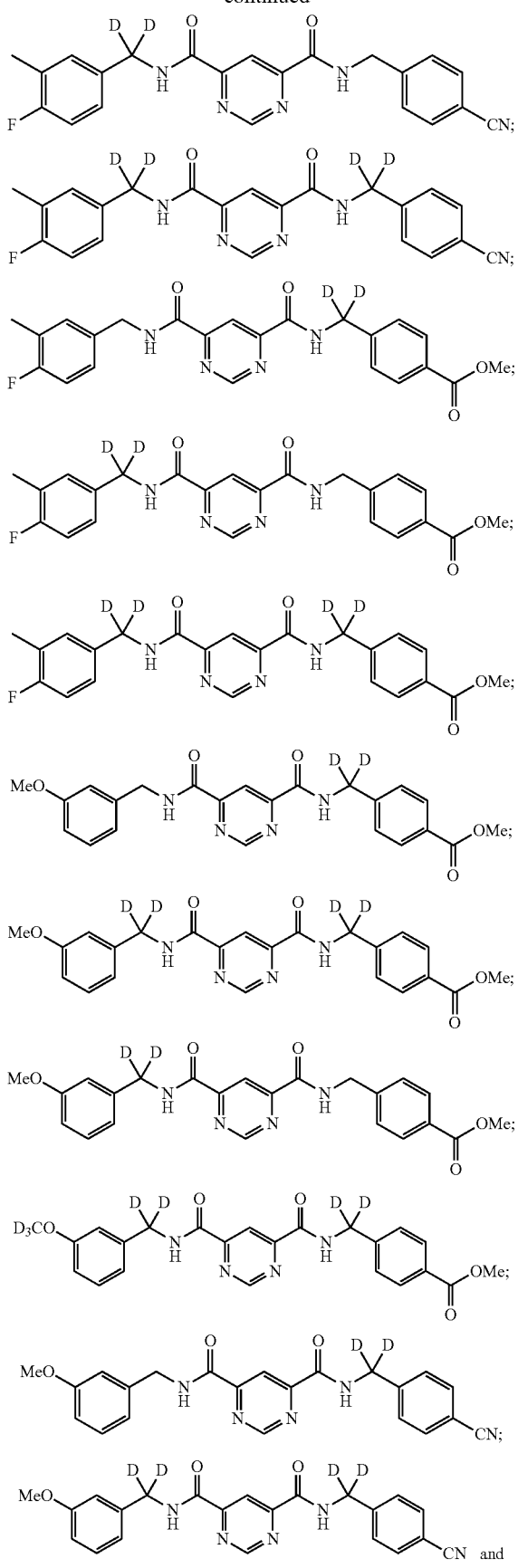

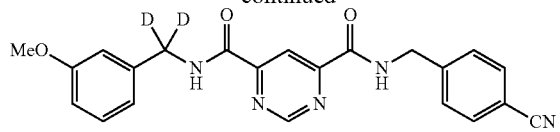

wherein each deuterium has an isotopic enrichment that is ≥1%:
or a pharmaceutically acceptable salt thereof.

6. A pharmaceutical composition comprising an effective amount of a compound according to claim 1 and a pharmaceutically acceptable carrier, diluent or excipient.

7. A pharmaceutical composition comprising an effective amount of a compound according to claim 2 and a pharmaceutically acceptable carrier, diluent or excipient.

8. A method of inhibiting MMP-13, comprising contacting a composition comprising a compound according to claim 2 with MMP-13.

9. A method of treating a disease selected from the group consisting of rheumatoid arthritis, osteoarthritis, abdominal aortic aneurysm, inflammation, atherosclerosis, multiple sclerosis, pain, chronic obstructive pulmonary disease, and cancer selected from the group consisting of breast carcinoma, squamous cell carcinomas of the head and neck, and vulvar squamous cell carcinoma, comprising administering to a patient in need of treatment an effective amount of a compound according to claim 2.

10. The method according to claim 9, wherein the disease is rheumatoid arthritis.

11. The method according to claim 9, wherein the disease is osteoarthritis.

12. The method according to claim 9, wherein the disease is abdominal aortic aneurysm.

13. The method according to claim 9, wherein the disease is inflammation.

14. The method according to claim 9, wherein the disease is atherosclerosis.

15. The method according to claim 9, wherein the disease is multiple sclerosis.

16. The method according to claim 9, wherein the disease is pain.

17. The method according to claim 16, wherein the pain is inflammatory pain.

18. The method according to claim 16, wherein the pain is bone pain.

19. The method according to claim 16, wherein the pain is joint pain.

20. The method according to claim 9, wherein the disease is chronic obstructive pulmonary disease.

21. A pharmaceutical composition comprising an effective amount of a compound according to claim 2, a pharmaceutically acceptable carrier and a drug, agent or therapeutic selected from the group consisting of: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; (h) other anti-inflammatory agents or therapeutics useful for the treatment of chemokine mediated diseases; and (i) a viscosupplement.

22. A process for the synthesis of a compound containing deuterium at one or more benzylic positions according to claim 1 comprising the step of reducing a corresponding substituted benzonitrile of the formula:

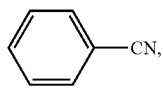

with a reducing agent.

23. The process of claim 22 wherein said reducing agent contains deuterium.

24. The process of claim 23 wherein said deuterium containing reducing agent is deuterium gas and a transition metal-containing catalyst selected from the group consisting of palladium-on-alumina, palladium-on-carbon, platinum-on-carbon, $PtO_2$, Raney Nickel and rhodium-on-carbon.

25. The process of claim 22, wherein said deuterium containing reducing agent is selected from the group consisting of $NaBD_4$, $LiAlD_4$, $NaAlD_4$ and Sodium bis(2-methoxyethoxy) aluminumdeuteride.

26. The method according to claim 9, wherein the administration is oral.

27. The method according to claim 9, wherein the administration is intraarticular.

28. The method according to claim 9, wherein the administration is transdermally using a transdermal delivery system.

* * * * *

UNITED STATES PATENT AND TRADEMARK OFFICE
CERTIFICATE OF CORRECTION

PATENT NO. : 9,505,743 B2
APPLICATION NO. : 14/433692
DATED : November 29, 2016
INVENTOR(S) : Irving Sucholeiki It is certified that error appears in the above-identified patent and that said Letters Patent is hereby corrected as shown below:

In the Claims

In Column 101, Lines 10-15 (Claim 3),

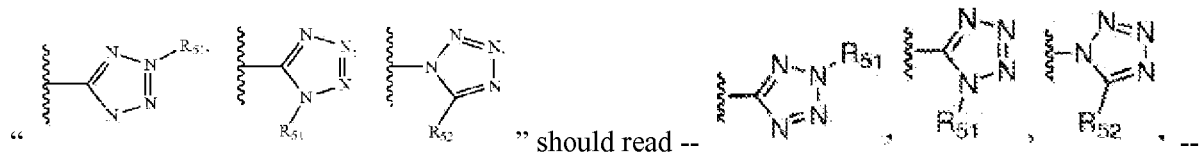

In Column 102, Lines 58-63 (Claim 4),

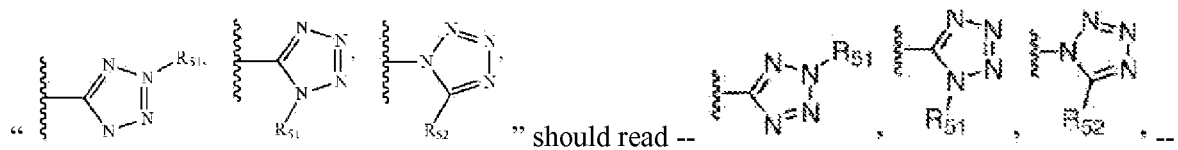

Signed and Sealed this
Twenty-fifth Day of April, 2017

Michelle K. Lee
*Director of the United States Patent and Trademark Office*